(12) United States Patent
Lazar

(10) Patent No.: US 11,124,836 B2
(45) Date of Patent: Sep. 21, 2021

(54) METHOD FOR SELECTING PERSONALIZED TRI-THERAPY FOR CANCER TREATMENT

(71) Applicant: WORLDWIDE INNOVATIVE NETWORK, Villejuif (FR)

(72) Inventor: Vladimir Lazar, Villejuif (FR)

(73) Assignee: WORLDWIDE INNOVATIVE NETWORK, Villejuif (FR)

( * ) Notice: Subject to any disclaimer, the term of this patent is extended or adjusted under 35 U.S.C. 154(b) by 593 days.

(21) Appl. No.: 15/316,529

(22) PCT Filed: Jun. 15, 2015

(86) PCT No.: PCT/EP2015/063263
§ 371 (c)(1),
(2) Date: Dec. 6, 2016

(87) PCT Pub. No.: WO2015/193212
PCT Pub. Date: Dec. 23, 2015

(65) Prior Publication Data
US 2017/0159128 A1    Jun. 8, 2017

(30) Foreign Application Priority Data
Jun. 16, 2014  (EP) .................................... 14305918

(51) Int. Cl.
| | |
|---|---|
| *C12Q 1/6886* | (2018.01) |
| *G16B 50/20* | (2019.01) |
| *G16B 30/00* | (2019.01) |
| *G16B 20/20* | (2019.01) |
| *G16B 25/10* | (2019.01) |
| *G16B 20/10* | (2019.01) |
| *G16B 5/20* | (2019.01) |
| *G16H 50/20* | (2018.01) |
| *G16H 50/30* | (2018.01) |
| *A61P 35/00* | (2006.01) |

(52) U.S. Cl.
CPC ............. *C12Q 1/6886* (2013.01); *G16B 5/20* (2019.02); *G16B 20/10* (2019.02); *G16B 20/20* (2019.02); *G16B 25/10* (2019.02); *G16B 30/00* (2019.02); *G16B 50/20* (2019.02); *G16H 50/20* (2018.01); *G16H 50/30* (2018.01); *A61P 35/00* (2018.01); *C12Q 2545/113* (2013.01); *C12Q 2600/106* (2013.01); *C12Q 2600/112* (2013.01); *C12Q 2600/156* (2013.01); *C12Q 2600/158* (2013.01); *C12Q 2600/178* (2013.01)

(58) Field of Classification Search
None
See application file for complete search history.

(56) References Cited

PUBLICATIONS

Ahn, T. et al. "Pathway-Driven Discovery of Rare Mutational Impact on Cancer" *Biomed Research International*, May 4, 2014, pp. 1-10, vol. 2014, Article ID 171892.

Craig, D. W. et al. "Genome and Transcriptome Sequencing in Prospective Metastatic Triple-Negative Breast Cancer Uncovers Therapeutic Vulnerabilities" *Molecular Cancer Therapeutics*, Jan. 2013, pp. 104-116, vol. 12, No. 1.

Lazar, V. et al. "A simplified interventional mapping system (SIMS) for the selection of combinations of targeted treatments in non-small cell lung cancer" *Oncotarget*, Apr. 3, 2015, pp. 14139-14152, vol. 6, No. 16.

Migliardi, G. et al. "Inhibition of MEK and PI3K/mTOR Suppresses Tumor Growth but Does Not Cause Tumor Regression in Patient-Derived Xenografts of RAS-Mutant Colorectal Carcinomas" *Clinical Cancer Research*, May 1, 2012, pp. 2515-2525, vol. 18, No. 9.

Nakade, J. et al. "Triple Inhibition of EGFR, MET, and VEGF Suppresses Regrowth of HGF-Triggered, Erlotinib-Resistant Lung Cancer Harboring an EGFR Mutation" *Journal of Thoracic Oncology*, Jun. 2014, pp. 775-783, vol. 9, No. 6.

Roychowdhury S. et al. "Personalized Oncology Through Integrative High-Throughput Sequencing: A Pilot Study" *Science Translational Medicine*, Nov. 30, 2011, pp. 1-20, vol. 3, No. 111.

Simon, R. et al. "Implementing personalized cancer genomics in clinical trials" *Nature Reviews*, May 2013, pp. 358-369, vol. 12, No. 5.

Written Opinion in International Application No. PCT/EP2015/063263, dated Oct. 30, 2015, pp. 1-10.

Kessler, T. et al. "Integrative analysis of cancer-related signaling pathways" *Frontiers in Physiology*, Jun. 4, 2013, pp. 1-19, vol. 4, Article 124.

*Primary Examiner* — G Steven Vanni
(74) *Attorney, Agent, or Firm* — Saliwanchik, Lloyd & Eisenschenk

(57) ABSTRACT

The present invention relates to a method for determining the best combinations of at least three drugs for treating cancer, which is based on the determination of the most relevant intervention points for an individual.

7 Claims, 3 Drawing Sheets

A. The Simplified Intervention Mapping System (SIMS)

B. Intervention points prioritization (Intervention score)

C. Proposing useful combinations

Frequently co- occurring high priority intervention points → Domain experts → Testing

METHOD FOR SELECTING PERSONALIZED TRI-THERAPY FOR CANCER TREATMENT

CROSS-REFERENCE TO RELATED APPLICATION

This application is the U.S. national stage application of International Patent Application No. PCT/EP2015/063263, filed Jun. 15, 2015.

FIELD OF THE INVENTION

The present invention relates to the field of oncology, especially to personalized medicine in cancer therapy. More particularly, it relates to a new concept of therapeutic approach, the triple regimen therapy and method for selecting the most appropriate combinations of drugs for treating cancer in a particular subject.

BACKGROUND OF THE INVENTION

Lung cancer is the most common malignancy worldwide with a staggering 1.8 million cases diagnosed per year. Over half of NSCLC are diagnosed at the metastatic stage. Even utilizing the standard of care in the Western world, consisting mainly of chemotherapeutic agents and radiation therapy, there has been little impact on mortality, with only 30% of all patients diagnosed (regardless of stage) alive at one year, and a dismal 1 and 5 year survival rates of about 8-15% and 4%, respectively for those with metastatic disease. For patients that have failed first line therapy, the median survival is only about 7 months.

Progress brought by targeted therapies such as matching EGFR activating mutations or ALK translocation have shown substantial response rates, demonstrating the potency of molecularly-matched targeted therapy, but monotherapies such as these apply to only small subsets of patients, and virtually all patients develop resistance and succumb to their disease. This is perhaps not unexpected, as patients often harbor multiple molecular aberrations that require prosecution. The power of combination therapy has been illustrated in diseases such as Hodgkin's lymphoma where cure was effected by combinations. Further in the modern era of targeted therapy, combinations targeting the same pathway (e.g. trametanib (MEK)) inhibitor together with dabrafenib (BRAF inhibitor) in BRAF-mutant melanoma, or resistance pathways (combining PIK3CA and MEK inhibitors) are already being tested and have shown efficacy, in some cases, but no cure and no significant impact on survival. Combinations of targeted therapy in NSCLC have, however, to date, been very limited in scope.

Personalized medicine today offers modest benefits in advanced metastatic disease (especially lung cancer). Monotherapies have failed to cure advanced diseases. Most combination chemotherapies lack an underlying biologic or molecular rationale.

Therefore, there is a strong need to define, for each specific patient, the best combinations of drugs for treating cancer.

SUMMARY OF THE INVENTION

The inventor presents a novel concept of therapy in cancer, in particular metastatic lung cancer, based on tri therapy associating three targeted drugs to create a simplified interventional mapping system (SIMS) merging knowledge from drugs and hallmarks of cancer. An interventional point means a target/gene, or a group of targets/genes, activated and that can be blocked by a drug. Twenty-four (24) interventional points based on a collection of 183 genes are described. Method of investigation of status of activation of the interventional points is based on complete genomics investigation of dual tumor and normal biopsies matched from strictly the same points, and preferably comprise sequencing, copy number variation gene expression and miRNA expression. An algorithm was developed to create a scoring system, e.g. from 1 to 10, enabling the ranking of the activated interventional points in each patient.

Based on score and trends of co-activation of interventional points, the invention presents a new scientific rationale to associate combination of therapies. Accordingly, the present invention relates to a method for determining in a patient having a cancer a classification of intervention points according to their activation status, wherein the intervention points comprise the group consisting of the HER, CDK4,6, PLK/AURK/Kinesins, Angiogenesis, Angiopoietins, Immune Modulators, PI3K, MET, MEK, ERK, Anti-Apoptosis, FGF, mTOR, Ras/Raf, Telomerase, IGF/glycolysis, Wnt, PARP, HDAC, JAK-STAT, Hedgehog, NOTCH pathway, DNA Repair and Others' (namely RET, ALK, ROS1 and UB1), or any subgroup thereof of at least 10 intervention points; and the genes of each intervention point are defined according to Table 1 or 9;

the method comprises;

characterizing a tumor sample in comparison to a normal histologically matched sample from the same patient, including:

for each pathway of the group or subgroup of intervention points, determining the mRNA expression level of the genes of the intervention point as disclosed in Table 1 or 9, thereby determining a fold change of mRNA expression of tumor vs normal, (referred as mRNA TvN fold change);

wholly or partially sequencing genes of Table 1 or 9, thereby identifying the presence of activating mutation in the tumor sample;

optionally, for each intervention point of the group or subgroup of intervention points, determining the level of miRNAs of the genes of the intervention point as disclosed in Table 1 or 9, thereby determining a fold change of miRNAs level of tumor vs normal, (referred as miRNA TvN fold change);

optionally, for each intervention point of the group or subgroup of intervention points, determining the copy number variation of the genes of the intervention point as disclosed in Table 1 or 9, thereby determining a tumor vs normal fold change for the amplified genes;

calculating a score for each pathway based on the characterization data, wherein if, in the tumor sample, the presence of an activating mutation of a gene of an intervention point is detected, then a maximal score is given to the intervention point, in particular a score of 10 if the scoring is from 1 to 10;

a score, preferably from 1 to 10, is calculated based on the arithmetic mean of the mRNA TvN fold changes of the genes for each intervention point of the group or subgroup of intervention points, provided that the mRNA TvN fold change of a gene is taken into consideration only if its value is at least 1.3; and the score of each intervention point of the group or subgroup of intervention points is either
  a) the sum of the score due to the presence of an activating mutation and the score calculated by the average of the mRNA TvN fold changes; or
  b) the score due to the presence of an activating mutation if there is a mutation or the score calculated based on the arithmetic mean of the mRNA TvN fold changes in absence of mutation; and
classifying the intervention points according to the calculated scores.

Preferably, the genes of Table 10 are sequenced for detecting the presence of mutations as defined in Table 10 and p53 gene is sequenced.

Preferably, for each intervention point of the group or subgroup of intervention points, the method comprises determining the miRNAs level of the genes of the pathway as disclosed in Table 1 or 9, in particular the level of miRNAs of the genes of the pathway as disclosed in Table 11. More preferably, before the step of score calculation, a mean miRNAs fold change for each gene is calculated as the average of the miRNA TvN fold changes for the gene, a corrected mRNA TvN fold change is calculated by dividing the mRNA fold change Tumor versus Normal of the gene (mRNA TvN fold change) by the mean fold change for the miRNAs of the gene (mean miRNA TvN fold change), and the corrected mRNA TvN fold change of the gene is then used to calculate the arithmetic mean of the mRNA TvN fold changes of the genes for each intervention point. In a preferred embodiment, the level of miRNAs is determined and used to calculate a corrected mRNA TvN fold change for the genes of the following intervention points: mTOR-AKT-PTEN, RAS, ERK, PI3K and Immune Modulators.

Preferably, for each intervention point of the group or subgroup of intervention points, the method comprises determining the copy number variation of the genes of the pathway as disclosed in Table 1 or 9. More preferably, before the step of score calculation, a corrected mRNA TvN fold change of a gene of an intervention point is calculated by multiplying the mRNA TvN fold change of the gene by the CNV fold change of the gene, and the corrected mRNA TvN fold change of the gene is then used to calculate the arithmetic mean of the mRNA TvN fold changes of the genes for each intervention point.

Preferably, the subgroup of intervention points consists of the following groups: HER CDK4,6, PLK/AURK/Kinesins, Angiogenesis, Immune Modulators, PI3K, MET, MEK, ERK, Anti-Apoptosis, FGF, mTOR, Ras/Raf, IGF/glycolysis, Wnt, PARP, and DNA Repair.

Preferably, the subgroup further comprises selecting a group of three activated or disturbed intervention points in a patient having a cancer, wherein three intervention points are selected among the intervention points having the higher scores, preferably the three intervention points having the higher scores.

The present invention also relates to a method for selecting a combination of three drugs useful for treating a patient having a cancer, wherein a group of three activated or disturbed intervention points are selected by the method of claim 9 and a drug is selected for each activated or disturbed intervention point, thereby providing a combination of three drugs.

In addition, the present invention relates to the use of a kit for classifying pathways according to their activation status, wherein the kit comprises means for measuring the mRNA expression level of the genes of Table 1 or 9 for intervention points comprising the group consisting of the HER, CDK4, 6, PLK/AURK/Kinesins, Angiogenesis, Angiopoietins, Immune Modulators, P13K, MET, MEK, ERK, Anti-Apoptosis, FGF, mTOR, Ras/Raf, Telomerase, IGF/glycolysis, Wnt, PARP, HDAC, JAK-STAT, Hedgehog, NOTCH pathway, DNA Repair and Others' (namely RET, ALK, ROS1 and UB1), or any subgroup thereof of at least 10 intervention points. Preferably, the kit further comprises means for detecting the mutations of Table 10. More preferably, the kit further comprises means for measuring the miRNA level of miRNA of Table 11 for intervention points comprising the group consisting of the HER, CDK4,6, PLK/AURK/Kinesins, Angiogenesis, Angiopoietins, Immune Modulators, PI3K, MET, MEK, ERK, Anti-Apoptosis, FGF, mTOR, Ras/Raf, Telomerase, IGF/glycolysis, Wnt, PARP, HDAC, JAK-STAT, Hedgehog, NOTCH, DNA Repair and Others' (namely RET, ALK, ROS1 and UB1), or any subgroup thereof of at least 10 intervention points. Optionally, the kit further comprises means for determining the copy number variation of the genes of Table 1 or 9 for pathways comprising the group consisting of the HER, CDK4,6, PLK/AURK/Kinesins, Angiogenesis, Angiopoietins, Immune Modulators, P13K, MET, MEK, ERK, Anti-Apoptosis, FGF, mTOR, Ras/Raf, Telomerase, IGF/glycolysis, Wnt, PARP, HDAC, JAK-STAT, Hedgehog, NOTCH, DNA Repair and Others' (namely RET, ALK, ROS1 and UB1), or any subgroup thereof of at least 10 intervention points.

Finally, the present invention relates to a drug combination for use in the treatment of cancer, wherein the drug combination is selected among the combinations disclosed in Table 6, Table 7, Table 8 or selected from the group consisting of:
  anti PD1L+Pan RAF inhibitor+MtorP13K inhibitor,
  anti PD1L+Pan RAF inhibitor+angiogenesis inhibitor,
  anti PD1L+Pan RAF inhibitor+MET inhibitor,
  anti PD1L+Pan RAF inhibitor+CDK4,6 inhibitor,
  anti CTLA4+Pan RAF inhibitor+MtorP13K inhibitor,
  anti CTLA4+Pan RAF inhibitor+angiogenesis inhibitor,
  anti CTLA4+Pan RAF inhibitor+MET inhibitor,
  anti CTLA4+Pan RAF inhibitor+CDK4,6 inhibitor,
  anti PD1L+MEK inhibitor+MtorPI3K dual inhibitor,
  anti PD1L+MEK inhibitor+angiogenesis inhibitor,
  anti PD1L+MEK inhibitor+MET inhibitor,
  anti PD1L+MEK inhibitor+CDK,-6 inhibitor,
  anti CTLA4+MEK inhibitor+MtorPI3K dual inhibitor,
  anti CTLA4+MEK inhibitor+MET inhibitor,
  anti CTLA4+MEK inhibitor+angiogenesis inhibitor, and
  anti CTLA4+MEK inhibitor+CDK4,6 inhibitor.

Preferably, the drugs included in the combination are selected from those disclosed in Table 1.

More preferably, the drugs combination is selected from the group consisting of:
  Medi-4736 (Astra Zeneca)+MLN2480 (Takeda)+PF-384 (Pfizer),
  Medi-4736 (Astra Zeneca)+MLN2480 (Takeda)+Axitinib (Pfizer) or Motesanib (Takeda),
  Medi-4736 (Astra Zeneca)+MLN2480 (Takeda)+Crizotinib (Pfizer),
  Medi-4736 (Astra Zeneca)+MLN2480 (Takeda)+Palbociclib (Pfizer),
  Tremelimumab (Astra Zeneca)+MLN2480 (Takeda)+PF-384 (Pfizer),
  Tremelimumab (Astra Zeneca)+MLN2480 (Takeda)+Axitinib (Pfizer) or Motesanib (Takeda),
  Tremelimumab (Astra Zeneca)+MLN2480 (Takeda)+Crizotinib (Pfizer),
  Tremelimumab (Astra Zeneca)+MLN2480 (Takeda)+Palbociclib (Pfizer), Medi-4736 (Astra Zeneca)+Selumetinib (Astra Zeneca)+PF-384 (Pfizer), Medi-4736 (Astra Zeneca)+Selumetinib (Astra Zeneca)+Axitinib (Pfizer) or Motesanib (Takeda), Medi-4736 (Astra Zeneca)+Selumetinib (Astra Zeneca)+Crizotinib (Pfizer), Medi-4736 (Astra Zeneca)+Selumetinib (Astra Zeneca)+Palbociclib (Pfizer), Tremelimumab (Astra Zeneca)+Selumetinib (Astra Zeneca)+PF-384 (Pfizer), Tremelimumab (Astra Zeneca)+Selumetinib (Astra Zeneca)+Crizotinib (Pfizer), Tremelimumab (Astra Zeneca)+Selumetinib (Astra Zeneca)+Axitinib (Pfizer) or Motesanib (Takeda), and Tremelimumab (Astra Zeneca)+Selumetinib v+Palbociclib (Pfizer).

Preferably, the cancer is a lung cancer, more preferably a NSCLC.

DETAILED DESCRIPTION OF THE INVENTION

General Concept

Since monotherapies fail to cure metastatic lung cancer diseases anddual combination therapies reported for other diseases do not significantly impact survival, the inventor envisions applying tri-therapy, following the historical success in AIDS.

The challenge raised by the invention is choosing triple drug combinations that can benefit a patient.

Single drugs are doing poorly; patients respond but inevitably relapse, often within a few months. Based on the molecular complexity of metastatic disease, combinations are needed. This situation may be analogous to that with AIDS, wherein single agents resulted in incremental effects, but combination of three drugs has demonstrated long-term benefit.

Unlike viruses, which always depend on the same proteins, tumors are heterogeneous and the biology is too complex for a single tri-therapy combination to work on all tumors.

As a result, combinatorial precision cancer medicine (cPCM) is needed.

A limited number of pathways may be abnormal in metastatic tumors.

The Proposed Approach

The inventor asserts that, by reasonable assumptions, a realistic framework can be established today that would allow useful drug combinations to be identified in a personalized way (i.e. matching the combination to the patient based on the tumor properties).

The main idea is to divide and conquer—proposing 3 steps:
1. Find a set of markers that are indicative for specific interventional points of every class of drug: 24 markers covering 183 genes;
2. Find a score that summarizes the behavior of these markers in a given patient that is both comparable to other classes and is proportional to the probability that this drug would work; and
3. Figure out how to combine drugs such that the combination is common enough to allow clinical testing yet retain the ability to match combinations to patients with sufficient precision.

Figure 1:
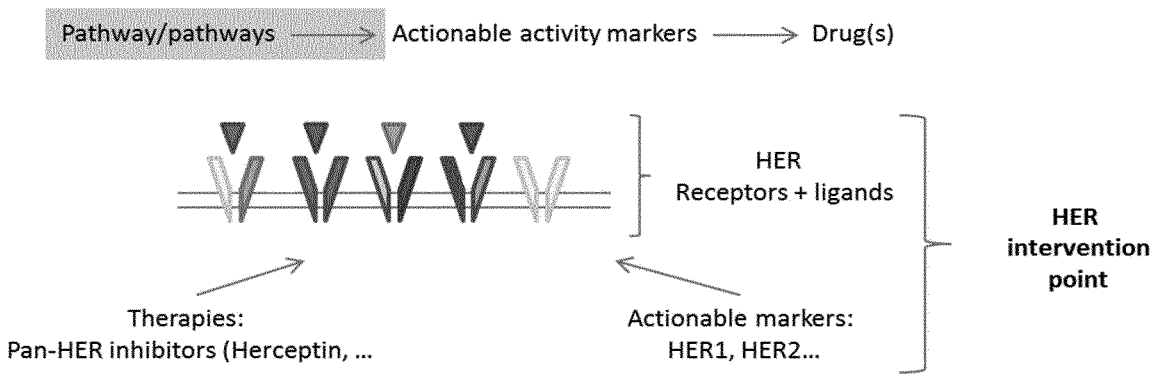
FIG. 1. The framework for cPCM. The problem is divided into 3 parts:
A. Mapping therapeutic efficacy to cellular components;
B. Scoring the status of specific nodes in the interventional maps defined in (A); and (C) predicting combination efficacy.
Figure 1:
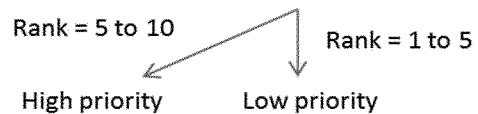

Based on these assumptions, the inventor proposes the SIMS (Simplified interventional points mapping system) framework for precision combinational cancer medicine (FIG. 1).

First, the enormous complexity of biological pathways and pathway cross-talk is reduced by devising a simplified map that only concentrates on the genes that are most indicative of drug target status. It is proposed that "intervention points", which consist of drug targets or group of targets as well as genes upstream of the targets that together reflect a specific biological activity that is actionable through therapeutic interventions. For example, pan-HER therapies define the HER group of receptors and their ligands as a single intervention point (FIG. 1a).

The second part of the work, the inventor proposes a very simple approach for prioritizing intervention points for a specific patient. The basic premise behind the score is that, when the genes associated with an intervention point are more disturbed (in terms of sequence and/or expression level), the intervention point is more likely to be crucial to the tumor. From this, it seems that the more disturbed the genes of an intervention point, the more likely it is that therapeutics targeted at that point will benefit the patient. The inventor is in the process of developing a family of simple scores that combine the level of gene expression in the tumor (relative to matched normal control), the aberrations found in the intervention points' genes, CNVs and miRNAs expression levels. Rank normalization (in the example, using deciles) is used to make the scores of different intervention points comparable.

Finally, given a reliable system for determining which drugs are more likely to benefit the patient, a method is needed for choosing combinations that are likely to benefit the patients. Here the inventor proposes a statistical approach, using a panel of 123 lung cancer patients as an example. Using the methods described above, the status of 24 intervention points in the 123 patients is described. From this, a knowledge-driven approach to look for drug combinations is applied that is likely to synergistically benefit the patient. Using a panel of experts, pathways are identified that co-occur frequently in the patients and are mechanistically independent. To further improve the efficacy of the proposed combinations, the inventor proposes augmenting the combined targeted therapies with immunomodulating therapies (i.e. anti-CD1L and anti-CTLA). The rationale behind this combination is to reduce the chance of intolerable side effects while maintaining the predicted efficacy of a triple therapy regimen.

Table 1 summarizes the interventional points presenting genes involved and main classes of drugs

| Interventional node | Components of the inteventional points | Drugs acting on interventional points |
| --- | --- | --- |
| HER | EGF, TGFA, AREG, EREG, HBEGF, BTC, NRG1, NRG2, NRG4, EGFR, ERBB2, ERBB3, ERBB4 | Dacomitinib-Panher inhibitor Pfizer |
| CDK4,6 | CDK4, CDK6, CCND1, CCND2, CCND3, CDKN2A, CDKN2B, CCNE1, CCNE2, CCNE3, RB1 | Palbociclib CDK4, 6 inhibitor Pfizer |
| PLK/AURK/Kine | PLK1, AURKA, BORA, ILK, KIF11 | MLN8237 (Aurora A kin inhib) Takeda |
| ANGIOGENESIS | VEGFA, VEGFB, VEGFC, VEGFD, VEGFR1, VEGFR2, VEGFR3, PDGFA, PDGFB, PDGFRA, PDGFRB, Kit | Axitinib antiVEGFR Pfizer Motesanib anti VEGFR/PDGFR/kit Takeda |
| Angiopoietins | THBS1, TGFB1, ANGPT1, ANGPT2, ANGPTL1, ANGPT4, TIE1, TEK | — |
| Immune mod | PD1L, PDCD1LG2, PDCD1, CTLA4, LAG3 | Medi-4736 (PDL1) AZ (Astra Zeneca) AMP514 (PD1) AZ Tremelimumab (CTLA4) AZ PF-05082566 (4-1 BB) |
| PI3K | PIK3CA, PIK3CB, PIK3CD, PIK3CG, PIK3C2B, PRKCB, PRKCA, PRKCB, PIK3R1, PIK3R2, PIK3R3 | PF-384 PI3K/mTOR-inhibitor Pfizer AZD8186 (PI3Kb)AZ MLN1117 (PI3Kalpha inhibitor) Takeda |
| MET | HGF, MET, AXL, MST1R | Crizotinib Pfizer Volitinib (cMet) AZ MLN1117, MLN0128 Takeda |
| MEK | MAP2K1, MAP2K2, MAP2K3, MAP2K4, MAP3K1, MAP3K2, MAP3K3, MAP3K4 | Selumetinib (MEK) AZ |
| ERK | MAPK3, MAPK1, KSR1, MAPK11 | — |
| Anti-apoptosis | BCL2, BCLXL, BIRC5, XIAP, BAK1, TP53 | — |
| FGF | FGF1 to FGF18, FGFR1, FGFR2, FGFR3, FGFR4 | AZD4547 (FGFR1, 2, 3) AZ |
| mTOR | mTor, AKT1, AKT2, PTEN, TSC1, TSC2, STK11, PIM1, PIM2, PIM3 | PF-384 PI3K/mTOR inhibitor Pfizer AZD2014 (TOR kinase) AZ AZD5363 (AKT1, 2, 3) AZ AZD1208 (PIM1, 2) AZ MLN0128 (TORC1/TORC2) Takeda |
| Ras/Raf | KRAS, NRAS, HRAS, RAF1, BRAF, CRAF | MLN2480 (Pan-RAF inhibitor) Takeda |
| Telomerase | TERT, TERC, TEP1, HSP90AA1, DKC1, PTGES3 | — |
| IGF/glycolysis | IGF1, IGF2, IGF1R, IGF2R, INSR, IRS1, PKM | Medi-573 (IGF) AZ |
| Wnt | CDH1, CTNNA1, CTNNB1, WNT 1, FZD1, WNT5A, B, FZD5, WIF1, DKK1 | — |
| PARP | PARP1, BRCA1, XRCC1, RAD54L, RAD54B, ATM, ATR, CHEK1, CHEK2, WEE1 | Olaparib (PARP) AZ AZD1775 (Wee1) AZ AZD6738 (ATR) AZ |
| HDAC | HDAC1, HDAC2, HDAC3, HDAC4, HDAC5 | |
| JAK-STAT | JAK1, JAK2, STAT1, STAT2, STAT3, SOCS1 | |
| Hedgehog | SHH, PTCH1, SMO, STK36, PRKACA, SUFU, GLI1 | |
| NOTCH | NOTCH1, Adam17, PSEN1, NCSTN, JAG1, SRRT, APH1A | |
| DNA Repair | ERCC1, RAD52, XRCC4, RAD51, BRCA1, NEDD8, NAE1 | MLN 4924 (NEDD8 AE) Takeda |
| Others | RET, ALK, ROS1, UB1 | |

CONCLUSION

The inventor proposes a new therapeutic approach of triple regimen therapies aiming at blocking simultaneously three different biologic abnormalities and reducing the chance of developing the secondary resistance. In addition, for defining a combination of drugs, the inventor identified specific interventional points of drugs based on the pathways specifically up-regulated in one particular patient having a cancer to define a simplified interventional mapping system within the hallmarks of cancer including only signaling and regulatory pathways that can be targeted with therapeutic agents. The principle of simplification is based on the activating signal that can be blocked by a class of drugs.

Indeed, the inventor reduced the enormous complexity of biological pathways and pathway cross-talk by devising a simplified map that only concentrates on the genes that are most indicative of drug target status defined as "intervention points". These intervention points consist of drug targets or groups of drug targets and some genes upstream of the drug targets that together reflect a specific biological activity which is actionable through therapeutic interventions. By upstream is referred to genes encoding a protein having an extracellular activity. For instance, pan-HER therapies define the HER group of receptors and their ligands as a single intervention point.

The inventor proposes a very simple approach for prioritizing intervention points for a specific patient. The basic premise is that, when the genes associated with an intervention point are more disturbed (in terms of sequence and/or expression level), the intervention point is more likely to be crucial or critical to the tumor. From this, it seems that the more disturbed the genes of an intervention point are, the more likely it is that therapeutics targeting that points will benefit the patient. Accordingly, the inventor has developed a family of simple scores that combine the level of gene expression in the tumor (relative to matched normal control), the mutations found in the intervention points' genes, CNVs and miRNAs expression levels.

Therefore, the inventor proposes a method allowing the tumor characterization of one particular subject by considering its own tumor vs normal status in the most efficient way for identifying the disturbed or activated intervention points and ranking them. The inventor developed a new mathematical modelling and scoring system to give a score (e.g., of 1 to 10) based on integration of omics data, especially gene expression, sequencing, miRNA analysis and copy number variation determination.

Then, when the intervention points are ranked, it is possible to define one or several combinations of drugs targeting a combination of disturbed or activated intervention points so as to obtain the optimized therapy of cancer for this particular patient. Preferably, the combined therapy comprises or consists of three drugs targeting the most disturbed or activated intervention points. The method may further comprise the administration of the optimized combination of drugs to said patient. Accordingly, the method leads to rational combination therapies which are scientifically reliable and clinically feasible.

Tumor Characterization

The method comprises a step of characterizing the tumor in one patient of interest. In particular, the patient suffers from a cancer for which no effective therapy is established or admitted by physicians. The reasons of this situation could be an advanced stage of cancer, for instance a stage with metastases, a relapsed cancer after one or several lines of treatment, or even a cancer for which no established and efficient treatment is associated with. In particular, the cancers or tumors more particularly considered in the present invention are lung cancer, especially NSCLC (non-small cell lung cancer), breast cancer (in particular the triple negative breast cancer), colorectal cancers, kidney cancer, melanomas, brain cancers, liver cancers, head and neck cancers, stomach cancers and ovary cancers.

Therefore, the method comprises an initial step of providing samples from the patient. Two samples are necessary, namely one tumor sample and one normal sample from the same patient. Preferably, the tumor sample and the normal sample provides from the same type of tissue. More particularly, the tumor and normal samples are histologically matched tissues. Typically, the samples can be provided by biopsies. Non-exhaustively, examples of pairs of tumor with corresponding histological normal reference tissue are the following:

1. lung cancer adenocarcinomas or derived metastases—bronchial normal mucosa,
2. breast cancer tumors or derived metastases—normal epithelial breast cells,
3. colon cancers adenocarcinomas or derived metastases—normal colon mucosa,
4. kidney cancers or derived metastases—normal kidney cells,
5. melanomas or derived metastases—synchronous naevi,
6. rhabdomyosarcomas or derived metastases—normal muscle tissue,
7. liver carcinomas or derived metastases—normal liver cells,
8. Oral-pharyngeals tumors (ORL)—normal buccal mucosa,
9. Stomach carcinomas or derived metastases—normal stomach mucosa,
10. Ovary cancer—normal Fallopian tube mucosa,
11. pancreatic cancers—normal parenchimatous tissue from pancreas.

In order to optimize the tumor characterization, the inventor selected parameters that have to be analysed in order to establish the status of the intervention points that can be targeted by a class of drugs.

The inventor defined the main intervention points of interest, namely HER (Human Epithelial Growth Factor Receptor), CDK4,6 (Cyclin-Dependent Kinase), PLK/AURK/Kinesins (Polo-Like kinase/Aurora Kinase/Kinesins), Angiogenesis, Angiopoietins, Immune Modulators, PI3K (Phosphoinositide-3 Kinase), MET (cMET), MEK, ERK, Anti-Apoptosis, FGF (Fibroblast Growth Factor), mTOR (mammalian target of rapamycin), Ras/Raf, Telomerase, IGF/glycolysis (Insulin-like growth factor), Wnt, PARP (poly ADP ribose polymerase), HDAC (histone deacetylase), JAK-STAT (Janus tyrosine Kinase-Signal Transducer and Activator of Transcription), Hedgehog, NOTCH, DNA Repair and Others' intervention point (namely RET, ALK, ROS1 and UB1). These intervention points have been selected because they can be associated with an activation in a cancer. The rule that guides the choice of the invention in this selection is to select the activation signals that can be blocked.

Optionally, in an alternative method, a subgroup of intervention points can be selected among the above mentioned list of intervention points (i.e., a subgroup of 10, 12, 14, 16 or 18 intervention points). For instance, in a particular embodiment, a subgroup of intervention points of interest includes the intervention points for which drugs are available. For instance, such a subgroup may include or consist in the following group: Her, CDK4,6, PLK/AURK/Kinesins, Angiogenesis, Immune Modulators PD1L and CTL14, PI3K, MET, MEK, ERK, Anti-Apoptosis, FGF, mTOR, Ras/Raf, IGF/glycolysis, Wnt, PARP, and DNA Repair.

In addition, for each intervention point, the inventor carried out a selection of genes useful for characterizing this intervention point. The list of genes is disclosed in Table 1 or 9.

In order to define the status of these intervention points in the tumor, several parameters have to be defined based on the limited list of genes that need to be investigated for each patient.

In a first aspect, expression levels of the genes of Table 1 or 9 are determined in the tumor and normal samples. The expression levels are determined by measuring mRNA level. The determination of the expression level variation for these mRNA is carried out by comparing the expression levels in a tumor tissue and in the corresponding normal tissue. The gene expression analysis allows the study of independent deregulations or deregulations due to chromosomal aberrations. Indeed, the regulation of the transformational activity of genes is complex and involves many levels of regulation: trans/cis transcription factors, promoters, chromatin regulation, and the like. Generally, all deregulations (over-expression) are considered with a ratio tumor/normal of at least 1.3. For each deregulated gene (i.e., gene with a different mRNA expression when tumor and normal samples are compared), a fold change and/or intensity of signal (proportional to the mRNA expression level) is determined.

Technologies that can be used comprise Northern analysis, mRNA or cDNA microarrays, RT-PCT (in particular quantitative RT-PCR) and the like. Alternatively, the level of expression can be determined with a chip comprising a set of primers or probes specific for the list of genes of Table 1 or 9 or a set specific genes of a subgroup of 10, 12, 14, 16 or 18 intervention points as disclosed in Table 1 or 9. Expression levels obtained from cancer and normal samples may be normalized by using expression levels of proteins which are known to have stable expression such as RPLPO (acidic ribosomal phosphoprotein PO), TBP (TATA box binding protein), GAPDH (glyceraldehyde 3-phosphate dehydrogenase) or I3-actin.

It is important to note that the method according to the present invention is clearly distinct from a method of global or whole analysis of gene expression. Even if some genes can be added to the list of genes of Table 1 or 9, the gene expression is determined for less than 200, 250, or 300 genes.

In a second aspect, some genes of the list of genes of Table 1 and 9 are analyzed by sequencing (partial or whole sequencing) or by hybridization for detecting the presence or absence of mutations. For instance, exons of the genes of Table 1 or 9 can be sequenced by any method available, preferably by a method of high throughput sequencing such as Illumina or Ion Torrent method or equivalent. Alternatively, only genes with known activating mutation(s) can be analyzed. Such list of genes and mutations can change depending on the considered cancer. In a particular embodiment, the genes of Table 10 can be analyzed for the presence of mutations. More preferably, the method includes the sequencing of p53, the most frequent mutated gene in solid tumors. For instance, the method may include the determination of the presence/absence of mutations in the genes p53, KRAS or NRAS (preferably KRAS), EGFR, EBBR2, PIK3CA and BRAF. Indeed, the presence of mutation leading to a functional gain or loss has an important effect on biology of the tumour without being always connected to variations of gene expression or of gene copy number. Many mutations are known to have a direct effect on the activity of a treatment by inducing increased sensitivities or resistances. For example, the mutations in the tyrosine kinase domain of EGFR are often associated with sensitivity to the small molecules inhibiting EGFR, the mutations in KRAS gene are associated with resistance to the treatment by monoclonal antibodies targeting EGFR. The mutational status can be determined by any method known in the art, for instance by sequencing, microsequencing or hybridization. In addition, the gene mutations are listed at sanger.ac.uk/genetics/CGP/cosmic/.

In a third aspect, the copy number variation of genes is defined for the tumor sample of the subject. This analysis can be carried out by CGH (Comparative Genomic Hybridization) which makes it possible to compare the tumor DNA with the normal DNA of the same individual to detect chromosomal aberrations, i.e. copy number variation such as chromosomal losses or gains. This technology is well-known by the man skilled in the art. As an illustration of this knowledge, the following reviews or reference books can be cited: Davies et al. (2005, *Chromosome Research*, 13, 237-248). This technology is useful to identify translocations. It can be easily carried out with frozen biopsies or tumor paraffin-included material. CGH results are expressed as the ratios of copy numbers in the tumor material and in normal tissue. A threshold of 0.5 is been acknowledged to describe a gain or a loss. The higher this ratio, the more important the amplitude of the anomaly. Thus, an important anomaly is likely to have a real impact at the biological level. In a preferred embodiment, a fold change of the copy number variation is determined.

In a fourth aspect, levels of miRNAs or microRNAs for the genes of Table 1 or 9 are determined in the tumor and normal samples. More preferably, the levels of 5 miRNAs for each gene are determined. In a preferred embodiment, the miRNAs of Table 11 are analyzed. The method for measuring miRNA is well-known in the art.

Then, a fold change Tumor versus Normal tissue is determined for the 5 miRNAs and a mean fold change for each gene is calculated as the average of the fold changes of the 5 miRNAs.

Then, after the characterization step, the following parameters for the tumor of each specific patient have been determined:

A list of genes among the list of Table 1 or 9 with a deregulated expression with a defined fold-change.

A list of mutated genes.

Optionally, a list of genes having a Copy Number Variation and a value (fold-change) for this CNV. In a preferred embodiment, only the genes presenting an amplification are taken into consideration.

Optionally, a list of deregulated miRNA, in particular with an averaged fold change based on the 5 miRNA fold-change.

In a first embodiment, the characterization method includes the gene expression analysis and the mutated genes. In a second embodiment, the characterization method includes the gene expression analysis, the mutated genes and the Copy Number Variation. In a third embodiment, the characterization method includes the gene expression analysis, the mutated genes and the miRNA analysis. In a fourth embodiment, the characterization method includes the gene expression analysis, the mutated genes, the Copy Number Variation and the miRNA analysis. The choice of the combination of criteria can be different for each intervention point.

For instance, for some intervention points, the impact of miRNA has a major influence whereas for other intervention points, miRNA has a minor influence. As shown in the example section, for patients having NSCLC, miRNAs have a major impact on the intervention points mTOR-AKT-PTEN, RAS, ERK, P13K and Immune Modulators, whereas the impact is minor for the intervention points HER CDK4, 6, Angiogenesis, MET, MEK, FGFR, RAF, IGF-Warburg, and PARP. In addition, for patients having NSCLC, the impact of CNV has been determined as quite low.

From these parameters, the method comprises that determination of the disturbed or activated intervention points in the tumor of the patient and the ranking of them by calculating a score for each intervention point.

Mathematical Modeling/Algorithm

The principles of the algorithm for calculating a score for each intervention point are the following:

1—The score is designed to correlate with the likelihood that an intervention point is (abnormally) activated or disturbed in the tumor, in particular in comparison to the normal matched tissue of the same patient. It ranges from 1 to 20, the higher the score, the more activated or disturbed is the pathway. In a preferred embodiment, the score ranges from 1 to 10. However, the scale of the score has no impact on the results.

2—The score may combine evidence from 4 data sources:
Mutations;
Mean fold change in gene differently expressed in the tumor vs. normal;
Optionally, Mean fold change in expression of miRNA of tumor vs. normal; and,
Optionally, Copy number variation.

Activating Mutation and the Score Calculation

The different data sources may carry different weights in the score. Indeed, the activating mutation (e.g. K-RAS in the RAS pathway) may have decisive weight.

Then, in a first approach of the method, the maximal score is given to each intervention point comprising a gene with an activating mutation. In a preferred embodiment, the mutations associated with a maximal score are listed in Table 10. It may further include the p53 mutations. For instance, if the score ranges from 0 to 10, the maximal score of 10 is given to every intervention point comprising a gene with an activating mutation. In the absence of a mutation, the score is based on an average of the mRNA mean fold changes, optionally weighted with the level of expression of miRNAs and to a lesser extent CNV abnormalities.

In a second approach, the rules of the first approach are carried out, but the score is the sum of two scores, a first one based on mutation and a second one based on the arithmetic mean of the mRNA mean fold changes. Preferably, the range/scale of the two scores is the same. For instance, the two scores each range from 0 to 10.

In a third approach, the score is the sum of two scores, a first one based on mutation and a second one based on the mRNA mean fold change. However, a different weight/score can be given to mutations. In particular, instead of giving a score of 10 as soon as an activating mutation is detected, a lower score can be given to the activating mutation, for instance a score of 3. Accordingly, one mutation in a gene of an intervention point gives a score of 3, two mutations a score of 6, three mutations a score of 9, more mutations the maximal score of 10. In addition, depending on the impact of the activating mutations, a different weight can be given. For instance, an activating mutation of KRAS gives a score of 10, whereas a mutation with less functional impact will count for 3. Accordingly, mutations listed in Table 10 may have a higher weight, for instance may count 10.

Calculating the Mean Fold-Change of Differentially Expressed Genes:

The global expression pattern is used to calculate a fold-change (f) of the expression of a gene i in the tumor and in the matched normal tissue. This fold change can be referred to as mRNA TvN fold change. It is calculated as the ratio of the expression of a gene in the tumor to the expression of the gene in a normal tissue.

For calculating the mean/average fold change of intervention point k, denoted as $E_k$, the fold changes of differentially expressed genes with a fold change of at least 1.3 are used. In other words, for each intervention point, an average fold-change of the genes i of the intervention point k is calculated, trimming values with a threshold of ≤1.3.

Formally, $E_k$ is calculated as the following: let $M_k$ denote the set of genes that belong to intervention point k, and $m_k$ denote the subset of $M_k$ that includes only differential expressed genes with an absolute fold change ≥1.3. $E_k$ is the average of the fold change of the genes $m_k$.

$$m_k = \{t | t \in M_k \text{ and } |F_t| > 1.3\}$$

The mean expression level is calculated for all the genes in $m_k$:

$$\overline{E}_k = \overline{F}_t \text{ wherein } i \in m_k.$$

In other words, the fold change for a particular intervention point is the average or arithmetic mean of the fold changes of genes belonging to the intervention point as defined in Table 1 or 9 and having a fold change T vs N of 1.3 or more.

In particular, in order to compare the fold changes of different intervention points, a relative scoring, e.g., from 1 to 10, is generated based on the percentile calculation.

Combining mRNA and miRNA Measurements

To adjust for possible miRNA intervention in translation, the inventor proposes to penalize discordance between miRNA and its target mRNA. For each of the genes of Table 1 or 9 that belong to the intervention points or a set thereof, the inventor determined the miRNAs most likely to be involved in their regulation using Target scan (see World-wide Website: targetscan.org/), selecting the top 5 miRNAs for each gene. Table 11 provides a list of the top 5 miRNAs for the genes of Table 1 or 9.

For each gene i, a mean miRNA fold-change can be calculated, which is denoted $A_i$, by averaging the fold changes of the 5 miRNAs (or less if less than 5 miRNAs are identified) that are most likely to target gene i. Then, for each gene, a mean miRNA TvN fold change is determined.

Then, a corrected fold change of a gene of an intervention point is calculated by dividing the mRNA fold change Tumor versus Normal of the gene (mRNA TvN fold change) by the mean fold change for the miRNAs of the gene (mean miRNA TvN fold change). The corrected fold change of a gene is then used to calculate the fold change for a particular pathway by using it in the calculation of the average fold changes of the genes belonging to the pathway as defined in Table 1 or 9 and having a fold change T vs N of 1.3 or more. Based on the corrected fold change of pathways, a corrected score, e.g., a score 1 to 10 is generated based on percentiles.

Combining mRNA and CNV Measurements

Only genes with amplification are taken into account. Preferably, genes with 2-fold or higher amplification are considered as amplified. Then, a corrected fold change of a gene of an intervention point is calculated by multiplying the mRNA fold change Tumor versus Normal of the gene (mRNA TvN fold change) by the CNV fold change of the gene. The corrected fold change of a gene is then used to calculate the fold change for a particular intervention point by using it in the calculation of the average fold changes of the genes belonging to the intervention point as defined in Table 1 or 9 and having a fold change T vs N of 1.3 or more. Based on the corrected fold change of pathways, a corrected score, e.g., a score 1 to 10 is generated based on percentiles.

Score Calculation

To compare intervention points, a score is given to each intervention point, taking into account mRNA expression and activating mutation. Optionally, 3 or 4 variables can be considered: activating mutations, the Fold change of mRNAs in Tumor vs. Normal, the fold change of miRNAs in Tumor vs. Normal and the copy number variation (amplifications, deletions). In a preferred embodiment, the score is given to each intervention point, taking into account activating mutations, mRNA expression, and miRNA expression. In a particular embodiment, the miRNA is considered when calculating the score at least for the following intervention points: mTOR-AKT-PTEN, RAS, ERK, PI3K and Immune Modulators.

To summarize, in a first aspect, the score for each pathway is calculated as follows:

1—If an activating mutation is detected in one gene of the intervention point, then the score of the intervention point is the maximal score, e.g. 10 when scoring from 1 to 10.
2—Otherwise, the score is calculated based on the average of the fold changes tumor vs normal of the genes having an absolute fold change of at least 1.3 and belonging to the list of genes of Table 1 or 9 for the considered intervention point.
3—Optionally, if the miRNA level of the genes of Table 1 or 9 is measured, in particular those of Table 11, a mean miRNA fold change for each gene is calculated as the arithmetic mean of the fold change of 5 miRNAs of this gene. Then a corrected mRNA fold change for the gene is calculated by dividing the mRNA fold change Tumor versus Normal of the gene (mRNA TvN fold change) by the mean fold change for the miRNAs of the gene (mean miRNA TvN fold change). For calculating the mean of the mRNA tumor vs normal fold changes of the genes of an intervention point, the corrected mRNA TvN fold change for the gene is used.
4—Optionally, if the CNV of the genes of Table 1 or 9 (or some genes thereof) is measured with 2-fold or higher amplification, then a corrected mRNA fold change for the gene is calculated by multiplying the mRNA fold change Tumor versus Normal of the gene (mRNA TvN fold change) by the CNV fold change for the gene. For calculating the mean of the mRNA tumor vs normal fold changes of the genes of an intervention point, the corrected mRNA TvN fold change for the gene is used.

Alternatively, it can also be chosen to attribute less weight to mutations, in particular when considering the sequencing of all genes of Table 1 or 9. Accordingly, in a first alternative, the score is the sum of the score due to mutational status and the score due to the mRNA differential TvN expression. In a second alternative, in order to graduate the impact of the mutations, a score of 3 is given by activating mutation. Then, for instance, the score of a pathway is a score based on activating mutations with a maximal score of 10 added to a score based on mRNA expression is calculated above with a maximal score of 10. Accordingly, for each intervention point, the score will be comprised between 0 and 20.

Based on the scores of the intervention points, the intervention points are ranked. The pathway ranking can allow the one skilled in the art to select one or several combinations of three activated or disturbed intervention points, especially the combination of the three most activated or disturbed intervention points according to the scores.

The pathways have been selected because drugs specific to each intervention point are already or soon available for treating a patient (see Table 1). Accordingly, based on the combination of selected intervention points, a combination of drugs targeting these intervention points can be selected and proposed for treating the patient.

Therefore, the present invention relates to a method for selecting a combination of three drugs useful for treating a patient having a cancer, wherein a group of three activated or disturbed intervention points are selected by the method of the present invention and a drug is selected for each activated or disturbed intervention point, thereby providing a combination of three drugs.

Prior to any administration to a patient, the efficacy of the drugs combination can be tested ex vivo. For instance, the combination can be tested on a model based on a biopsy of the tumor from the patient. It can be tested on an animal model on which tumor cells from the tumor has been grafted. Alternatively, it can be tested in a pre-clinical model called Metastatic Ex Vivo Assay (MEVA). It is an in vitro 3D tissue culture through an anchorage independent system.

Then, the present invention relates to a method of treatment of a patient having a cancer or a method for selecting a combination of drugs for treating a patient having a cancer, comprising:

Providing a tumor sample and an histologically matched normal tissue from the patient;
Characterizing the tumor sample in comparison to the normal sample as detailed above;
Calculating a score for each intervention point as detailed above;
Selecting three activated or disturbed intervention points, preferably the three most activated or disturbed intervention points;
Selecting a combination of drugs targeting the three selected activated or disturbed intervention points;
Optionally, administrating to the patient the selected combination of drugs.

Optionally, the method of the present invention can provide several combinations of three drugs. Indeed, in order to prevent any drug resistance, the combinations can be used sequentially.

In addition, the present invention relates to a kit and the use of such a kit for classifying intervention points according to their status and for selecting a combination of three drugs chosen as targeting the most activated or disturbed intervention points, wherein the kit comprises means for measuring the mRNA expression level of the genes of Table 1 or 9. In particular, such means can be primers and/or probes specific for each gene of Table 1 or 9.

Optionally, the kit may further comprise means for detecting the mutations in genes of Table 1 or 9. These means could be suitable for the whole sequencing of the genes of Table 1 or 9. More preferably, the kit comprises means for detecting the mutations of Table 10. Means can be probes specific of the nucleic acid sequence encoding a fragment including the mutation. They can also be primers allowing the amplification and sequencing of the genes.

Optionally, the kit may further comprise means for determining the level of miRNA of genes of Table 1 or 9, in particular those of Table 11. Finally, the kit may further comprise means for determining the copy number variation of the genes of Table 1 or 9.

Finally, the present invention relates to drug combinations of interest identified by the method of the present invention. In a particular embodiment, the present invention relates to a drug combination including one drug targeting PDL1 or CTLA4 and two drugs selected from the group consisting of an inhibitor of RAF, an inhibitor of Angiogenesis, an inhibitor of MEK; an inhibitor of MET and an inhibitor of CDK 4,6.

The main reason to define triple regiment therapies as a combination of an immunomodulator (anti PD1L or anti CTLA4) and two targeted therapies is to contain toxicity of associations. Indeed, the main problem of combining targeted therapies might be the additive toxicity. Whilst containing toxicity of a dual combination was already demonstrated, adding a third drug such as anti PD1L may contribute to an effective tolerated therapy, in particular for metastatic NSCLC.

Accordingly, the present invention relates to a drug combination for use in the treatment of cancer, wherein the drug combination is selected among the combinations disclosed in Table 6, Table 7, Table 8.

Preferably, the drug combination is the combination of three drugs. Optionally, it may include additional drugs.

In a more specific embodiment, the present invention relates to a drug combination including a drug targeting PDL1, an inhibitor of RAF and a third targeted drug such as an inhibitor of MEK6, an inhibitor of MET, an inhibitor of CDK4,6 or an inhibitor of angiogenesis.

Based on analysis of frequency of occurrence of activated interventional points, and based on analysis of trends of co-activation, the most important combinations are the following:

1. anti PD1L (e.g., AZ)+Pan RAF inhibitor (e.g., Takeda)*+MtorP13K inhibitor (e.g., Pfizer),
2. anti PD1L (e.g., AZ)+Pan RAF inhibitor (e.g., Takeda)*+angio-inhibitor (e.g., Pfizer),
3. anti PD1L (e.g., AZ)+Pan RAF inhibitor (e.g., Takeda)*+met inhibitor (e.g., Pfizer),
4. anti PD1L (e.g., AZ)+Pan RAF inhibitor (e.g., Takeda)*+CDK4,6 inhibitor (e.g., Pfizer), these four combinations covers 51% of patients with NSCLC as determined in the analysis of the retrospective collection of 123 patients.

In addition to these 4 combinations, the inventor determined that replacing PD1L with CTL14 fulfils the criteria of combining an immunomodulator with two other targeted drugs. Four additional combinations can be envisioned, increasing the coverage of patients to 72%:

5. anti CTLA4 (e.g., AZ)+Pan RAF inhibitor (e.g., Takeda)*+MtorP13K inhibitor (e.g., Pfizer),
6. anti CTLA4 (e.g., AZ)+Pan RAF inhibitor (e.g., Takeda)*+angio-inhibitor (e.g., Pfizer),
7. anti CTLA4 (e.g., AZ)+Pan RAF inhibitor (e.g., Takeda)*+met inhibitor (e.g., Pfizer),
8. anti CTLA4 (e.g., AZ)+Pan RAF inhibitor (e.g., Takeda)*+CDK4,6 inhibitor (e.g., Pfizer).

It is worthwhile to mention that the Pan RAF inhibitor could be replaced with a MEK inhibitor in most of the patients. This replacement generates 8 combinations:

9. anti PD1L (e.g., AZ)+MEK inhibitor+MtorP13K dual inhibitor (e.g., Pfizer),
10. anti PD1L (e.g., AZ)+MEK inhibitor+angio-inhibitor (e.g., Pfizer or Takeda),
11. anti PD1L (e.g., AZ)+MEK inhibitor+met inhibitor (e.g., Pfizer),
12. anti PD1L (e.g., AZ)+MEK inhibitor+CDK-6 inhibitor (e.g., Pfizer),
13. anti CTLA4 (e.g., AZ)+MEK inhibitor+MtorP13K dual inhibitor (e.g., Pfizer),
14. anti CTLA4 (e.g., AZ)+MEK inhibitor+metinhibitor (e.g., Pfizer),
15. anti CTLA4 (e.g., AZ)+MEK inhibitor+angio_inhibitor (e.g., Pfizer or Takeda),
16. anti CTLA4 (e.g., AZ)+MEK inhibitor+CDK4,6 inhibitor (e.g., Pfizer).

In a preferred embodiment, the above-mentioned drugs can be selected among those disclosed in Table 1.

More preferably, the drug combination is selected from the group consisting of:

Medi-4736 (Astra Zeneca)+MLN2480 (Takeda)+PF-384 (Pfizer),
Medi-4736 (Astra Zeneca)+MLN2480 (Takeda)+Axitinib (Pfizer) or Motesanib (Takeda),
Medi-4736 (Astra Zeneca)+MLN2480 (Takeda)+Crizotinib (Pfizer),
Medi-4736 (Astra Zeneca)+MLN2480 (Takeda)+Palbociclib (Pfizer),
Tremelimumab (Astra Zeneca)+MLN2480 (Takeda)+PF-384 (Pfizer),
Tremelimumab (Astra Zeneca)+MLN2480 (Takeda)+Axitinib (Pfizer) or Motesanib (Takeda),
Tremelimumab (Astra Zeneca)+MLN2480 (Takeda)+Crizotinib (Pfizer),
Tremelimumab (Astra Zeneca)+MLN2480 (Takeda)+Palbociclib (Pfizer),
Medi-4736 (Astra Zeneca)+Selumetinib (Astra Zeneca)+PF-384 (Pfizer),
Medi-4736 (Astra Zeneca)+Selumetinib (Astra Zeneca)+Axitinib (Pfizer) or Motesanib (Takeda),
Medi-4736 (Astra Zeneca)+Selumetinib (Astra Zeneca)+Crizotinib (Pfizer),
Medi-4736 (Astra Zeneca)+Selumetinib (Astra Zeneca)+Palbociclib (Pfizer),
Tremelimumab (Astra Zeneca)+Selumetinib (Astra Zeneca)+PF-384 (Pfizer),
Tremelimumab (Astra Zeneca)+Selumetinib (Astra Zeneca)+Crizotinib (Pfizer),
Tremelimumab (Astra Zeneca)+Selumetinib (Astra Zeneca)+Axitinib (Pfizer) or Motesanib (Takeda), and
Tremelimumab (Astra Zeneca)+Selumetinib v+Palbociclib (Pfizer).

By a "drug combination", it is referred to a pharmaceutical composition comprising the drugs of the combination or to a kit or product comprising the drugs of the combination as a combined preparation for simultaneous, separate or sequential use.

The present invention relates to a pharmaceutical composition comprising the drugs of the combination, and a pharmaceutically acceptable carrier, in particular for use in the treatment of cancer; and/or a product or kit containing the drugs of the combination, as a combined preparation for simultaneous, separate or sequential use, in particular in the treatment of cancer; and/or a combined preparation which comprises the drugs of the combination, for simultaneous, separate or sequential use, in particular in the treatment of cancer; and/or a pharmaceutical composition comprising the drugs of the combination for the use in the treatment of cancer in combination with radiotherapy and/or an additional anti-tumoral agent; and/or the use of a pharmaceutical composition comprising the drugs of the combination for the manufacture of a medicament for the treatment of cancer; and/or the use of a pharmaceutical composition comprising the drugs of the combination for the manufacture of a medicament for the treatment of cancer in combination with radiotherapy, and/or or an additional anti-tumoral agent; and/or a method for treating a cancer in a subject in need thereof, comprising administering an effective amount of a pharmaceutical composition comprising the drugs of the combination, and a pharmaceutically acceptable carrier; and/or a method for treating a cancer in a subject in need thereof, comprising administering an effective amount of the drugs of the combination; and/or a method for treating a cancer in a subject in need thereof, comprising administering an effective amount of a pharmaceutical composition comprising the drugs of the combination in combination with radiotherapy.

In a preferred embodiment, the cancer is a lung cancer, and more preferably a NSCLC.

The following describes material, methods and results presenting a full investigation of possibilities of combinations, based on magnitude and frequency of occurrence of interventional points of activation as determined by the scoring system. In addition, selection of combinations takes into account the trends of co-activation.

EXAMPLES

Methods

Patients and Tissue Samples

The present study was organized by the CHEMORES initiative (Chemotherapy resistance consortium), which is an EU funded (FP6) Integrated Project involving 19 academic centres, organizations for cancer research, and research-oriented biotechnology companies in 8 European countries.

Tissue samples from a cohort of 123 patients who underwent complete surgical resection at the Institut Mutualiste Montsouris (Paris, France) between 30 Jan. 2002 and 26 Jun. 2006 were analyzed. Clinical characteristics are given in Table 4 below. The median age of patients was 63 years (range 41-85), 34 (28%) were female and 89 (72%) were male. The histopathology of all tumors was reviewed by the same pathologist (JvdO): 50 patients had SCC, 57 AC, 13 LCC and 3 unclassified. Using the new 7th edition TNM staging 56 were stage I, 25 stage II, 28 stage III and 4 stage IV. Adjuvant platinum based chemotherapy was administered to 61 patients. Fifty-nine patients experienced a relapse. Two-year relapse-free survival was 64%, and the median time to recurrence for the cohort was 5.2 years. After a median follow up of 40 months (range 0-92) 36 patients had died and 23 patients were alive with recurrence.

This study was performed using snap-frozen tumor and adjacent normal lung tissue. Samples were handled according to the Tumor Analysis Best Practices Working Group (Nat Rev Genet 2004; 5:229-237). Haematoxylin and eosin stained frozen sections, taken before and after the cutting of slides for analysis, revealed a median cell content of 85% (an inter-quartile range of 65% to 95%). All tissues were banked after written informed patient consent, and the study was approved by the Ethics Committee of Institut Gustave Roussy (IGR). Genomic investigations were performed at IGR, leader of the Genomic work-package of Chemores consortium, in the genomic center core facility certified ISO9001, labelled European reference and training center for Agilent technologies. Analyses were performed at IGR and Karolinska Institute, the leader of integrated analyzes work-package.

TABLE 2

Characteristics of the patients in the study population

| | n = 123 (100%) |
|---|---|
| Age median (range) | 63 (40.9-84.6) |
| Males n (%) | 89 (72%) |
| Smoking Current | 64 (52%) |
| Former | 51 (42%) |
| Never | 7 (6%) |
| Histology AC | 57 (46%) |
| SCC | 50 (41%) |
| LCC | 13 (11%) |
| Other | 3 (3%) |
| Stage 1 | 56 (50%) |
| 2 | 25 (22%) |
| 3 | 28 (25%) |
| 4 | 4 (4%) |
| Adjuvant Chemo (%) | 61 (50%) |

Data Availability

The microarray data related to this study have been submitted to the Array Express data repository at the European Bioinformatics Institute (see Worldwide Website: ebi.ac.uk/arrayexpress/) under the accession numbers E-MTAB-1132 (GE), E-MTAB-1133 (CGH) and E-MTAB-1134 (MIR).

Oligonucleotide aCGH

DNA samples were extracted from tissues using Qiagen QIAamp DNA Mini kit (Qiagen, Hilden, Germany). In each case, the normal tissue sample was used as the reference to its corresponding tumor sample. DNA was restriction digested and controlled by Agilent Bioanalyzer on DNA 7500 chips (Agilent Technologies, Santa Clara, Calif., USA). The fragmented reference and test DNA were labelled with Cy3-dUTP or Cy5-dUTP, respectively, using Agilent Genomic DNA Labelling Kit PLUS. Samples were purified using Microcon YM-30 filters (Millipore, Billerica, Mass.). Hybridization was carried out on Agilent 244K arrays for 24 hours at 65° C. in a rotating oven (Robbins Scientific, Mountain View, Calif.) at 20 rpm, followed by appropriate washing steps. Scanning was performed with an Agilent G2505C DNA Microarray scanner using default parameters. Quantification of Cy5 and Cy3 signals from scans was performed with Feature Extraction v10.5.1.1 (Agilent Technologies) using default parameters.

CGH Data Processing and Analysis

Resulting raw signals and log 2 (ratio) profiles were normalized and centered according to their dye composition (Cy5/Cy3) and local GC content. These profiles were segmented with the Circular Binary Segmentation algorithm (Olshen et al. Biostatistics 2004 October; 5(4):557-72) through its implementation in the DNAcopy package for R v2.8.1 using default parameters. DNA copy number imbalances were detected considering a minimum of 3 consecutive probes and a minimal absolute amplitude threshold that was specific for each profile, accordingly with its internal noise. This specific internal noise was computed as one-fourth of the median of the absolute log 2 (ratio) distances across consecutive probes on the genome. Of the 128 aCGH hybridizations performed, 17 were discarded: 7 due to their clinical annotations, 2 due to anomalies in their normal reference, and 8 due to the bad quality of their profile, resulting in 111 usable profiles. All aCGH coordinates in this study are mapped against the human genome as defined by the UCSC build hg18.

To assess the discovery of the genomic regions with differential anomalies between the AC, LCC and SCC populations, ANOVA tests were performed on the segmented aCGH dataset. To account for multiple testing, p-values were transformed to false discovery rate (FDR) (Benjamini et al. J Royal Statist Soc B 1995; 57:289-300).

Gene Expression and microRNA Microarray Assay

The lysis of 40 to 50 frozen sections of 10 micron-thickness, cut from each NSCLC tissue sample was done using a Polytron homogenizer (Ultraturrax, IMLAB, Lille, France). The RNA extraction was performed with TRIzol® Reagent protocol (Invitrogen, Carlsbad, Calif., USA). Total RNA was quantified and qualified with Nanodrop ND-1000 spectrometer and Bioanalyzer-2100 (Agilent Technologies).

For dual color Cy3 (normal samples) and Cy5 (tumor samples) labelling, Agilent Fluorescent Low Input Linear Amplification kit adapted for small amounts of total RNA (500 ng total RNA per reaction) was used, followed by purification of labelled probes by Qiagen RNeasy Mini kit and by a protocol provided by Agilent. Gene expression profiling was performed with dye-swap, using dual-color 244K Human exon array from Agilent (custom design with the content of the 44K Human genome plus 195000 probes, one for each exon as defined in refGene list of UCSC build hg18 (http://genome.ucsc.edu/)). Hybridization was carried out for 17 hours at 65° C. at 10 rpm, followed by washing steps. Scanned microarray images were analyzed by using Feature Extraction software version 10.5.1.1 (Agilent).

For the microRNA analysis, normal and tumor samples were hybridized on separate arrays. Agilent miRNA Microarray System with miRNA complete labelling and hybridization kit was used for Cy3 labelling. Briefly, isolated total RNAs were dephosphorylated, labelled with pCp-Cy3 and hybridized to Agilent 8x15K arrays for 20h at 55° C. in a rotating oven (Robbins Scientific) at 20 rpm. Slides were washed and scanned for gene expression using an Agilent G2565C DNA microarray scanner using defaults parameters.

Gene Mutations Analysis

Sequencing was performed at IGR and at the Royal Institute of Technology (Stockholm, Sweden). DNA was extracted with QIAamp DNA Mini Kit (Qiagen, Hilden, Germany). After PCR amplification of target exons, sequencing reactions were carried out using the BigDye® Terminator Cycle Sequencing Kit (Applied Biosystems, Forster City, Calif.). The primer sequences are available on request. Sequencing reactions were run on a 48-capillary 3730 DNA Analyzer®. Sequence analysis and alignment was performed with SeqScape® software (Applied Biosystems). All detected mutations were confirmed in at least one independent PCR reaction. In all 123 samples, full coding sequences of exons including oncogenic mutational hotspots were analyzed corresponding to: TP53 (NM_000546.4) exons 5-8; KRAS (NM_004448.2) exons 2 and 3; EGFR (NM_005228.3) exons 18-21; PIK3CA (NM_006218.2) exons 10 and 21; BRAF (NM_004333.4) exon 15; ERBB2 (NM_004448.2) exons 18, 20-24; KDR (NM_002253.1) exons 2, 26, 27 and 30; and AKT1 (NM_005163.2) exon 4.

Gene-Expression Data Processing and Normalization

All processing methods used for gene expression analysis were performed on the median signal from Agilent Feature Extraction raw data files using functions and packages collected in the R Bioconductor project (Gentleman et al. Genome Biology, 5: R80) as well as custom written routines.

For gene expression data, dye-swap arrays were first combined (by taking the average of intensities) to obtained only one array per condition. This combination has the result of centering the M values (log 2 ratios) on zero. Then, flagged spots as well as control spot were removed. Normalization was then performed using the normalize WithinArrays function from R package LIMMA (Smyth G K *Statistical Applications in Genetics and Molecular Biology* 2004, vo13: No 1, article 3).

For miRNA data, control spots were systematically removed, and flagged spots (glsFeatNonUnifOL and glsSaturated columns from raw files) were considered as missing values ("NA"). Array normalization was performed using the least-variant-set method (Suo et al. RNA 2010 December; 16(12): 2293-303).

Differential Expression Analyses of miRNA Expression

To assess differentially-expressed miRNA, the inventor first estimated the fold changes and standard errors between two groups of samples by fitting a linear model for each probe with the lmFit function of LIMMA package in R. An emperical Bayes smoothing was applied to the standard errors from the linear model previously computed with eBayes function.

Scoring/Ranking of Activated Interventional Points

The Algorithm

The mathematical modelling and scoring system aims to give a score (1 to 10) based on integration of omics data, sequencing, gene expression, miRNA and copy number variations determined as differences between tumor and normal, individually for each patient. SPRING scoring enables identification and ranking of activated pathways, and the overall concept is that such activated pathways should be blocked with combined targeted therapies.

Figure 2:
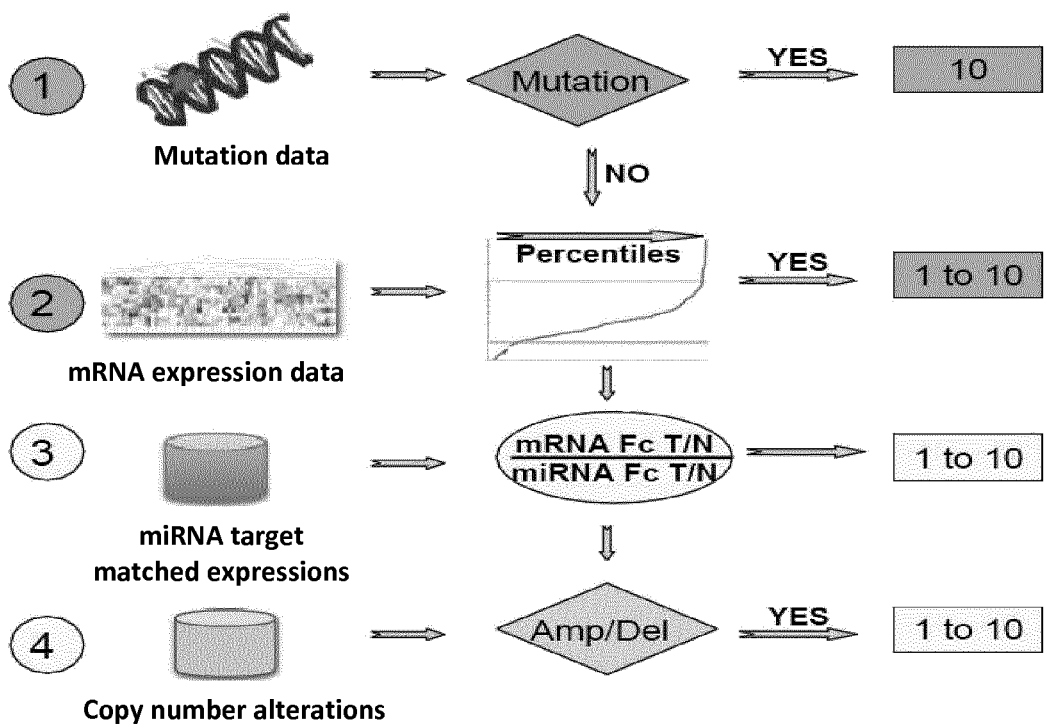
FIG. 2. Flowchart of the scoring system.
Figure 3:
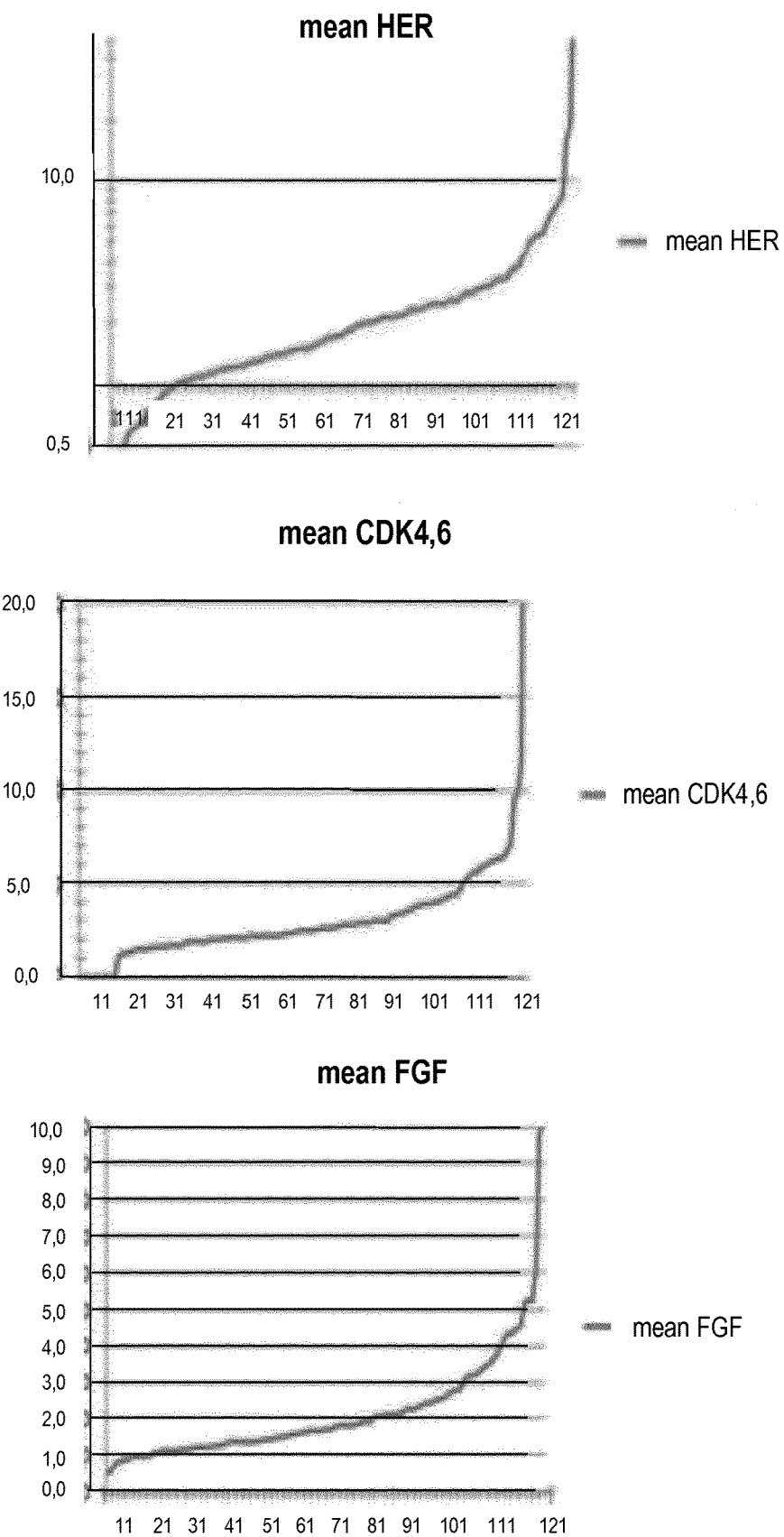
FIG. 3. In Y: Mean fold change of differential gene expression between T and N in each patient. In X: number of patients NB: for each graph, the order of patients is different. This series serve as calibrator for calculation of deciles.
Figure 4:
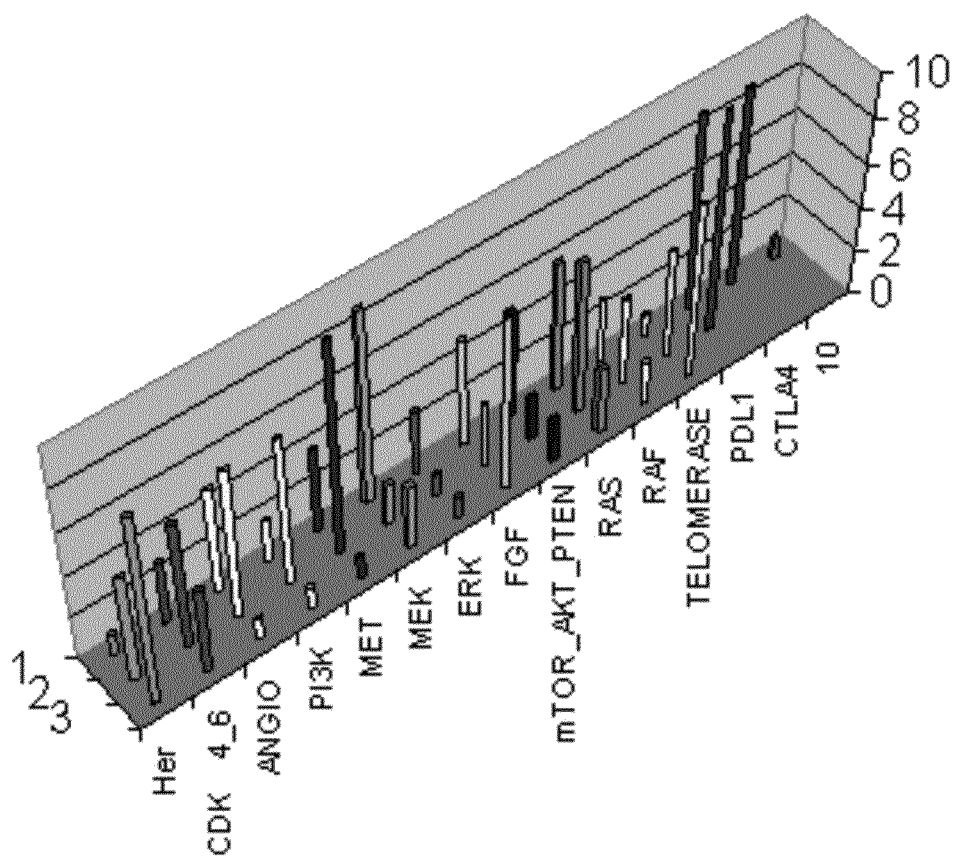
FIG. 4. Representation 3D of the scoring system. Axis Z shows score from 1 to 10. Axis X represents an example of interventional points, axis y represents each patient.

The first mathematical model was established on the basis of a retrospective dataset from 123 patients with NSCLC for whom sequencing, Copy Number Variation, and tumor vs. normal gene expression were available. Using these data, an algorithm that provides a score of activation for each of the simplified pathways for the patient and factors in all of the above-mentioned structural and functional results has been established. The principle of the algorithm is disclosed in FIG. 2.

Scoring is based on an intuitive algorithm that integrates 4 types of genomic investigations of Tumor and Normal biopsies 1. Mutations: in V.1 the inventor used a very limited set of sequencing data, including only the genes/mutations used currently in clinical care of NSCLC: EGFr, kRAS, BRAF, PI3KCA, and HER2. Additionally p53 was sequenced, which is the frequently mutated gene in lung (and all solid tumors).
    a. When a mutation is detected, the algorithm assigns the maximal score 10 in the corresponding simplified pathway.
2. Gene Expression: For each simplified pathway, mRNA steady state level in Tumor vs. Normal is used to calculate a mean fold change of the pathway.
    a. Values of individual Fold Change are trimmed at the threshold 1.3.
    b. Values of individual mean fold changes for each simplified pathway are ranked in the retrospective set of data of 123 NSCLC, used as a calibrator.
    c. As shown in the 3 examples below, the range of Fold Changes is different from one to the other pathway. In order to compare them, the inventor generated a relative scoring from 1 to 10 based on the percentile calculation.
3. miRNA expression: For each gene, the inventor selected the top 5 matched miRNA from TargetScan data base.
    a. The fold changes T vs. N steady state level for each miRNA was used to generate a mean fold change.
    b. Fold change T vs. N for each gene was divided by the mean Fc T/N of the 5 corresponding miRNAs.
    c. A corrected mean Fold change for each simplified pathway was generated.
    d. A corrected score of 1 to 10, based on percentiles, was generated.

4. Copy Number Variation. When amplification is detected, the inventor multiplied the value of the mRNA expression fold change for each gene by the value of the fold change amplification. The corrected mean fold change of pathways and the percentiles score was generated.

TABLE 3 summarises scores obtained for all patients of the 123 NSCLC, for a selection of interventional points

| patient | Histo | Her | CDK4_6 | ANGIO | PI3K | MET | MEK | ERK | FGF | mTOR | RAS | RAF | PARP | JAK_STAT | PDL1 | CTLA4 |
|---|---|---|---|---|---|---|---|---|---|---|---|---|---|---|---|---|
| AGG600716 | AC | 1 | 3 | 5 | 2 | 4 | 9 | 3 | 5 | 5 | 6 | 3 | 8 | 6 | 9 | 9 |
| ANO420520 | AC | 5 | 6 | 7 | 7 | 10 | 2 | 1 | 3 | 2 | 7 | 4 | 5 | 8 | 10 | 9 |
| ARC270517 | SCC | 9 | 4 | 1 | 1 | 1 | 3 | 1 | 8 | 2 | 3 | 2 | 8 | 2 | 1 | 4 |
| AVI260916 | AC | 2 | 2 | 5 | 7 | 2 | 8 | 9 | 9 | 7 | 10 | 10 | 5 | 8 | 9 | 2 |
| AZE450213 | AC | 8 | 10 | 9 | 4 | 7 | 7 | 5 | 2 | 3 | 2 | 9 | 3 | 9 | 2 | 10 |
| BAR331123 | SCC | 8 | 7 | 10 | 10 | 6 | 4 | 7 | 9 | 8 | 8 | 8 | 7 | 7 | 7 | 10 |
| BAS260512 | AC | 10 | 1 | 3 | 1 | 3 | 5 | 2 | 1 | 4 | 4 | 5 | 6 | 5 | 5 | 3 |
| BAS260724 | AC | 5 | 10 | 8 | 3 | 9 | 6 | 5 | 2 | 1 | 6 | 5 | 4 | 5 | 10 | 8 |
| BEM291129 | SCC | 5 | 1 | 1 | 6 | 5 | 4 | 6 | 6 | 2 | 5 | 4 | 1 | 8 | 5 | 7 |
| BEN480707 | SCC | 1 | 1 | 2 | 4 | 5 | 8 | 4 | 2 | 3 | 9 | 6 | 2 | 7 | 10 | 5 |
| BEN410529 | LCC | 7 | 3 | 9 | 5 | 5 | 7 | 3 | 6 | 2 | 10 | 10 | 5 | 6 | 8 | 8 |
| BER520430 | AC | 7 | 2 | 4 | 2 | 3 | 3 | 4 | 6 | 7 | 7 | 3 | 2 | 1 | 4 | 2 |
| BIE410219 | SCC | 10 | 9 | 7 | 7 | 5 | 7 | 6 | 9 | 7 | 10 | 4 | 9 | 8 | 3 | 8 |
| BOU480910 | AC | 9 | 3 | 6 | 2 | 5 | 8 | 2 | 7 | 5 | 6 | 4 | 3 | 6 | 3 | 6 |
| BOU291129 | SCC | 2 | 9 | 1 | 10 | 9 | 3 | 2 | 5 | 7 | 1 | 1 | 10 | 3 | 4 | 1 |
| BOU520111 | AC | 6 | 5 | 5 | 5 | 6 | 2 | 9 | 8 | 7 | 1 | 6 | 5 | 4 | 6 | 10 |
| BRO521127 | AC | 4 | 8 | 8 | 2 | 7 | 9 | 7 | 1 | 2 | 2 | 5 | 6 | 10 | 6 | 10 |
| BRZ470326 | AC | 10 | 9 | 9 | 8 | 10 | 10 | 5 | 6 | 10 | 2 | 1 | 8 | 7 | 10 | 8 |
| CAM520101 | Other SCLC | 10 | 9 | 6 | 8 | 10 | 9 | 6 | 7 | 4 | 2 | 1 | 1 | 10 | 3 | 7 |
| CAP460215 | LCC | 1 | 4 | 1 | 3 | 10 | 2 | 4 | 2 | 5 | 3 | 10 | 9 | 2 | 2 | 4 |
| CHA280524 | AC | 8 | 5 | 2 | 8 | 9 | 4 | 10 | 1 | 3 | 4 | 5 | 3 | 5 | 1 | 4 |
| CHA571008 | LCC | 8 | 5 | 5 | 1 | 6 | 2 | 6 | 2 | 1 | 3 | 2 | 5 | 3 | 5 | 6 |
| CHA470718 | LCC | 4 | 6 | 10 | 3 | 9 | 7 | 10 | 6 | 10 | 3 | 7 | 2 | 5 | 7 | 9 |
| CHE511225 | AC | 6 | 9 | 1 | 2 | 8 | 6 | 8 | 3 | 9 | 3 | 9 | 10 | 9 | 6 | 7 |
| COU420201 | AC | 2 | 10 | 1 | 10 | 4 | 5 | 10 | 7 | 8 | 6 | 10 | 10 | 1 | 1 | 5 |
| CRE420423 | SCC | 6 | 10 | 10 | 6 | 8 | 6 | 1 | 10 | 10 | 9 | 5 | 4 | 7 | 9 | 9 |
| DAM200413 | SCC | 2 | 10 | 9 | 7 | 2 | 10 | 3 | 3 | 6 | | | | | | |
| DAV320407 | SCC | 1 | 5 | 10 | 2 | 7 | 3 | 5 | 10 | 4 | 2 | 7 | 6 | | 2 | 7 | 7 |
| DEL330821 | AC | 7 | 8 | 7 | 10 | 10 | 9 | 4 | 3 | 9 | 10 | 7 | 4 | 10 | 9 | 10 |
| DEP351121 | SCC | 5 | 9 | 6 | 8 | 6 | 6 | 10 | 8 | 10 | 2 | 6 | 9 | 2 | 4 | 3 |
| DES580418 | AC | 10 | 6 | 3 | 7 | 9 | 7 | 8 | 6 | 8 | 5 | 8 | 10 | 10 | 8 | 7 |
| DEW440406 | AC | 5 | 4 | 6 | 4 | 7 | 3 | 4 | 3 | 3 | 6 | 6 | 2 | 2 | 5 | 5 |
| DHE321214 | Other ADEC | 9 | 6 | 3 | 6 | 10 | 4 | 1 | 9 | 5 | 9 | 10 | 6 | 6 | 5 | 5 |
| DOM590729 | SCC | 3 | 10 | 3 | 9 | 7 | 4 | 10 | 8 | 5 | 8 | 4 | 10 | 4 | 10 | 5 |
| DUV330713 | SCC | 6 | 5 | 10 | 4 | 4 | 8 | 9 | 7 | 9 | 2 | 8 | 10 | 6 | 10 | 4 |
| ECU520713 | AC | 3 | 10 | 8 | 1 | 8 | 2 | 7 | 9 | 10 | 8 | 8 | 3 | 3 | 5 | 1 |
| EDO300812 | SCC | 7 | 5 | 2 | 9 | 8 | 7 | 4 | 3 | 9 | 7 | 5 | 9 | 5 | 4 | 7 |
| ELA540809 | LCC | 4 | 8 | 4 | 1 | 1 | 3 | 2 | 10 | 5 | 9 | 10 | 4 | 3 | 5 | 2 |
| ELB330728 | AC | 10 | 3 | 6 | 7 | 7 | 5 | 3 | 2 | 1 | 7 | 6 | 10 | 7 | 6 | 9 |
| FER471031 | AC | 4 | 2 | 8 | 2 | 4 | 3 | 4 | 3 | 8 | 4 | 6 | 7 | 2 | 7 | 5 |
| FER461230 | SCC | 3 | 5 | 7 | 6 | 5 | 7 | 2 | 6 | 6 | 5 | 5 | 1 | 4 | 3 | 3 |
| FIL381013 | AC | 10 | 10 | 9 | 6 | 7 | 10 | 3 | 1 | 4 | 3 | 10 | 3 | 10 | 10 | 8 |
| FLA490711 | AC | 5 | 5 | 8 | 1 | 2 | 2 | 5 | 5 | 8 | 1 | 1 | 10 | 1 | 3 | 2 |
| FOR440321 | AC | 7 | 6 | 9 | 6 | 10 | 5 | 7 | 4 | 4 | 1 | 8 | 1 | 7 | 4 | 6 |
| FOR410727 | SCC | 6 | 7 | 4 | 10 | 3 | 10 | 6 | 3 | 7 | 6 | 4 | 6 | 8 | 10 | 6 |
| FRO440806 | AC | 2 | 2 | 3 | 5 | 6 | 9 | 8 | 1 | 3 | 6 | 8 | 2 | 3 | 5 | 7 |
| GAN350811 | SCC | 10 | 8 | 4 | 10 | 9 | 6 | 5 | 6 | 6 | 1 | 7 | 8 | 1 | 1 | 3 |
| GAR410813 | SCC | 6 | 7 | 6 | 9 | 6 | 1 | 10 | 5 | 4 | 4 | 1 | 10 | 6 | 8 | 6 |
| GAR450819 | SCC | 10 | 7 | 3 | 8 | 4 | 4 | 4 | 2 | 4 | 2 | 4 | 10 | 7 | 8 | 8 |
| GEF541216 | AC | 10 | 7 | 8 | 10 | 3 | 9 | 4 | 8 | 10 | 9 | 4 | 4 | 5 | 9 | 10 |
| GEO270114 | SCC | 3 | 6 | 2 | 5 | 10 | 5 | 10 | 4 | 1 | 10 | 6 | 7 | 8 | 4 | 7 |
| GID490224 | AC | 7 | 7 | 10 | 3 | 8 | 10 | 1 | 3 | 6 | 10 | 9 | 5 | 5 | 3 | 4 |
| GIL230901 | SCC | 3 | 1 | 2 | 6 | 6 | 6 | 3 | 9 | 7 | 7 | 3 | 6 | 6 | 6 | 6 |
| GIR220606 | AC | 9 | 1 | 3 | 4 | 7 | 4 | 10 | 4 | 4 | 8 | 9 | 2 | 2 | 1 | 3 |
| GOE191205 | AC | 10 | 4 | 7 | 4 | 8 | 1 | 5 | 4 | 2 | 7 | 3 | 3 | 4 | 4 | 2 |
| GOM450227 | SCC | 9 | 4 | 6 | 9 | 7 | 1 | 2 | 10 | 4 | 6 | 3 | | | | |
| GRO250108 | AC | 10 | 9 | 7 | 10 | 6 | 8 | 8 | 4 | 8 | 10 | 10 | 8 | 10 | 8 | 9 |
| GRY470526 | AC | 9 | 6 | 4 | 10 | 9 | 2 | 3 | 2 | 1 | 6 | 7 | 1 | 9 | 2 | 7 |
| GUI390806 | AC | 10 | 7 | 3 | 7 | 3 | 6 | 3 | 10 | 6 | 10 | 10 | 1 | 8 | 2 | 4 |
| GUI200304 | AC | 9 | 2 | 3 | 9 | 9 | 10 | 5 | 10 | 8 | 8 | 10 | 2 | 6 | 2 | 6 |
| HAM640729 | SCC | 3 | 2 | 10 | 5 | 1 | 10 | 10 | 9 | 1 | 9 | 1 | 5 | 8 | 3 | 1 |
| HAR331217 | SCC | 10 | 6 | 6 | 10 | 3 | 8 | 1 | 6 | 10 | 1 | 2 | 9 | 2 | 3 | 2 |
| HOU501106 | AC | 8 | 3 | 10 | 6 | 8 | 9 | 10 | 8 | 10 | 5 | 9 | 5 | 10 | 4 | 6 |
| IGL380217 | AC | 1 | 7 | 9 | 5 | 4 | 3 | 6 | 10 | 9 | 3 | 8 | 7 | 3 | 4 | 1 |
| ISA300917 | SCC | 3 | 4 | 2 | 4 | 2 | 1 | 6 | 5 | 5 | 8 | 4 | 6 | 9 | 3 | 4 |
| IVA360731 | SCC | 1 | 2 | 5 | 7 | 1 | 7 | 7 | 1 | 2 | 8 | 7 | 1 | 9 | 6 | 5 |
| JAY440311 | AC | 7 | 1 | 8 | 4 | 2 | 1 | 2 | 1 | 5 | 9 | 3 | 1 | 4 | 8 | 6 |
| JEA320618 | LCC | 10 | 1 | 3 | 10 | 9 | 8 | 6 | 8 | 8 | 6 | 10 | 5 | 9 | 10 | 5 |
| KEI431016 | SCC | 4 | 4 | 9 | 8 | 9 | 8 | 4 | 7 | 10 | 6 | 4 | 2 | 4 | 9 | 9 |

TABLE 3-continued summarises scores obtained for all patients of the 123 NSCLC, for a selection of interventional points

| patient | Histo | Her | CDK4_6 | ANGIO | PI3K | MET | MEK | ERK | FGF | mTOR | RAS | RAF | PARP | JAK_STAT | PDL1 | CTLA4 |
|---|---|---|---|---|---|---|---|---|---|---|---|---|---|---|---|---|
| KON381027 | AC | 9 | 8 | 10 | 1 | 1 | 2 | 2 | 1 | 9 | 1 | 4 | 3 | 1 | 2 | 1 |
| KRA420928 | AC | 10 | 1 | 8 | 7 | 9 | 7 | 10 | 8 | 8 | 4 | 8 | 1 | 10 | 4 | 9 |
| LAM380228 | AC | 6 | 7 | 10 | 5 | 4 | 5 | 5 | 4 | 4 | 9 | 7 | 5 | 3 | 3 | 4 |
| LAN041130 | LCC | 10 | 8 | 1 | 4 | 10 | 9 | 1 | 8 | 9 | 5 | 10 | 10 | 4 | 8 | 10 |
| LAN510426 | SCC | 10 | 9 | 1 | 9 | 3 | 8 | 3 | 9 | 3 | 9 | 7 | 7 | 10 | 10 | 10 |
| LEF320516 | SCC | 8 | 5 | 10 | 3 | 8 | 1 | 9 | 8 | 8 | 1 | 2 | 5 | 3 | 5 | 1 |
| LEF341111 | SCC | 7 | 9 | 8 | 1 | 2 | 3 | 9 | 10 | 10 | 1 | 2 | 9 | 2 | 2 | 3 |
| LEJ501115 | SCC | 1 | 2 | 5 | 3 | 5 | 2 | 7 | 1 | 1 | 3 | 2 | 4 | 8 | 7 | 4 |
| LEL450721 | AC | 1 | 10 | 1 | 2 | 10 | 2 | 8 | 5 | 9 | 1 | 1 | 6 | 7 | 2 | 9 |
| LEM351012 | LCC | 9 | 8 | 4 | 6 | 3 | 2 | 6 | 1 | 10 | 1 | 2 | 10 | 1 | 1 | 1 |
| LEN371015 | SCC | 3 | 3 | 1 | 3 | 6 | 1 | 10 | 10 | 9 | 6 | 1 | 7 | 5 | 1 | 3 |
| LEP560531 | AC | 8 | 2 | 10 | 8 | 7 | 3 | 1 | 3 | 2 | 5 | 6 | 3 | 1 | 2 | 6 |
| LER460716 | SCC | 2 | 1 | 10 | 5 | 3 | 3 | 2 | 5 | 3 | 9 | 7 | 4 | 6 | 6 | 8 |
| MAC460101 | AC | 7 | 1 | 8 | 1 | 1 | 5 | 8 | 2 | 2 | 4 | 5 | 7 | 7 | 6 | 4 |
| MAC381220 | SCC | 4 | 4 | 4 | 2 | 7 | 10 | 8 | 5 | 7 | 5 | 9 | 3 | 2 | 7 | 1 |
| MAR240911 | SCC | 5 | 2 | 5 | 2 | 1 | 6 | 7 | 10 | 5 | 5 | 7 | 4 | 2 | 3 | 4 |
| MAR491126 | SCC | 7 | 9 | 4 | 3 | 4 | 2 | 10 | 9 | 8 | 7 | | | | | |
| MAR430726 | AC | 9 | 4 | 8 | 6 | 3 | 5 | 6 | 5 | 3 | 2 | 7 | 7 | 5 | 6 | 7 |
| MAR350507 | SCC | 7 | 6 | 5 | 10 | 6 | 6 | 9 | 7 | 8 | 1 | 9 | 8 | 9 | 6 | 5 |
| MAR470322 | LCC | 3 | 5 | 7 | 2 | 5 | 8 | 7 | 5 | 7 | 5 | 5 | 10 | 9 | 9 | 9 |
| MAT230414 | SCC | 4 | 10 | 2 | 10 | 4 | 5 | 7 | 7 | 10 | 5 | 4 | 1 | 7 | 4 | 8 |
| MER490318 | AC | 10 | 2 | 6 | 8 | 8 | 8 | 2 | 3 | 3 | 10 | 6 | 3 | 4 | 9 | 4 |
| NEG410311 | AC | 10 | 8 | 2 | 8 | 8 | 10 | 2 | 2 | 9 | 7 | 10 | 6 | 10 | 5 | 6 |
| NIN270409 | AC | 10 | 8 | 7 | 3 | 10 | 9 | 5 | 4 | 3 | 4 | 10 | 2 | 8 | 7 | 7 |
| PAN390607 | AC | 6 | 1 | 9 | 3 | 2 | 1 | 9 | 4 | 1 | 3 | 1 | 1 | 1 | 1 | 1 |
| PEC481113 | AC | 10 | 2 | 5 | 6 | 4 | 1 | 5 | 4 | 2 | 3 | 9 | 2 | 4 | 2 | 2 |
| PER401217 | Other ADEC | 1 | 4 | 2 | 1 | 2 | 1 | 7 | 9 | 1 | 4 | 6 | 4 | 8 | 8 | 3 |
| PER510713 | AC | 2 | 3 | 7 | 4 | 6 | 8 | 1 | 4 | 5 | 7 | 8 | 2 | 6 | 7 | 8 |
| PIQ340906 | SCC | 5 | 1 | 9 | 1 | 1 | 7 | 7 | 2 | 6 | 4 | 2 | 4 | 1 | 5 | 2 |
| RAB330621 | SCC | 6 | 8 | 5 | 10 | 2 | 4 | 6 | 9 | 2 | 8 | 5 | 8 | 2 | 2 | 2 |
| RAM530325 | AC | 9 | 8 | 7 | 3 | 5 | 9 | 1 | 7 | 6 | 4 | 5 | 4 | 3 | 8 | 3 |
| REC590707 | LCC | 4 | 9 | 6 | 8 | 3 | 10 | 9 | 6 | 10 | 3 | 3 | 9 | 1 | 8 | 5 |
| REJ471005 | SCC | 10 | 6 | 4 | 9 | 5 | 7 | 9 | 9 | 6 | 2 | 2 | 8 | 10 | 6 | 10 |
| RIT431108 | AC | 10 | 10 | 4 | 9 | 9 | 4 | 9 | 6 | 1 | 10 | 8 | 6 | 10 | 10 | 10 |
| RIT490630 | SCC | 2 | 6 | 7 | 7 | 3 | 9 | 7 | 5 | 4 | 7 | 7 | 9 | 6 | 5 | 9 |
| SAI380426 | AC | 5 | 8 | 10 | 9 | 8 | 4 | 5 | 10 | 7 | 8 | 1 | 1 | 6 | 8 | 3 |
| SAU450710 | SCC | 3 | 5 | 2 | 2 | 1 | 5 | 9 | 10 | 1 | 8 | 5 | 7 | 1 | 1 | 1 |
| SER300810 | LCC | 2 | 4 | 10 | 1 | 5 | 7 | 9 | 4 | 2 | 5 | 9 | 2 | 5 | 7 | 2 |
| SIK471101 | AC | 8 | 3 | 8 | 5 | 10 | 5 | 8 | 2 | 4 | 10 | 6 | 3 | 5 | 6 | 7 |
| SUT470608 | SCC | 4 | 3 | 9 | 7 | 4 | 6 | 2 | 5 | 7 | 4 | 3 | 9 | 5 | 7 | 5 |
| TAI320613 | AC | 10 | 5 | 5 | 3 | 2 | 4 | 8 | 1 | 3 | 8 | 1 | 9 | 3 | 7 | 1 |
| TAR290829 | SCC | 3 | 7 | 3 | 4 | 1 | 1 | 8 | 8 | 1 | 2 | 3 | 8 | 3 | 2 | 3 |
| TAT400901 | AC | 9 | 6 | 10 | 5 | 10 | 3 | 1 | 7 | 6 | 10 | 2 | 5 | 4 | 3 | 6 |
| THU220630 | SCC | 2 | 3 | 7 | 4 | 5 | 4 | 1 | 7 | 5 | 8 | 3 | 6 | 4 | 8 | 3 |
| TIL420228 | SCC | 10 | 4 | 4 | 6 | 7 | 6 | 8 | 7 | 5 | 4 | 6 | 7 | 9 | 10 | 8 |
| UST500306 | SCC | 1 | 10 | 1 | 10 | 1 | 5 | 4 | 4 | 6 | 3 | 1 | 9 | 4 | 1 | 9 |
| VAL271009 | SCC | 5 | 3 | 6 | 5 | 2 | 6 | 6 | 8 | 6 | 5 | 9 | 8 | 8 | 9 | 5 |
| VIL310309 | SCC | 6 | 10 | 9 | 8 | 8 | 1 | 4 | 6 | 9 | 9 | 2 | 8 | 7 | 9 | 10 |
| WIS320823 | SCC | 2 | 3 | 1 | 8 | 2 | 9 | 3 | 7 | 3 | 9 | 3 | 9 | 10 | 10 | 8 |
| YOT471216 | AC | 2 | 7 | 4 | 9 | 4 | 10 | 3 | 3 | 6 | 7 | 8 | 6 | 9 | 7 | 10 |
| ZIT420630 | AC | 8 | 7 | 10 | 9 | 6 | 10 | 8 | 10 | 7 | 7 | 8 | 3 | 9 | 9 | 2 |

In the next step, the inventor selected from all activated interventional points. Scores 8, 9 and 10 were considered designating an important/high activation, whereas scores 6 and 7 were considered designating medium activation. Scores <6 were considered as designating non activated interventional points.

TABLE 4 shows the complexity of co-activation of interventional points. Each patient's tumors show multiple activations, suggesting multiple possibilities of combinations. All 24 interventional points were analysed

| ID | High activation score: 8, 9 and 10 indicated with * | | | | | | | Medium activation score: 6 and 7 | | | | |
|---|---|---|---|---|---|---|---|---|---|---|---|---|
| AGG600716 | MEK* | Antiap* | IGF* | PDL1* | CTLA4* | PARP* | AURKA | RAS | JAK_STAT | DNAREP | WNT | NOTCH |
| ANO420520 | IGF_War* | Antiap* | PDL1* | CTLA4* | CDK_4_6 | SCDK_4_6 | RCDK_4_6 | ANGIO | PI3K | RAS | HDAC | DNAREP* | NOTCH* |
| COU420201 | CDK_4_6* | Antiap* | AURKA* | PI3K* | ERK* | mTKPT* | TELOME* | IGF_War* | WNT* | PARP | RAF* | HEDGEHOG* |
| ECU520713 | CDK_4_6* | Antiap* | SCDK_4_6* | RCDK_4_6* | ANGIO* | MET* | FGF* | mTKPT | ModMTKT* | RAS* | HDAC | TELOME* | IGF* |
| FER471031 | ANGIO* | Antiap* | mTKPT* | RAF | TELOME | PARP | PDL1 | | | | | |
| FIL381013 | CDK_4_6* | Antiap* | CDK_4_6* | ANGIO* | MEK* | RAF* | JAK_STAT* | NOTCH* | PDL1* | CTLA4* | RAF* | JAK_STAT | HEDGHG* |
| GEF541216 | HER* | Antiap* | AURKA* | ANGIO* | AGPT* | PI3K* | MEK* | FGF* | mTKPT* | ModMTKT* | PLAURKi | RAS | DNA_REP |
| KON381027 | HER* | Antiap* | CDK_4_6* | ANGIO* | mTKPT* | PLAURKi | TELOME | HDAC | PDL1* | CTLA4* | RAS* | TELOME* | CTLA4* |
| LAM380228 | ANGIO* | Antiap* | AGPT* | RAS* | IGF_War* | HER | CDK_4_6 | SCDK_4_6 | RCDK_4_6 | RAF | | | |
| MER490318 | HER* | Antiap* | RAS* | HDAC* | PDL1* | ANGIO | RAF | IGF_War | | | | | |
| ZIT420630 | AGPT* | Antiapo* | ANGIO* | PI3K* | MEK* | ERK* | FGF* | RAF* | WNT* | HDAC* | JAK_STAT* | PDL1* | CDK_4_6 |
| AVI260916 | AGPT* | MEK* | ERK* | RAS* | FGF* | RAS* | JAK_STAT* | NOTCH* | PDL1 | mTKPT | WNT | HDAC | |
| AZE450213 | HER* | CDK_4_6* | ANGIO* | AGPT* | RAF* | RAF* | TELOME* | CTLA4* | JAK_STAT* | MEK | WNT | | |
| BAS260512 | HER* | PARP | HDAC | HEDGEHG | PARP | HDAC | | | | | | | |
| BAS260724 | CDK_4_6* | AURKA* | ANGIO* | MET* | ANGIO* | RAS | | PDL1* | TELOME* | HEDGEHOG | CTLA4 | | |
| BER520430 | HER | FGF | mTKPT | RAS | HEDGEHOG | IGF | | | | | | | |
| BOU480910 | AGPT* | MEK* | WNT* | ANGIO | MEK* | RAS | IGF_War | JAK_STAT | NOTCH | CTLA4 | | | |
| BOU520111 | AGPT* | CTLA4* | HER | AURKA | AURKA | Antiap | RAF | HDAC | DNA_REP | PDL1 | | | |
| BRZ470326 | ANGIO* | MEK* | JAK_STAT* | CTLA4* | CTLA4* | MEK* | | mTKPT* | | | | | |
| BRO521127 | CDK_4_6* | AURKA* | ANGIO* | PI3K* | PI3K* | AGPT | WNT | MET* | | DNA_REP* | PDL1* | CTLA4* | FGF |
| CHA280524 | HER* | PI3K* | ERK* | AGPT | ERK* | MET | MET* | mTKPT* | | | | | |
| CHE511225 | AURKA* | MET* | MET* | ERK* | mTKPT* | RAF* | TELOME* | M_MTKPT* | PARP* | DNA_REP* | HER | PDL1* | Antiap |
| DEL330821 | CDK_4_6* | PI3K* | MET* | MEK* | Antiap* | RAF* | Antiap* | mTKPT* | RAS* | TELOM* | WNT* | MEK | HER |
| DES580418 | CDK_4_6* | AGPT* | MET* | ERK* | mTKPT* | mTKPT* | TELOME* | PARP* | HDAC* | JAK_STAT* | PDL1* | CTLA4* | MEK |
| DEW440406 | ANGIO | MET | RAS | RAF | RAF | CTLA4 | CTLA4 | | | | PDL1* | PI3K | |
| ELB330728 | Antiap* | IGF_War* | PARP* | HDAC* | DNA_REP* | HER* | AURKA | ANGIO | DNA_REP* | MET | RAS | JAK_STAT | |
| FLA490711 | ANGIO* | AGPT* | mTKPT* | TELOM* | IGF_War* | PARP* | PARP* | HDAC* | PLAURKi | PDL1* | | RAF | |
| FOR440321 | ANGIO* | MET* | RAF* | HER | WNT* | CDK_4_6 | ERK | WNT | DNA_REP | PDL1* | CTLA4 | | |
| FRO440806 | MET | Antiap | RAS | DNA_REP | CTLA4 | RAF | | | | | | | |
| GID490224 | ANGIO* | MEK* | RAF* | RAF* | WNT* | HER | CDK_4_6 | mTKPT | DNA_REP | | | | |
| GIR220606 | HER* | ERK* | RAS* | RAF* | AGPT | MET | HEDGEHOG | | | | | | |
| GOE191205 | AGPT* | | ANGIO | RAS | HDAC | | | | | | | | |
| GRO250108 | HER* | AURKA* | PI3K* | MEK* | ERK* | RAS* | mTKPT* | RAF* | CTLA4 | HDAC | PI3K | JAK_STAT* | CTLA4* |
| GRY470526 | HER* | MET* | JAK_STAT* | CDK_4_6* | RAF | TELOM | RAF | CTLA4 | AGPT | MEK | PDL1* | mTKPT | HDAC |
| GUI390806 | FGF* | RAS* | RAF* | IGF_War* | WNT* | NOTCH* | JAK_STAT* | CDK_4_6 | HDAC | JAK_STAT | CTLA4 | PI3K | |
| GUI200304 | PI3K* | MET* | MEK* | FGF* | mTKPT* | RAS* | RAF* | WNT* | IGF_War* | AGPT | JAK_STAT* | HEDGEHOG* | |
| HOU501106 | ANGIO* | MET* | MEK* | ERK* | FGF* | mTKPT* | mTKPT* | RAF* | AGPT | HDAC* | PARP | AGPT | |
| IGL380217 | AGPT* | | FGF* | RAF* | IGF_War* | HEDGEHOG* | RAS | AURKA | ERK | Antiap | DNA_REP | NOTCH | |
| JAY440311 | ANGIO* | RAS* | PDL1* | HER | AGPT | AGPT | | JAK_STAT* | DNA_REP* | PARP | CTLA4* | PI3K | |
| KRA420928 | HER* | ANGIO* | AGPT* | MET* | ERK* | FGF* | mTKPT* | RAF* | IGF_War* | CTLA4* | DNA_REP* | MEK |

TABLE 4-continued shows the complexity of co-activation of interventional points. Each patient's tumors show multiple activations, suggesting multiple possibilities of combinations. All 24 interventional points were analysed

| ID | High activation score: 8, 9 and 10 indicated with * | | | | | | | | | Medium activation score: 6 and 7 | | | | |
|---|---|---|---|---|---|---|---|---|---|---|---|---|---|---|
| LEL450721 | CDK 4_6* | MET* | ERK* | Antiap* | mTKPT* | DNA_REP* | CTLA4* | AURKA* | EGF_War* | WNT* | PARP* | | | |
| LEP56531 | HER* | ANGIO* | AGPT* | PI3K* | MET | RAF | CTLA4 | PARP | JAK_STAT | DNA_REP | | | | |
| MAC460101 | ANGIO* | ERK* | IGF_War* | WNT* | HER | AURKA | TELOM | PARP | HEDGE-HOG | PDL1 | | | | |
| MAR430726 | HER* | ANGIO* | AGPT* | PI3K | ERK | RAF | IGF_War | | | | | | | |
| NEG410311 | HER* | CDK 4_6* | AGPT* | PI3K* | MET* | MEK* | mTKPT* | RAF* | WNT* | JAK_STAT* | NOTCH* | RAS | IGF_War | PARP |
| NIN270409 | HER* | CDK 4_6* | MET* | MEK* | RAF* | JAK_STAT* | ANGIO | PDL1 | CTLA4 | | | | | |
| PAN390607 | ANGIO* | AGPT* | ERK* | HDAC* | HER | | | | | | | | | |
| PEC481113 | HER* | RAF* | PI3K | NOTCH | ERK | | | | | | | | | |
| PER510713 | AGPT* | MEK* | RAF* | CTLA4* | MET | RAS | JAK_STAT | PDL1 | | | | | | |
| RAM530325 | HER* | CDK 4_6* | MEK* | PDL1* | AGPT | FGF | mTKPT | IGF_War | DNA_REP* | NOTCH* | PDL1* | CTLA4* | | |
| RIT431108 | HER* | CDK 4_6* | AURKA* | PI3K* | MET | ERK* | Antiap* | RAS* | RAF* | HEDGE-HOG* | | | | |
| SAI380426 | CDK 4_6* | ANGIO* | AGPT* | PI3K* | FGF* | NOTCH* | PDL1* | RAF* | mTKPT | TELOM | IGF_War | JAK_STAT | | |
| SIK471101 | HER* | ANGIO* | AGPT* | MET* | RAS* | WNT* | RAF | CTLA4 | DNA_REP | PDL1 | | | | |
| TAI320613 | HER* | ERK* | RAS* | HDAC* | Antiap | TELOM | IGF_War | | | | | | | |
| TAT400901 | HER* | AURKA* | ANGIO* | Antiap* | RAS* | FGF* | RAS* | mTKPT | WNT* | RAS | HEDGE-HOG | CDK 4_6 | FGF | |
| YOT471216 | AGPT* | PI3K* | MEK* | RAF* | JAK_STAT* | CDK 4_6 | IGF_War* | Antiap | HEDGE-HOG | HDAC | DNA_REP* | PARP | PDL1 | |
| ARC270517 | Antiap* | HER* | AURKA* | FGF* | TELOM* | PARP* | DNA_REP* | | | | | | | |
| BOU291129 | Antiap* | CDK 4_6* | AURKA* | PI3K | WNT* | PARP* | HEDGE-HOG* | WNT* | DNA_REP* | PARP* | mTKPT | TELOM | HDAC | |
| DEP351121 | Antiap* | CDK 4_6* | AURKA* | AGPT* | ERK* | FGF* | mTKPT* | WNT* | PARP | HDAC* | HEDGE-HOG* | NOTCH* | ANGIO | |
| DHE321214 | Antiap* | HER* | MET* | AURKA* | RAF* | WNT* | RAS* | CDK 4_6* | PI3K* | PARP* | JAK_STAT* | HEDGE-HOG* | ERK | HEDGE-HOG |
| DOM590729 | Antiap* | CDK 4_6* | AURKA* | PI3K* | ERK* | FGF* | TELOM* | HDAC* | IGF_War* | WNT* | HDAC* | AURKA | DNA_REP* | |
| GAN350811 | Antiap* | HER* | CDK 4_6 | AURKA* | PI3K | MET | WNT* | TELOM* | PARP* | NOTCH* | DNA_REP* | NOTCH* | FGF | |
| GEO270114 | Antiap* | AURKA* | MET* | ERK* | RAS* | HDAC | JAK_STAT* | DNA_REP* | NOTCH* | MET | HER | RAS | PARP | |
| HAM640729 | Antiap* | AURKA* | ANGIO* | AGPT* | MEK* | ERK* | FGF* | HEDGE-HOG* | RAS* | TELOM | IGF_War* | RAF | IGF_War | NOTCH* |
| JEA320618 | Antiap* | ERK* | PI3K* | MET* | MEK* | FGF* | RAF* | PDL1* | JAK_STAT* | HDAC* | HEDGE-HOG* | AURKA | ERK | HEDGE-HOG |
| LEF320516 | Antiap* | PI3K* | ANGIO* | MET* | ERK* | FGF* | mTKPT* | TELOM* | IGF_War* | HDAC* | JAK_STAT* | AURKA | | |
| LEF341111 | Antiap* | CDK 4_6* | AURKA* | ANGIO* | MET* | FGF* | mTKPT* | HDAC* | DNA_REP* | NOTCH* | NOTCH* | HER | PARP | |
| LEN371015 | Antiap* | AURKA* | ERK* | FGF* | mTKPT* | PARP* | TELOM* | DNA_REP* | NOTCH* | MET | RAS | | | |
| MAC381220 | Antiap* | MEK* | ERK* | RAF* | IGF_War* | PARP* | HEDGE-HOG* | HDAC* | DNA_REP* | JAK_STAT* | RAF | HEDGE-HOG* | | |
| MAR350507 | Antiap* | AURKA* | PI3K* | ERK* | mTKPT* | ERK* | NOTCH | HDAC* | NOTCH* | TELOM* | HDAC* | JAK_STAT* | HEDGE-HOG | RAS |
| REC590707 | Antiap* | CDK 4_6* | AGPT* | CDK 4_6* | PI3K* | RAF* | PARP* | mTKPT* | TELOM* | PARP | DNA_REP | DNA_REP* | PDL1* | DNA_REP |
| SAU450710 | Antiap* | AGPT* | ERK* | RAS* | MEK* | HDAC* | HEDGE-HOG* | PDL1 | HDAC | | | | | ANGIO |
| SER300810 | Antiap* | ANGIO* | ERK* | RAF* | IGF_War* | MEK | TELOM | NOTCH | CTLA4* | PDL1* | HDAC | AGPT | FGF | |
| VIL310309 | Antiap* | AURKA* | ANGIO* | PI3K* | MET* | mTKPT* | RAS* | HEDGE-HOG* | MET* | PDL1 | HER | HEDGE-HOG | | WNT |

TABLE 4-continued shows the complexity of co-activation of interventional points. Each patient's tumors show multiple activations, suggesting multiple possibilities of combinations with *. All 24 interventional points were analysed

| ID | High activation score: 8, 9 and 10 indicated with * | | | | | | | Medium activation score: 6 and 7 | | | |
|---|---|---|---|---|---|---|---|---|---|---|---|
| BAR331123 | HER* | AURKA* | ANGIO* | AGPT* | PI3K* | Antiap* | FGF* | mTKPT* | RAS* | RAF* | TELOM* | WNT* | HDAC* | HEDGE-HOG* |
| BEM291129 | JAK_STAT* | PI3K | ERK | Antiap | FGF | NOTCH | CTLA4 | | | | | | |
| BEN480707 | PDL1* | MEK | RAS | JAK_STAT | | | | | | | | | |
| BEN410529 | ANGIO* | AGPT* | Antiap* | IGF_War* | RAF* | TELOM* | NOTCH* | HEDGE-HOG* | PDL1* | CTLA4* | HER | AURKA | HDAC | HDAC mTKPT |
| BIF410219 | HER* | CDK_4_6* | AURKA* | FGF* | FGF* | | | | DNAREP* | CTLA4* | ANGIO | MEK | MEK | FGF |
| CAM520101 | HER* | CDK_4_6* | PI3K* | MET* | MEK* | TELOM* | IGF_War* | | JAK_STAT* | AURKA | ANGIO | AGPT | ERK | |
| CAP460215 | AURKA* | MET* | Antiap* | PARP* | HEDGE-HOG* | AGPT | HDAC* | | | | | ERK | | |
| CHA571008 | HER* | MET | ERK | IGF_War | CTLA4 | | | | | | | | | HER |
| CHA470718 | ANGIO* | AGPT* | MET* | ERK* | mTKPT* | CTLA4* | | MEK | FGF | RAF | IGF_War | DNAREP | PDL1 | |
| CRE420423 | CDK_4_6* | ANGIO* | AGPT* | MET* | FGF* | | | IGF_War | WNT* | HEDGE-HOG* | NOTCH* | PDL1* | CTLA4* | CTLA4 |
| DAM200413 | CDK_4_6* | ANGIO* | AGPT* | Antiap* | RAS* | JAK_STAT* | NOTCH* | PDL1* | CTLA4* | PI3K | mTKPT | PARP | PDL1 | CTLA4 |
| DAV320407 | AURKA* | ANGIO* | FGF* | | WNT* | HEDGE-HOG* | DNAREP | MET | RAF | | | | |
| DUV330713 | ANGIO* | AGPT* | ERK* | Antiap* | RAF* | IGF_War* | PARP* | NOTCH* | HER | AURKA | FGF |
| EDO300812 | PI3K* | mTKPT* | WNT* | PARP* | AGPT | MEK | RAS | HEDGE-HOG* | TELOM | HDAC | HER | |
| ELA540809 | CDK_4_6* | FGF* | RAS* | RAF* | IGF_War* | WNT* | HDAC | HEDGE-HOG* | PDL1 | NOTCH | CTLA4 | |
| FER461230 | AGPT* | HEDGE-HOG* | ANGIO | PI3K | MEK | FGF | mTKPT | WNT | HDAC | | | |
| FOR410727 | AURKA* | PI3K* | WNT* | JAK_STAT* | NOTCH* | PDL1* | HER | CDK_4_6 | ERK | RAS | TELOM | PARP |
| GAR410813 | AURKA* | PI3K* | TELOM* | WNT* | HEDGE-HOG* | PARP* | DNAREP | NOTCH* | HEDGE-HOG* | PDL1* | HER | CDK_4_6 | ANGIO | AGPT |
| GAR450819 | HER* | PI3K* | Antiapopt* | TELOM* | WNT* | HEDGE-HOG* | DNAREP | NOTCH* | PDL1* | CTLA4* | CDK_4_6 | AGPT | HDAC |
| GIL230901 | FGF* | IGF_War* | HDAC* | PI3K | MET | PARP* | mTKPT | RAS | TELOM | JAK_STAT | HEDGE-HOG* | DNAREP | PDL1 |
| GOM450227 | HER* | AURKA* | AGPT* | PI3K* | Antiap* | FGF* | TELOM* | IGF_War* | PARP* | HDAC* | HEDGE-HOG* | NOTCH* | ANGIO | MET |
| HAR331217 | HER* | AURKA* | PI3K* | MEK* | mTKPT* | TELOM* | WNT* | PARP | HDAC | HEDGE-HOG* | DNAREP* | NOTCH* | CDK_4_6 | ANGIO |
| ISA300917 | ERK* | Antiap* | RAS* | JAK_STAT* | HEDGE-HOG* | ERK | TELOM | PARP | DNAREP | | | |
| IVA360731 | RAS* | JAK_STAT* | AGPT* | PI3K | MEK | ERK | RAF | PDL1 | FGF | RAS | JAK_STAT* | HEDGE-HOG* | | |
| KEI431016 | ANGIO* | AGPT* | PI3K* | MET* | MEK* | mTKPT* | PDL1* | mTKPT* | RAF* | | | |
| LAN041130 | HER* | CDK_4_6* | AURKA* | AURKA* | AGPT* | MET* | MEK* | CTLA4* | FGF* | HEDGE-HOG* | | | |
| LAN510426 | HER* | CDK_4_6* | AURKA* | AURKA* | PI3K* | MEK* | Antiap* | FGF* | RAS* | | | | |
| LEI501115 | JAK_STAT* | AGPT | ERK | Antiap | PDL1 | IGF_War* | NOTCH | TELOM | IGF_War* | PARP* |
| LEM351012 | HER* | CDK_4_6* | ARUKA* | mTKPT* | TELOM* | | | HDAC* | HEDGE-HOG* | DNAREP* | PI3K | PDL1* | CTLA4* | HDAC RAF |
| LER460716 | ANGIO* | RAS* | CTLA4* | RAF | HEDGE-HOG | | | | DNAREP* | ERK | | |
| MAR240911 | FGF* | MEK | ERK | RAF | TELOM | WNT | HEDGE-HOG | IGF_War | DNAREP | NOTCH | | | |

TABLE 4-continued shows the complexity of co-activation of interventional points. Each patient's tumors show multiple activations, suggesting multiple possibilities of combinations. All 24 interventional points were analysed

| ID | High activation score: 8, 9 and 10 indicated with * | | | | | | | | Medium activation score: 6 and 7 | | | | | |
|---|---|---|---|---|---|---|---|---|---|---|---|---|---|---|
| MAR491126 | CDK_4_6* | AURKA* | AGPT* | ERK* | Antiap* | FGF* | mTKPT* | HOG WNT* | HEDGE-HOG* | DNAREP* | CTLA4* | HER | RAS | TELOM |
| MAT230414 | MEK* | IGF_War* | PARP* | HDAC* | JAK_STAT* | DNAREP* | PDL1* | CTLA4* | AURKA | ANGIO | ERK | Antiapopt | mTKPT | TELOM |
| PAQ470203 | CDK_4_6* | AURKA* | PI3K* | Antiap* | mTKPT* | TELOM* | HDAC | JAK_STAT* | DNAREP* | PDL1* | CTLA4* | PI3K | PARP | |
| PER401217 | FGF* | IGF_War* | JAK_STAT* | PDL1* | ERK | RAF | TELOM | WNT* HEDGE-HOG | HDAC* | DNAREP* | NOTCH* | | | |
| PIQ340906 | ANGIO | TELOM* | HDAC* | NOTCH* | MEK | ERK | mTKPT | IGF_War | HEDGE-HOG | PDL1 | | | | |
| RAB330621 | CDK_4_6* | PI3K* | Antiap* | FGF* | RAS* | TELOM* | mTKPT | WNT* | PARP* | HDAC* | HEDGE-HOG* | DNAREP* | NOTCH* | HER |
| REJ471005 | HER* | AURKA* | PI3K* | ERK* | Antiap* | FGF* | TELOM* | PARP* | HDAC* | JAK_STAT* | DNAREP* | NOTCH* | CTLA4* | CDK_4_6 |
| RIT490630 | MEK* | WNT* | PARP* | NOTCH* | CTLA4* | CDK_4_6 | AURKA | ANGIO | PI3K | ERK | RAS | RAF | TELOM | IGF_War |
| SUT470608 | ANGIO* | AGPT* | Antiap* | WNT* | PARP* | HEDGE-HOG* | DNAREP* | NOTCH* | HDAC* | MEK | mTKPT | PDL1 | | |
| TAR290829 | ERK* | Antiap* | FGF* | WNT* | PARP* | HDAC* | HEDGE-HOG* | NOTCH* | CDK_4_6 | | | | | |
| THU220630 | AGPT* | RAS* | IGF_War* | PDL1* | ANGIO | FGF | TELOM | WNT | PARP | HEDGE-HOG | NOTCH | | | |
| TIL420228 | HER* | ERK* | JAK_STAT* | PDL1* | CTLA4* | AGPT | HEDGE-HOG* | MET | MEK | HEDGE-HOG | FGF | RAF | PARP | HDAC |
| UST500306 | CDK_4_6* | PI3K* | Antiap* | PARP* | HDAC* | HEDGE-HOG* | DNAREP* | CTLA4* | mTKPT | MEK | TELOM | WNT | | |
| VAL271009 | FGF* | RAF* | TELOM* | WNT* | PARP* | JAK_STAT* | PDL1* | MEK | ERK | Antiapopt | mTKPT | IGF_War | NOTCH | |
| WIS320823 | AURKA* | PI3K* | MEK* | Antiapop* | RAS* | TELOM* | WNT* | DNAREP* | HDAC* | JAK_STAT* | HEDGE-HOG* | DNAREP* | NOTCH* | PDL1* |

In a preferred embodiment, the frequency of activation of interventional points (score >5), enabling determination of the most rationale combinations is the following:

TABLE 5

Trends of cooactivation of interventional points

| CTLA4 | PD1L | mek | mTor | pi3k | ERK | met | AurkA | cdk4,6 | HER | Angio | FGF | PARP | Ras/RAF | IGF | DNAREP | mtor/PI3K | ID | Histo |
|---|---|---|---|---|---|---|---|---|---|---|---|---|---|---|---|---|---|---|
| 61 | 63 | 54 | 59 | 55 | 57 | 51 | 55 | 60 | 68 | 56 | 47 | 47 | 88 | 44 | 56 | 83 | N° patients | 123 |
| 50 | 51 | 44 | 48 | 45 | 46 | 41 | 45 | 49 | 55 | 46 | 38 | 38 | 72 | 36 | 46 | 67 | % | 100 |

TABLE 6

Selection of most frequent combinations taking into account trends of coactivation. For each of the first and second drug number of patients (upper case) and % (lower case) are showed. For each of the third drug number of patients out of 123 and % are shown.

| First drug | NB / % | Second drug | NB / % | Third drug | Nb | % |
|---|---|---|---|---|---|---|
| RAS/RAF | 88 / 72 | mTor/PI3K | 60 / 49 | PD1L | 34 | 28 |
|  |  |  |  | CTLA4 | 33 | 27 |
|  |  |  |  | CDK4,6 | 32 | 26 |
|  |  |  |  | AURKA | 29 | 24 |
|  |  |  |  | DNARepair | 28 | 23 |
|  |  |  |  | ANGIO | 27 | 22 |
|  |  |  |  | MET | 27 | 22 |
|  |  |  |  | FGF | 26 | 21 |
|  |  |  |  | PARP | 24 | 20 |
|  |  |  |  | IGF | 23 | 19 |
| RAS/RAF | 88 / 72 | MET | 40 / 33 | CTLA4 | 32 | 26 |
|  |  |  |  | mTor/PI3K | 27 | 22 |
|  |  |  |  | PD1L | 22 | 18 |
|  |  |  |  | ANGIO | 20 | 16 |
|  |  |  |  | CDK4,6 | 21 | 17 |
|  |  |  |  | AURKA | 17 | 14 |
|  |  |  |  | FGF | 17 | 14 |
|  |  |  |  | DNARepair | 15 | 12 |
|  |  |  |  | IGF | 13 | 11 |
|  |  |  |  | PARP | 12 | 10 |
| RAS/RAF | 88 / 72 | CDK4,6 | 40 / 33 | mTor/PI3K | 32 | 26 |
|  |  |  |  | CTLA4 | 27 | 22 |
|  |  |  |  | AURKA | 23 | 19 |
|  |  |  |  | MET | 21 | 17 |
|  |  |  |  | PD1L | 20 | 16 |
|  |  |  |  | DNARepair | 20 | 16 |
|  |  |  |  | ANGIO | 17 | 14 |
|  |  |  |  | FGF | 17 | 14 |
|  |  |  |  | PARP | 17 | 14 |
|  |  |  |  | IGF | 12 | 10 |
| mTor/PI3K | 83 / 67 | RAS/RAF | 60 / 49 | PD1L | 34 | 28 |
|  |  |  |  | CTLA4 | 33 | 27 |
|  |  |  |  | CDK4,6 | 32 | 26 |
|  |  |  |  | AURKA | 29 | 24 |
|  |  |  |  | DNARepair | 28 | 23 |
|  |  |  |  | MET | 27 | 22 |
|  |  |  |  | ANGIO | 27 | 22 |
|  |  |  |  | FGF | 26 | 21 |
|  |  |  |  | PARP | 24 | 20 |
|  |  |  |  | IGF | 23 | 19 |
| CDK4,6 | 63 / 51 | RAS/RAF | 51 / 41 | mTor/PI3K | 34 | 28 |
|  |  |  |  | CTLA4 | 27 | 22 |
|  |  |  |  | ANGIO | 24 | 20 |
|  |  |  |  | IGF | 23 | 19 |
|  |  |  |  | MET | 22 | 18 |
|  |  |  |  | AURKA | 22 | 18 |
|  |  |  |  | CDK4,6 | 20 | 16 |
|  |  |  |  | PD1L | 20 | 16 |
|  |  |  |  | FGF | 19 | 15 |
|  |  |  |  | PARP | 16 | 13 |
| PD1L | 63 / 51 | mTor/PI3K | 42 / 34 | RAS/RAF | 34 | 28 |
|  |  |  |  | CTLA4 | 25 | 20 |
|  |  |  |  | DNARepair | 23 | 19 |
|  |  |  |  | CDK4,6 | 21 | 17 |
|  |  |  |  | ANGIO | 21 | 17 |
|  |  |  |  | AURKA | 20 | 16 |
|  |  |  |  | IGF | 19 | 15 |
|  |  |  |  | FGF | 18 | 15 |
|  |  |  |  | MET | 16 | 13 |
|  |  |  |  | PARP | 15 | 12 |
| MEK | 54 / 44 | RAS/RAF | 42 / 34 | CTLA4 | 29 | 24 |
|  |  |  |  | PD1L | 28 | 23 |
|  |  |  |  | mTor/PI3K | 28 | 23 |
|  |  |  |  | CDK4,6 | 19 | 15 |
|  |  |  |  | ANGIO | 19 | 15 |
|  |  |  |  | IGF | 19 | 15 |
|  |  |  |  | AURKA | 16 | 13 |
|  |  |  |  | FGF | 16 | 13 |
|  |  |  |  | DNARepair | 15 | 12 |
|  |  |  |  | parp | 11 | 9 |
| CDK4,6 | 60 / 49 | mTor/PI3K | 48 / 39 | RAS/RAF | 32 | 26 |
|  |  |  |  | AURKA | 32 | 26 |
|  |  |  |  | DNARepair | 32 | 26 |
|  |  |  |  | CTLA4 | 29 | 24 |
|  |  |  |  | parp | 26 | 21 |
|  |  |  |  | FGF | 23 | 19 |
|  |  |  |  | MET | 22 | 18 |
|  |  |  |  | PD1L | 21 | 17 |
|  |  |  |  | ANGIO | 20 | 16 |
|  |  |  |  | IGF | 15 | 12 |
| MET | 51 / 41 | RAS/RAF | 40 / 33 | CTLA4 | 32 | 26 |
|  |  |  |  | mTor/PI3K | 27 | 22 |
|  |  |  |  | PD1L | 22 | 18 |
|  |  |  |  | ANGIO | 21 | 17 |
|  |  |  |  | MEK | 19 | 15 |
|  |  |  |  | AURKA | 17 | 14 |
|  |  |  |  | FGF | 17 | 14 |
|  |  |  |  | DNARepair | 15 | 12 |
|  |  |  |  | IGF | 13 | 11 |
|  |  |  |  | PARP | 12 | 10 |
| ANGIO | 56 / 46 | RAS/RAF | 41 / 33 | mTor/PI3K | 27 | 22 |
|  |  |  |  | PD1L | 24 | 20 |
|  |  |  |  | MET | 20 | 16 |
|  |  |  |  | MEK | 19 | 15 |
|  |  |  |  | AURKA | 19 | 15 |
|  |  |  |  | IGF | 17 | 14 |
|  |  |  |  | CDK4,6 | 16 | 13 |
|  |  |  |  | FGF | 15 | 12 |
|  |  |  |  | DNARepair | 14 | 11 |
|  |  |  |  | PARP | 7 | 6 |

TABLE 7 summarizes the most frequent triple combinations

| First drug | NB | Second drug | NB | Third drug | Nb | % |
|---|---|---|---|---|---|---|
| RAS/RAF | 88 | mTor/PI3K | 60 | PD1L | 34 | 28 |
| RAS/RAF | 88 | mTor/PI3K | 60 | CTLA4 | 33 | 27 |
| RAS/RAF | 88 | mTor/PI3K | 60 | CDK4,6 | 32 | 26 |
| RAS/RAF | 88 | mTor/PI3K | 60 | AURKA | 29 | 24 |
| RAS/RAF | 88 | mTor/PI3K | 60 | DNARepair | 28 | 23 |
| RAS/RAF | 88 | mTor/PI3K | 60 | ANGIO | 27 | 22 |
| RAS/RAF | 88 | mTor/PI3K | 60 | MET | 27 | 22 |
| RAS/RAF | 88 | mTor/PI3K | 60 | FGF | 26 | 21 |
| RAS/RAF | 88 | MET | 40 | CTLA4 | 32 | 26 |
| RAS/RAF | 88 | CDK4,6 | 40 | CTLA4 | 27 | 22 |
| CDK4,6 | 63 | RAS/RAF | 51 | ANGIO | 24 | 20 |
| CDK4,6 | 60 | mTor/PI3K | 48 | AURKA | 32 | 26 |
| CDK4,6 | 60 | mTor/PI3K | 48 | DNARepair | 32 | 26 |
| CDK4,6 | 60 | mTor/PI3K | 48 | CTLA4 | 29 | 24 |
| CDK4,6 | 60 | mTor/PI3K | 48 | PARP | 26 | 21 |
| MEK | 54 | RAS/RAF | 42 | CTLA4 | 29 | 24 |
| MEK | 54 | RAS/RAF | 42 | PD1L | 28 | 23 |
| MEK | 54 | RAS/RAF | 42 | mTor/PI3K | 28 | 23 |

TABLE 8

Summarizes the most frecquent combinations involving and immunomodulator

| First drug | NB | Second drug | NB | Third drug | Nb | % |
|---|---|---|---|---|---|---|
| RAS/RAF | 88 | mTor/PI3K | 60 | PD1L | 34 | 28 |
| RAS/RAF | 88 | MET | 40 | PD1L | 22 | 18 |
| RAS/RAF | 88 | CDK4,6 | 40 | PD1L | 20 | 16 |
| PD1L | 63 | mTor/PI3K | 42 | DNARepair | 23 | 19 |
| PD1L | 63 | mTor/PI3K | 42 | CDK4,6 | 21 | 17 |
| PD1L | 63 | mTor/PI3K | 42 | ANGIO | 21 | 17 |
| PD1L | 63 | mTor/PI3K | 42 | AURKA | 20 | 16 |
| PD1L | 63 | mTor/PI3K | 42 | IGF | 19 | 15 |
| PD1L | 63 | mTor/PI3K | 42 | FGF | 18 | 15 |
| PD1L | 63 | mTor/PI3K | 42 | MET | 16 | 13 |
| ANGIO | 56 | RAS/RAF | 41 | PD1L | 24 | 20 |
| RAS/RAF | 88 | mTor/PI3K | 60 | CTLA4 | 33 | 27 |
| RAS/RAF | 88 | MET | 40 | CTLA4 | 32 | 26 |
| RAS/RAF | 88 | CDK4,6 | 40 | CTLA4 | 27 | 22 |
| CDK4,6 | 63 | RAS/RAF | 51 | CTLA4 | 27 | 22 |
| PD1L | 63 | mTor/PI3K | 42 | CTLA4 | 25 | 20 |
| MEK | 54 | RAS/RAF | 42 | CTLA4 | 29 | 24 |
| CDK4,6 | 60 | mTor/PI3K | 48 | CTLA4 | 29 | 24 |
| MET | 51 | RAS/RAF | 40 | CTLA4 | 32 | 26 |

TABLE 9

Detailed List of genes

| Pathway | Symbol | GeneID | Name | Refseq |
|---|---|---|---|---|
| HER | EGF | 1950 | epidermal growth factor | NM_001963 |
| | TGFA | 7039 | transforming growth factor, alpha | NM_003236 |
| | AREG | 374 | amphiregulin | NM_001657 |
| | EREG | 2069 | epiregulin | NM_001432 |
| | HBEGF | 1839 | heparin-binding EGF-like growth factor | NM_001945 |
| | BTC | 685 | betacellulin | NM_001729 |
| | NRG1 | 3084 | neuregulin 1 | AF176921; NM_004495 |
| | NRG2 | 9542 | neuregulin 2 | ENST00000544729; NM_013982 |
| | NRG4 | 145957 | neuregulin 4 | NM_138573 |
| | EGFR | 1956 | epidermal growth factor receptor | NM_201283; NM_201282; NM_005228 |
| | ERBB2 | 2064 | v-erb-b2 avian erythroblastic leukemia viral oncogene homolog 2 | NM_001005862; AB025286 |
| | ERBB3 | 2065 | v-erb-b2 avian erythroblastic leukemia viral oncogene homolog 3 | NM_001982; NM_001005915 |
| | ERBB4 | 2066 | v-erb-b2 avian erythroblastic leukemia viral oncogene homolog 4 | NM_005235 |
| CDK4,6 | CDK4 | 1019 | cyclin-dependent kinase 4 | NM_000075 |
| | CDK6 | 1021 | cyclin-dependent kinase 6 | NM_001259 |
| | CCND1 | 595 | cyclin D1 | NM_053056 |
| | CCND2 | 894 | cyclin D2 | NM_001759 |
| | CCND3 | 896 | cyclin D3 | NM_001760 |
| | CDKN2A, | 1029 | cyclin-dependent kinase inhibitor 2A | NM_058197; NM_000077 |
| | CDKN2B | 1030 | cyclin-dependent kinase inhibitor 2B | NM_004936 |
| | CCNE1 | 898 | cyclin E1 | NM_001238 |
| | CCNE2 | 9134 | cyclin E2 | NM_057749 |
| | RB1 | 5925 | retinoblastoma 1 | NM_000321 |
| PLK/AURK/ Kinesins | PLK1 | 5347 | polo-like kinase 1 | NM_005030 |
| | AURKA | 6790 | aurora kinase A | NM_198433 |
| | BORA | 79866 | bora, aurora kinase A activator | NM_024808 |
| | ILK | 3611 | integrin-linked kinase | NM_001014795 |
| | KIF11 | 3832 | kinesin family member 11 | NM_004523 |
| ANGIOGENESIS | VEGFA | 7422 | vascular endothelial growth factor A | NM_001025370; NM_001025366 |
| | VEGFB | 7423 | vascular endothelial growth factor B | NM_003377 |
| | VEGFC | 7424 | vascular endothelial growth factor C | NM_005429 |
| | VEGFD | 2277 | c-fos induced growth factor (vascular endothelial growth factor D) | NM_004469 |
| | FLT1 | 2321 | fms-related tyrosine kinase 1 | NM_001160031; NM_002019 |
| | KDR | 3791 | kinase insert domain receptor (a type III receptor tyrosine kinase) | NM_002253 |

TABLE 9-continued

Detailed List of genes

| Pathway | Symbol | GeneID | Name | Refseq |
|---|---|---|---|---|
| | FLT4 | 2324 | fms-related tyrosine kinase 4 | ENST00000376868; NM_002020 |
| | PDGFA | 5154 | platelet-derived growth factor alpha polypeptide | NM_002607; NM_033023 |
| | PDGFB | 5155 | platelet-derived growth factor beta polypeptide | NM_002608 |
| | PDGFRA | 5156 | platelet-derived growth factor receptor, alpha polypeptide | NM_006206 |
| | PDGFRB | 5159 | platelet-derived growth factor receptor, beta polypeptide | NM_002609 |
| | Kit | 3815 | v-kit Hardy-Zuckerman 4 feline sarcoma viral oncogene homolog | NM_000222; NM_001093772 |
| ANGIOPOIETINS | THBS1 | 7057 | thrombospondin 1 | NM_003246 |
| | TGFB1 | 7040 | transforming growth factor, beta 1 | NM_000660 |
| | ANGPT1 | 284 | angiopoietin 1 | NM_001146 |
| | ANGPT2 | 285 | angiopoietin 2 | NM_001147 |
| | ANGPTL1 | 9068 | angiopoietin-like 1 | NM_004673 |
| | ANGPT4 | 51378 | angiopoietin 4 | NM_015985 |
| | TIE1 | 7075 | tyrosine kinase with immunoglobulin-like and EGF-like domains 1 | NM_005424 |
| | TEK | 7010 | TEK tyrosine kinase, endothelial | NM_000459 |
| IMMUNO-Modulator | CD274 or PDL1 | 29126 | CD274 molecule programmed cell death ligand 1 | NM_014143 |
| | PDCD1LG2 | 80380 | programmed cell death 1 ligand 2 | NM_025239 |
| | PDCD1 | 5133 | programmed cell death 1 | NM_005018 |
| | CTLA4 | 1493 | cytotoxic T-lymphocyte-associated protein 4 | NM_005214 |
| | LAG3 | 3902 | lymphocyte-activation gene 3 | NM_002286 |
| PI3K | PIK3CA | 5290 | phosphatidylinositol-4,5-bisphosphate 3-kinase, catalytic subunit alpha | NM_006218 |
| | PIK3CB | 5291 | phosphatidylinositol-4,5-bisphosphate 3-kinase, catalytic subunit beta | NM_006219 |
| | PIK3CD | 5293 | phosphatidylinositol-4,5-bisphosphate 3-kinase, catalytic, catalytic subunit delta | NM_005026 |
| | PIK3CG | 5294 | phosphatidylinositol-4,5-bisphosphate 3-kinase, catalytic subunit gamma | NM_002649 |
| | PIK3C2B | 5287 | phosphatidylinositol-4,5-bisphosphate 3-kinase, catalytic subunit type 2 beta | NM_002646; ENST00000367184 |
| | PRKCB | 5579 | protein kinase C, beta | NM_002738 |
| | PRKCA | 5578 | protein kinase C, alpha | NM_002737 |
| | PIK3R1 | 5295 | phosphoinositide-3-kinase, regulatory subunit 1 (alpha) | NM_181523 |
| | PIK3R2 | 5296 | phosphoinositide-3-kinase, regulatory subunit 2 (beta) | NM_005027 |
| | PIK3R3 | 8503 | phosphoinositide-3-kinase, regulatory subunit 3 (gamma) | NM_003629 |
| MET | HGF | 3082 | hepatocyte growth factor (hepapoietin A; scatter factor) | NM_001010934; NM_001010931 |
| | MET | 4233 | met proto-oncogene | NM_000245 |
| | AXL | 558 | AXL receptor tyrosine kinase | NM_021913 |
| | MST1R | 4486 | macrophage stimulating 1 receptor (c-met-related tyrosine kinase) | NM_002447 |
| MEK | MAP2K1 | 5604 | mitogen-activated protein kinase kinase 1, E3 ubiquitin protein ligase | NM_002755 |
| | MAP2K2 | 5605 | mitogen-activated protein kinase kinase 2 | NM_030662 |
| | MAP2K3 | 5606 | mitogen-activated protein kinase kinase 3 | NM_145109; ENST00000534743 |
| | MAP2K4 | 6416 | mitogen-activated protein kinase kinase 4 | NM_003010 |
| | MAP3K1 | 4214 | mitogen-activated protein kinase kinase kinase 1 | NM_005921 |
| | MAP3K2 | 10746 | mitogen-activated protein kinase kinase kinase 2 | NM_006609 |
| | MAP3K3 | 4215 | mitogen-activated protein kinase kinase kinase 3 | NM_203351 |
| | MAP3K4 | 4216 | mitogen-activated protein kinase kinase kinase 4 | NM_005922; NM_006724 |
| ERK | MAPK3 | 5595 | mitogen-activated protein kinase 3 | NM_002746 |
| | MAPK1 | 5594 | mitogen-activated protein kinase 1 | NM_138957 |
| | KSR1 | 8844 | kinase suppressor of ras 1 | NM_014238 |
| | MAPK11 | 5600 | mitogen-activated protein kinase 11 | NM_002751 |
| ANTI-APOPTOSIS | BCL2 | 596 | B-cell CLL/lymphoma 2 | NM_000633; NM_000657 |
| | BCL2L1 | 598 | BCL2-like 1 | NM_138578 |
| | BIRC5 | 332 | baculoviral IAP repeat containing 5 | NM_001012271 |
| | XIAP | 331 | X-linked inhibitor of apoptosis | NM_001167 |
| | BAK1 | 578 | BCL2-antagonist/killer 1 | NM_001188 |
| FGF | FGF1 | 2246 | fibroblast growth factor 1 (acidic) | NM_000800; NR_026696 |
| | FGF2 | 2247 | fibroblast growth factor 2 (basic) | NM_002006 |
| | FGF3 | 2248 | fibroblast growth factor 3 | NM_005247 |
| | FGF4 | 2249 | fibroblast growth factor 4 | NM_002007 |
| | FGF5 | 2250 | fibroblast growth factor 5 | NM_004464; NM_033143 |
| | FGF6 | 2251 | fibroblast growth factor 6 | NM_020996 |
| | FGF7 | 2252 | fibroblast growth factor 7 | NM_002009 |
| | FGF8 | 2253 | fibroblast growth factor 8 (androgen-induced) | NM_033163 |

TABLE 9-continued

Detailed List of genes

| Pathway | Symbol | GeneID | Name | Refseq |
|---|---|---|---|---|
| | FGF9 | 2254 | fibroblast growth factor 9 | NM_002010 |
| | FGF10 | 2255 | fibroblast growth factor 10 | NM_004465 |
| | FGF11 | 2256 | fibroblast growth factor 11 | NM_004112 |
| | FGF12 | 2257 | fibroblast growth factor 12 | NM_004113 |
| | FGF13 | 2258 | fibroblast growth factor 13 | NM_004114 |
| | FGF14 | 2259 | fibroblast growth factor 14 | NM_175929 |
| | FGFR1 | 2260 | fibroblast growth factor receptor 1 | ENST00000496296; NM_023110; NM_001174066 |
| | FGFR2 | 2263 | fibroblast growth factor receptor 2 | ENST00000359354; NM_022970 |
| | FGFR3 | 2261 | fibroblast growth factor receptor 3 | NM_000142 |
| | FGFR4 | 2264 | fibroblast growth factor receptor 4 | NM_213647 |
| mTOR-AKT-PTEN-Modulators MTKPT | mTor | 2475 | mechanistic target of rapamycin (serine/threonine kinase) | NM_004958 |
| | AKT1 | 207 | v-akt murine thymoma viral oncogene homolog 1 | NM_005163 |
| | AKT2 | 208 | v-akt murine thymoma viral oncogene homolog 2 | NM_001626 |
| | PTEN | 5728 | phosphatase and tensin homolog | NM_000314 |
| | TSC1 | 7248 | tuberous sclerosis 1 | NM_000368; ENST00000403810 |
| | TSC2 | 7249 | tuberous sclerosis 2 | NM_000548; NM_001077183 |
| | STK11 | 6794 | serine/threonine kinase 11 | NM_000455 |
| | PIM1 | 5292 | pim-1 oncogene | NM_002648 |
| | PIM2 | 11040 | pim-2 oncogene | NM_006875 |
| | PIM3 | 415116 | pim-3 oncogene | NM_001001852 |
| RAS | KRAS | 3845 | Kirsten rat sarcoma viral oncogene homolog | NM_033360; NM_004985 |
| | NRAS | 4893 | neuroblastoma RAS viral (v-ras) oncogene homolog | NM_002524 |
| | HRAS | 3265 | Harvey rat sarcoma viral oncogene homolog | NM_005343 |
| RAF | RAF1 | 5894 | v-raf-1 murine leukemia viral oncogene homolog 1 | NM_002880 |
| | BRAF | 673 | v-raf murine sarcoma viral oncogene homolog B | NM_004333 |
| TELOMERASE | TERT | 7015 | telomerase reverse transcriptase | NM_198253 |
| | TERC | 7012 | telomerase RNA component | NR_001566 |
| | TEP1 | 7011 | telomerase-associated protein 1 | NM_007110 |
| | HSP90AA1 | 3320 | heat shock protein 90 kDa alpha, class A member 1 | NM_001017963; NM_005348 |
| | DKC1 | 1736 | dyskeratosis congenita 1, dyskerin | NM_001363 |
| | PTGES3 | 10728 | prostaglandin E synthase 3 | NM_006601 |
| IGF & Warburg | IGF1 | 3479 | insulin-like growth factor 1 (somatomedin C) | NM_000618 |
| | IGF2 | 3481 | insulin-like growth factor 2 (somatomedin A) | NM_000612 |
| | IGF1R | 3480 | insulin-like growth factor 1 receptor | NM_000875 |
| | IGF2R | 3482 | insulin-like growth factor 2 receptor | NM_000876 |
| | INSR | 3643 | insulin receptor | NM_000208 |
| | IRS1 | 3667 | insulin receptor substrate 1 | NM_005544 |
| | PKM | 5315 | pyruvate kinase, muscle | NM_001206796.1 |
| WNT | CDH1 | 999 | cadherin 1, type 1, E-cadherin (epithelial) | NM_004360 |
| | CTNNA1 | 1495 | catenin (cadherin-associated protein), alpha 1, 102 kDa | NM_001903 |
| | CTNNB1 | 1499 | catenin (cadherin-associated protein), beta 1, 88 kDa | NM_001904; NM_001098210 |
| | WNT1 | 7471 | wingless-type MMTV integration site family, member 1 | NM_005430 |
| | FZD1 | 8321 | frizzled class receptor 1 | NM_003505 |
| | WNT5A | 7474 | wingless-type MMTV integration site family, member 5A | NM_003392 |
| | WNT5B | 81029 | wingless-type MMTV integration site family, member 5B | NM_030775 |
| | FZD5 | 7855 | frizzled class receptor 5 | NM_003468 |
| | WIF1 | 11197 | WNT inhibitory factor 1 | NM_007191 |
| | DKK1 | 22943 | dickkopf WNT signaling pathway inhibitor 1 | NM_012242 |
| PARP | PARP1 | 142 | poly (ADP-ribose) polymerase 1 | NM_001618; ENST00000366790 |
| | BRCA1 | 672 | breast cancer 1, early onset | NM_007300 |
| | XRCC1 | 7515 | X-ray repair complementing defective repair in Chinese hamster cells 1 | NM_006297 |
| | RAD54L | 8438 | RAD54-like (S. cerevisiae) | NM_003579 |
| | RAD54B | 25788 | RAD54 homolog B (S. cerevisiae) | NM_012415; NM_001205262 |
| | ATM | 472 | ataxia telangiectasia mutated | NM_000051; ENST00000389511 |
| | ATR | 545 | ataxia telangiectasia and Rad3 related | NM_001184 |
| | CHEK1 | 1111 | checkpoint kinase 1 | NM_001114121 |
| | CHEK2 | 11200 | checkpoint kinase 2 | NM_145862; NM_001005735 |
| | WEE1 | 7465 | WEE1 G2 checkpoint kinase | NM_003390 |
| HDAC | HDAC1 | 3065 | histone deacetylase 1 | NM_004964 |
| | HDAC2 | 3066 | histone deacetylase 2 | NM_001527 |
| | HDAC3 | 8841 | histone deacetylase 3 | NM_003883 |
| | HDAC4 | 9759 | histone deacetylase 4 | NM_006037 |
| | HDAC5 | 10014 | histone deacetylase 5 | NM_001015053 |

TABLE 9-continued

Detailed List of genes

| Pathway | Symbol | GeneID | Name | Refseq |
|---|---|---|---|---|
| JAK-STAT | JAK1 | 3716 | Janus kinase 1 | NM_002227 |
| | JAK2 | 3717 | Janus kinase 2 | NM_004972 |
| | STAT1 | 6772 | signal transducer and activator of transcription 1, 91 kDa | NM_139266 |
| | STAT2 | 6773 | signal transducer and activator of transcription 2, 113 kDa | NM_005419 |
| | STAT3 | 6774 | signal transducer and activator of transcription 3 (acute-phase response factor) | NM_213662 |
| | SOCS1 | 8651 | suppressor of cytokine signaling 1 | NM_003745 |
| HEDGEHOG | SHH | 6469 | sonic hedgehog | NM_000193 |
| | PTCH1 | 5727 | patched 1 | NM_001083602; ENST00000375290 |
| | SMO | 6608 | smoothened, frizzled class receptor | NM_005631 |
| | STK36 | 27148 | serine/threonine kinase 36 | NM_015690 |
| | PRKACA | 5566 | protein kinase, cAMP-dependent, catalytic, alpha | NM_002730 |
| | SUFU | 51684 | suppressor of fused homolog (*Drosophila*) | NM_016169; NM_001178133 |
| | GLI1 | 2735 | GLI family zinc finger 1 | NM_005269 |
| DNA REPAIR | ERCC1 | 2067 | excision repair cross-complementation group 1 | NM_202001 |
| | RAD52 | 5893 | RAD52 homolog (*S. cerevisiae*) | NM_134424; ENST00000545967 |
| | XRCC4 | 7518 | X-ray repair complementing defective repair in Chinese hamster cells 4 | NM_022550 |
| | RAD51 | 5888 | RAD51 recombinase | NM_002875 |
| | BRCA1 | 672 | breast cancer 1, early onset | NM_007300 |
| | NEDD8 | 4738 | neural precursor cell expressed, developmentally down-regulated 8 | NM_006156 |
| | NAE1 | 8883 | NEDD8 activating enzyme E1 subunit 1 | NM_001018159 |
| NOTCH | NOTCH1 | 4851 | notch 1 | NM_017617 |
| | Adam17 | 6868 | ADAM metallopeptidase domain 17 | NM_003183 |
| | PSEN1 | 5663 | presenilin 1 | NM_000021; ENST00000394157 |
| | NCSTN | 23385 | nicastrin | NM_015331 |
| | JAG1 | 182 | jagged 1 | NM_000214 |
| | SRRT | 51593 | serrate RNA effector molecule homolog (*Arabidopsis*) | NM_001128853; NM_015908; NM_001128854 |
| | APH1A | 51107 | APH1A gamma secretase subunit | NM_016022; NM_001077628 |
| Others | ROS1 | 6098 | c-ros oncogene 1, receptor tyrosine kinase | ENST00000403284; NM_002944 |
| | ALK | 238 | anaplastic lymphoma receptor tyrosine kinase | NM_004304 |
| | RET | 5979 | ret proto-oncogene | NM_020630; NM_020975 |
| | UBA1 | 7317 | ubiquitin-like modifier activating enzyme 1 | NM_003334 |

TABLE 10

List of genes mutations

BRAF

| Nucleotide | Protein | |
|---|---|---|
| c.1799 T > W | p.Val600Glu | V600E |
| c.1798 G > R c.1799 T > W | p.Val600Lys | V600K |
| c.1799 T > W c.1800G > R | p.Val600Glu | V600E |
| c.1780 G > R | p.Asp594Asn | D594N |

EGFR

| Nucleotide | Protein | | Effect on EGFR inhibitors |
|---|---|---|---|
| c.2156G > C | p.Gly719Ala | G719A | Sensibility |
| c.2155 G > K | p.Gly719Cys | G719C | Sensibility |
| c.2117 T > Y | p.Ile706Thr | I706T | Sensibility |
| c.2125 G > R | p.Glu709Lys | E709K | Sensibility |
| c.2126 A > M | p.Glu709Ala | E709A | Sensibility |
| c.2174 C > Y | p.Thr725Met | T725M | Sensibility |
| c.2165 C > M | p.Ala722Glu | A722E | Sensibility |
| c.2235_2249 del | p.Glu746_Ala750del | Deletion E746-A750 | Sensibility |

TABLE 10-continued

List of genes mutations

| | | | |
|---|---|---|---|
| c.2236_2250 del | p.Glu746_Ala750del | Deletion E746-A750 | Sensibility |
| c.2240_2254del | p.Leu747_Thr751del | Deletion L747-T751 | Sensibility |
| c.2240_2257 del | p.Leu747_Pro753delinsSer | Deletion L747-P753 Insertion S | Sensibility |
| c.2237_2251del | p.Glu746_Thr751delinsAla | Deletion E746-T751 Insertion A | Sensibility |
| c.2239_2248delinsC | p.Leu747_Ala750delinsPro | Deletion L747-A750 Insertion P | Sensibility |
| c.2239_2251delinsC | p.Leu747_Thr751delinsPro | Deletion L747-T751 Insertion P | Sensibility |
| c.2237_2255 delinsT | p.Glu746_Ser752delinsVal | Deletion E746-S752 Insertion V | Sensibility |
| c.2214_2231dup | p.Ile740_Lys745dup | Duplication I740-K745 | Sensibility |
| c.2254_2277 del | p.Ser752_Ile759del | Deletion S752-I759 | Sensibility |
| c.2219_2236dup | p.Lys745_Glu746insValProValAlaIleLys | K745-E746 Insertion VPVAIK | Sensibility |
| c.2277 C > S | p.Ile759Met | I759M | Sensibility |
| c.2239_2256delinsCAA | p.Leu747_Ser752delinsGln | Deletion L747-S752 Insertion Q | Sensibility |
| c.2369C > Y | p.Thr790Met | T790M | Resistance |
| c.2317_2318insACC | p.His773dup | Duplication H773 | Resistance |
| c.2317_2318ins12 | p.Pro772_His773insLeuGlyAsnPro | P772-H773 insertion LGNP | Resistance |
| c.2315_2326dup | p.Pro772_Cys775dup | Duplication P772-C775 | Resistance |
| c.2300_2308 dup | p.Ala767_Val769dup | Duplication A767-V769 | Resistance |
| c.2303_2311 dup | p.Ser768_Asp770dup | Duplication S768-D770 | Resistance |
| c.2303_2311dup | p.Ser768_Asp770dup | Duplication S768-D770 | Resistance |
| c.2335G > T | p.Gly779Cys | G779C | Resistance |
| c.2573 T > K | p.Leu858Arg | L858R | Sensibility |
| c.2582 T > W | p.Leu861Gln | L861Q | Sensibility |

| Nucleotide | Protein | | |
|---|---|---|---|
| KRAS-NRAS | | | |
| c.34 G > K | p.Gly12Cys | G12C | |
| c.35 G > R | p.Gly12Asp | G12D | |
| c.35 G > K | p.Gly12Val | G12V | |
| c.35 G > S | p.Gly12Ala | G12A | |
| c.34 G > R | p.Gly12Ser | G12S | |
| c.34 G > S | p.Gly12Arg | G12R | |
| c.38 G > R | p.Gly13Asp | G13D | |
| c.37 G > K | p.Gly13Cys | G13C | |
| c.182 A > W | p.Gln61Leu | Q61L | |
| c.182 A > R | p.Gln61Arg | Q61R | |
| c.183 A > M | p.Gln61His | Q61H | |
| c.176 C > S | p.Ala59Gly | A59G | |
| c.175 G > R | p.Ala59Thr | A59T | |
| c.176 C > M | p.Ala59Glu | A59E | |
| ERBB2 | | | |
| c.2313_2324dup | p.Tyr772_Ala775dup | Duplication Y772-A775 | |
| c.2318_2319insGATGGCATACGT | p.Tyr772_Ala775dup | Duplication Y772-A775 | |
| c.2326_2327insTGT | p.Gly776delinsValCys | Deletion G776 Insertion VC | |
| c.2331_2339dup | p.Gly778_Pro780dup | Duplication G778-P780 | |
| PIK3CA | | | |
| c.1624 G > R | p.Glu542Lys | E542K | |
| c.1633 G > R | p.Glu545Lys | E545K | |
| c.3140A > R | p.His1047Arg | H1047R | |
| c.3140A > W | p.His1047Leu | H1047L | |
| c.2959 G > R | p.Ala987Thr | A987T | |
| c.3052G > A | p.Asp1018Asn | D1018N | |

TABLE 10-continued

List of genes mutations

| c.3080 C > Y | p.Ala1027Val | A1027V |
| c.3131A > R | p.Asn1044Ser | N1044S |

TABLE 11

List of miRNA

| Pathway | Symbol | GeneID | miRNAs |
|---|---|---|---|
| HER | EGF | 1950 | hsa-miR-4673; hsa-miR-485-5p; hsa-miR-647; hsa-miR-4742-5p; hsa-miR-4797-5p |
| | TGFA | 7039 | hsa-miR-3147; hsa-miR-1178; hsa-miR-626; hsa-miR-148a; hsa-miR-1182 |
| | AREG | 374 | hsa-miR-517a; hsa-miR-34c-5p; hsa-miR-4724-3p; hsa-miR-556-5p; hsa-miR-517b |
| | EREG | 2069 | hsa-miR-4713-5p; hsa-miR-4645-5p; hsa-miR-130a; hsa-miR-3661; hsa-miR-192 |
| | HBEGF | 1839 | hsa-miR-4736; hsa-miR-1207-5p; hsa-miR-4710; hsa-miR-3160-5p; hsa-miR-1271 |
| | BTC | 685 | hsa-miR-4715-3p; hsa-miR-1200; hsa-miR-4661-5p; hsa-miR-934; hsa-miR-488 |
| | NRG1 | 3084 | hsa-miR-4632; hsa-miR-1203; hsa-miR-552; hsa-miR-4736; hsa-miR-183 |
| | NRG2 | 9542 | hsa-miR-3196; hsa-miR-3934; hsa-miR-4746-5p; hsa-miR-296-5p; hsa-miR-4665-5p |
| | NRG4 | 145957 | hsa-miR-608; hsa-miR-1301; hsa-miR-4704-3p; hsa-miR-516b; hsa-miR-3681; |
| | EGFR | 1956 | hsa-miR-4417; hsa-miR-608; hsa-miR-885-3p; hsa-miR-4474-3p; hsa-miR-7; |
| | ERBB2 | 2064 | hsa-miR-331-3p; hsa-miR-4650-5p; hsa-miR-1972; hsa-miR-4533; hsa-miR-1296; |
| | ERBB3 | 2065 | hsa-miR-3199; hsa-miR-4505; hsa-miR-1287; hsa-miR-3153; hsa-miR-4290; |
| | ERBB4 | 2066 | hsa-miR-4469; hsa-miR-193a-3p; hsa-miR-642a; hsa-miR-3907; hsa-miR-3187-3p; |
| CDK4,6 | CDK4 | 1019 | hsa-miR-4747-5p; hsa-miR-198; hsa-miR-4728-5p; hsa-miR-765; hsa-miR-4280; |
| | CDK6 | 1021 | hsa-miR-3680; hsa-miR-3158-3p; hsa-miR-621; hsa-miR-644; hsa-miR-4252; |
| | CCND1 | 595 | hsa-miR-4707-3p; hsa-miR-3170; hsa-miR-1193; hsa-miR-4740-3p; hsa-miR-4632; |
| | CCND2 | 894 | hsa-miR-1468; hsa-miR-103b; hsa-miR-1205; hsa-miR-3065-3p; hsa-miR-4718; |
| | CCND3 | 896 | hsa-miR-4701-5p; hsa-miR-4739; hsa-miR-138; hsa-miR-4749-5p; hsa-miR-3154; |
| | CDKN2A, | 1029 | hsa-miR-663b; hsa-miR-675; hsa-miR-663; hsa-miR-1291; hsa-miR-621; |
| | CDKN2B | 1030 | hsa-miR-4308; hsa-miR-718; hsa-miR-1914; hsa-miR-451; hsa-miR-346; |
| | CCNE1 | 898 | hsa-miR-16; hsa-miR-874; hsa-miR-146b-3p; hsa-miR-4524; hsa-miR-3190; |
| | CCNE2 | 9134 | hsa-miR-449a; hsa-miR-370; hsa-miR-4460; hsa-miR-30b; hsa-miR-485-5p; |
| | RB1 | 5925 | hsa-miR-4703-5p; hsa-miR-4801; hsa-miR-4432; hsa-miR-7; hsa-miR-525-5p; |
| PLK/ AURK/ Kinesins | PLK1 | 5347 | hsa-miR-296-5p; hsa-miR-4660; hsa-miR-3665; hsa-miR-3166; hsa-miR-4778-5p; |
| | AURKA | 6790 | hsa-miR-3941; hsa-miR-4655-5p; hsa-miR-4756-5p; hsa-miR-3616-3p; hsa-miR-4757-5p; |
| | BORA | 79866 | hsa-miR-532-3p; hsa-miR-3162-3p; hsa-miR-4713-5p; hsa-miR-4758-3p; hsa-miR-3189-5p; |
| | ILK | 3611 | hsa-miR-1908; hsa-miR-4505; hsa-miR-744; hsa-miR-4425; hsa-miR-3150a-3p; |
| | KIF11 | 3832 | |
| ANGIOGENESIS | VEGFA | 7422 | hsa-miR-3668; hsa-miR-939; hsa-miR-29a; hsa-miR-339-5p; hsa-miR-16; |
| | VEGFB | 7423 | hsa-miR-2467-3p; hsa-miR-4649-3p; hsa-miR-4687-3p; hsa-miR-193a-5p; hsa-miR-1275; |
| | VEGFC | 7424 | hsa-miR-711; hsa-miR-3688-5p; hsa-miR-4687-3p; hsa-miR-128; hsa-miR-4318; |
| | VEGFD | 2277 | hsa-miR-320e; hsa-miR-135a; hsa-miR-7; hsa-miR-1184; hsa-miR-513b; |
| | FLT1 | 2321 | hsa-miR-148a; hsa-miR-5095; hsa-miR-335; hsa-miR-615-3p; hsa-miR-149; |
| | KDR | 3791 | hsa-miR-4435; hsa-miR-665; hsa-miR-370; hsa-miR-136; hsa-miR-138; |
| | FLT4 | 2324 | hsa-miR-4707-3p; hsa-miR-2861; hsa-miR-4728-5p; hsa-miR-2467-3p; hsa-miR-4783-5p; |
| | PDGFA | 5154 | hsa-miR-4690-5p; hsa-miR-3917; hsa-miR-4706; hsa-miR-4768-5p; hsa-miR-412; |
| | PDGFB | 5155 | hsa-miR-3202; hsa-miR-1909; hsa-miR-3689d; hsa-miR-4271; hsa-miR-625; |
| | PDGFRA | 5156 | hsa-miR-3691-3p; hsa-miR-4471; hsa-miR-34a; hsa-miR-663b; hsa-miR-3117-3p; |
| | PDGFRB | 5159 | hsa-miR-1915; hsa-miR-4292; hsa-miR-4731-5p; hsa-miR-637; hsa-miR-486-3p; |
| | Kit | 3815 | hsa-miR-4254; hsa-miR-671-5p; hsa-miR-1193; hsa-miR-222; hsa-miR-4485; |
| ANGIOPOIETINS | THBS1 | 7057 | hsa-miR-3074-5p; hsa-miR-4786-3p; hsa-miR-3177-5p; hsa-miR-634; hsa-miR-4443; |
| | TGFB1 | 7040 | hsa-miR-3196; hsa-miR-663; hsa-miR-296-5p; hsa-miR-3943; hsa-miR-3183; |
| | ANGPT1 | 284 | hsa-miR-153; hsa-miR-4643; hsa-miR-4755-5p; hsa-miR-4789-3p; hsa-miR-3682-3p; |
| | ANGPT2 | 285 | hsa-miR-135a; hsa-miR-1182; hsa-miR-513c; hsa-miR-597; hsa-miR-4251; |
| | ANGPTL1 | 9068 | hsa-miR-3688-5p; hsa-miR-586; hsa-miR-4480; hsa-miR-544; hsa-miR-194; |
| | ANGPT4 | 51378 | hsa-miR-296-5p; hsa-miR-4690-3p; hsa-miR-422a; hsa-miR-431; hsa-miR-665; |
| | TIE1 | 7075 | hsa-miR-3151; hsa-miR-4447; hsa-miR-4723-5p; hsa-miR-486-3p; hsa-miR-4287; |
| | TEK | 7010 | hsa-miR-4713-5p; hsa-miR-300; hsa-miR-4690-3p; hsa-miR-150; hsa-miR-148a; |
| IMMUNO-Modulator | CD274 or PDL1 | 29126 | hsa-miR-4443; hsa-miR-3117-3p; hsa-miR-138; hsa-miR-339-5p; hsa-miR-1273; |
| | PDCD1LG2 | 80380 | hsa-miR-20a; hsa-miR-548an; hsa-miR-4661-5p; hsa-miR-3133; hsa-miR-3910; |
| | PDCD1 | 5133 | hsa-miR-4290; hsa-miR-1291; hsa-miR-4763-5p; hsa-miR-2861; hsa-miR-661; |
| | CTLA4 | 1493 | hsa-miR-324-5p; hsa-miR-502-5p; hsa-miR-4254; hsa-miR-3121-5p; hsa-miR-1587; |
| | LAG3 | 3902 | hsa-miR-4515; hsa-miR-1269; hsa-miR-4529-3p; hsa-miR-4270; hsa-miR-628-5p; |
| PI3K | PIK3CA | 5290 | hsa-miR-4450; hsa-miR-4529-3p; hsa-miR-302d; hsa-miR-3910; hsa-miR-490-5p; |
| | PIK3CB | 5291 | |
| | PIK3CD | 5293 | hsa-miR-4537; hsa-miR-2355-5p; hsa-miR-523; hsa-miR-7; hsa-miR-484; |
| | PIK3CG | 5294 | hsa-miR-370; hsa-miR-3135b; hsa-miR-1976; hsa-miR-1276; hsa-miR-3672; |
| | PIK3C2B | 5287 | hsa-miR-361-3p; hsa-miR-4728-5p; hsa-miR-4740-3p; hsa-miR-3612; hsa-miR-4314; |
| | PRKCB | 5579 | hsa-miR-4691-5p; hsa-miR-448; hsa-miR-7; hsa-miR-668; hsa-miR-27a; |
| | PRKCA | 5578 | hsa-miR-4757-5p; hsa-miR-4685-5p; hsa-miR-4706; hsa-miR-1275; hsa-miR-4525; |

TABLE 11-continued

List of miRNA

| Pathway | Symbol | GeneID | miRNAs |
|---|---|---|---|
| | PIK3R1 | 5295 | hsa-miR-4789-3p; hsa-miR-4789-5p; hsa-miR-4646-3p; hsa-miR-1184; hsa-miR-4660; |
| | PIK3R2 | 5296 | hsa-miR-4723-5p; hsa-miR-3180; hsa-miR-4447; hsa-miR-3960; hsa-miR-3151; |
| | PIK3R3 | 8503 | hsa-miR-4725-3p; hsa-miR-4435; hsa-miR-4715-5p; hsa-miR-2115; hsa-miR-4313; |
| MET | HGF | 3082 | hsa-miR-4520a-3p; hsa-miR-764; hsa-miR-4716-3p; hsa-miR-1288; hsa-miR-4710; |
| | MET | 4233 | hsa-miR-3074-5p; hsa-miR-2682; hsa-miR-34c-5p; hsa-miR-182; hsa-miR-1269b; |
| | AXL | 558 | hsa-miR-3142; hsa-miR-4728-5p; hsa-miR-924; hsa-miR-3689c; hsa-miR-432; |
| | MST1R | 4486 | hsa-miR-296-5p; hsa-miR-218; hsa-miR-1286; hsa-miR-3126-5p; hsa-miR-4284; |
| MEK | MAP2K1 | 5604 | hsa-miR-4323; hsa-miR-4423-3p; hsa-miR-758; hsa-miR-34a; hsa-miR-15b; |
| | MAP2K2 | 5605 | hsa-miR-1181; hsa-miR-1207-3p; hsa-miR-744; hsa-miR-663; hsa-miR-4786-5p; |
| | MAP2K3 | 5606 | hsa-miR-4313; hsa-miR-3151; hsa-miR-4283; hsa-miR-4540; hsa-miR-4270; |
| | MAP2K4 | 6416 | hsa-miR-4663; hsa-miR-25; hsa-miR-3065-3p; hsa-miR-4649-5p; hsa-miR-627; |
| | MAP3K1 | 4214 | hsa-miR-4286; hsa-miR-1225-3p; hsa-miR-4703-3p; hsa-miR-544; hsa-miR-887; |
| | MAP3K2 | 10746 | hsa-miR-519d; hsa-miR-651; hsa-miR-587; hsa-miR-34c-3p; hsa-miR-2909; |
| | MAP3K3 | 4215 | hsa-miR-661; hsa-miR-1225-3p; hsa-miR-544b; hsa-miR-3922-3p; hsa-miR-4505; |
| | MAP3K4 | 4216 | hsa-miR-1204; hsa-miR-3129-5p; hsa-miR-5047; hsa-miR-3691-3p; hsa-miR-3064-3p; |
| ERK | MAPK3 | 5595 | hsa-miR-4270; hsa-miR-486-3p; hsa-miR-483-5p; hsa-miR-608; hsa-miR-1291; |
| | MAPK1 | 5594 | hsa-miR-4667-5p; hsa-miR-4459; hsa-miR-4271; hsa-miR-4799-5p; hsa-miR-2110; |
| | KSR1 | 8844 | hsa-miR-331-3p; hsa-miR-4440; hsa-miR-4291; hsa-miR-4660; hsa-miR-876-3p; |
| | MAPK11 | 5600 | hsa-miR-4640-3p; hsa-miR-296-5p; hsa-miR-4292; hsa-miR-4532; hsa-miR-4685-5p; |
| ANTI-APOPTOSIS | BCL2 | 596 | hsa-miR-448; hsa-miR-4691-3p; hsa-miR-3199; hsa-miR-3943; hsa-miR-342-3p; |
| | BCL2L1 | 598 | hsa-miR-4447; hsa-miR-608; hsa-miR-4728-5p; hsa-miR-4649-3p; hsa-miR-4700-5p; |
| | BIRC5 | 332 | hsa-miR-542-3p; hsa-miR-3940-3p; hsa-miR-4660; hsa-miR-1225-3p; hsa-miR-1273; |
| | XIAP | 331 | hsa-miR-377; hsa-miR-3150a-3p; hsa-miR-3175; hsa-miR-5095; hsa-miR-3664-5p; |
| | BAK1 | 578 | hsa-miR-4419a; hsa-miR-125b; hsa-miR-4667-5p; hsa-miR-1909; hsa-miR-4739; |
| FGF | FGF1 | 2246 | hsa-miR-4297; hsa-miR-3155; hsa-miR-1909; hsa-miR-566; hsa-miR-2355-5p; |
| | FGF2 | 2247 | hsa-miR-195; hsa-miR-4524; hsa-miR-503; hsa-miR-646; hsa-miR-3607-5p; |
| | FGF3 | 2248 | hsa-miR-3173-5p; hsa-miR-4487; hsa-miR-760; hsa-miR-4722-3p; hsa-miR-4758-3p; |
| | FGF4 | 2249 | hsa-miR-4671-5p; hsa-miR-3679-3p; hsa-miR-4290; hsa-miR-361-3p; hsa-miR-767-5p; |
| | FGF5 | 2250 | hsa-miR-4435; hsa-miR-4655-5p; hsa-miR-4288; hsa-miR-4463; hsa-miR-4704-3p; |
| | FGF6 | 2251 | hsa-miR-4677-3p; hsa-miR-548q; hsa-miR-138; hsa-miR-639; hsa-miR-1322; |
| | FGF7 | 2252 | hsa-miR-4762-5p; hsa-miR-486-5p; hsa-miR-195; hsa-miR-3920; hsa-miR-1253; |
| | FGF8 | 2253 | hsa-miR-3120-3p; hsa-miR-545; hsa-miR-491-5p; hsa-miR-361-3p; hsa-miR-4720-5p; |
| | FGF9 | 2254 | hsa-miR-1273c; hsa-miR-140-5p; hsa-miR-423-3p; hsa-miR-3157-5p; hsa-miR-3683; |
| | FGF10 | 2255 | |
| | FGF11 | 2256 | hsa-miR-4667-3p; hsa-miR-4469; hsa-miR-3192; hsa-miR-3661; hsa-miR-3649; |
| | FGF12 | 2257 | hsa-miR-4747-5p; hsa-miR-3202; hsa-miR-4533; hsa-miR-4633-3p; hsa-miR-197; |
| | FGF13 | 2258 | hsa-miR-1262; hsa-miR-3675-5p; hsa-miR-1185; hsa-miR-512-3p; hsa-miR-4421; |
| | FGF14 | 2259 | hsa-miR-4663; hsa-miR-188-3p; hsa-miR-4299; hsa-miR-4690-5p; hsa-miR-4691-3p; |
| | FGFR1 | 2260 | hsa-miR-4530; hsa-miR-4728-5p; hsa-miR-515-3p; hsa-miR-1208; hsa-miR-4667-5p; |
| | FGFR2 | 2263 | hsa-miR-515-5p; hsa-miR-3177-3p; hsa-miR-423-3p; hsa-miR-4789-3p; hsa-miR-3675-5p; |
| | FGFR3 | 2261 | hsa-miR-296-5p; hsa-miR-4793-3p; hsa-miR-4746-3p; hsa-miR-3918; hsa-miR-1291; |
| | FGFR4 | 2264 | hsa-miR-3177-3p; hsa-miR-4726-5p; hsa-miR-1225-3p; hsa-miR-378g; hsa-miR-564; |
| mTOR -AKT-PTEN- | mTor | 2475 | hsa-miR-767-3p; hsa-miR-4762-3p; hsa-miR-496; hsa-miR-1233; hsa-miR-1229; |
| | AKT1 | 207 | hsa-miR-1915; hsa-miR-4721; hsa-miR-4162-3p; hsa-miR-4738-5p; hsa-miR-4723-5p; |
| | AKT2 | 208 | hsa-miR-4716-3p; hsa-miR-29b; hsa-miR-4278; hsa-miR-3943; hsa-miR-3065-3p; |
| | PTEN | 5728 | hsa-miR-642b; hsa-miR-486-5p; hsa-miR-148a; hsa-miR-3944-5p; hsa-miR-3691-5p; |
| Modulators | TSC1 | 7248 | hsa-miR-130a; hsa-miR-1537; hsa-miR-637; hsa-miR-3141; hsa-miR-3684; |
| MTKPT | TSC2 | 7249 | hsa-miR-4420; hsa-miR-654-3p; hsa-miR-4722-5p; hsa-miR-615-5p; hsa-miR-3922-5p; |
| | STK11 | 6794 | hsa-miR-663; hsa-miR-744; hsa-miR-4723-5p; hsa-miR-3960; hsa-miR-615-5p; |
| | PIM1 | 5292 | hsa-miR-4749-3p; hsa-miR-761; hsa-miR-3689a-3p; hsa-miR-331-3p; hsa-miR-4436b-3p; |
| | PIM2 | 11040 | hsa-miR-361-3p; hsa-miR-4532; hsa-miR-3654; hsa-miR-4645-5p; hsa-miR-4768-3p; |
| | PIM3 | 415116 | hsa-miR-3195; hsa-miR-4697-5p; hsa-miR-654-5p; hsa-miR-4467; hsa-miR-637; |
| RAS | KRAS | 3845 | hsa-miR-3923; hsa-miR-4323; hsa-miR-4447; hsa-miR-513a-5p; hsa-miR-548ag; |
| | NRAS | 4893 | hsa-miR-502-5p; hsa-miR-1296; hsa-miR-1324; hsa-miR-3120-3p; hsa-miR-4271; |
| | HRAS | 3265 | hsa-miR-3667-3p; hsa-miR-4728-5p; hsa-miR-4292; hsa-miR-4532; hsa-miR-663; |
| RAF | RAF1 | 5894 | hsa-miR-1291; hsa-miR-7; hsa-miR-3126-5p; hsa-miR-296-5p; hsa-miR-764; |
| | BRAF | 673 | hsa-miR-617; hsa-miR-2110; hsa-miR-3977; hsa-miR-1182; hsa-miR-1289; |
| TELOMERASE | TERT | 7015 | hsa-miR-4650-5p; hsa-miR-491-5p; hsa-miR-4651; hsa-miR-3687; hsa-miR-4292; |
| | TERC | 7012 | |
| | TEP1 | 7011 | hsa-miR-1911; hsa-miR-3132; hsa-miR-136; hsa-miR-2861; hsa-miR-31; |
| | HSP90AA1 | 3320 | hsa-miR-4753-5p; hsa-miR-632; hsa-miR-519e; hsa-miR-3679-3p; hsa-miR-134; |
| | DKC1 | 1736 | hsa-miR-3194-3p; hsa-miR-621; hsa-miR-3620; hsa-miR-646; hsa-miR-4279; |
| | PTGES3 | 10728 | hsa-miR-3189-5p; hsa-miR-3135; hsa-miR-4266; hsa-miR-3678-3p; hsa-miR-4286; |

TABLE 11-continued

List of miRNA

| Pathway | Symbol | GeneID | miRNAs |
|---|---|---|---|
| IGF & Warburg | IGF1 | 3479 | hsa-miR-483-3p; hsa-miR-1275; hsa-miR-4435; hsa-miR-488; hsa-miR-625; |
| | IGF2 | 3481 | hsa-miR-4447; hsa-miR-491-5p; hsa-miR-210; hsa-miR-3191; hsa-miR-3144-5p; |
| | IGF1R | 3480 | hsa-miR-4746-3p; hsa-miR-4784; hsa-miR-4763-3p; hsa-miR-4327; hsa-miR-3157-5p; |
| | IGF2R | 3482 | hsa-miR-4667-3p; hsa-miR-653; hsa-miR-4707-3p; hsa-miR-4736; hsa-miR-548an; |
| | INSR | 3643 | hsa-miR-2467-5p; hsa-miR-3975; hsa-miR-3188; hsa-miR-4707-3p; hsa-miR-4290; |
| | IRS1 | 3667 | hsa-miR-660; hsa-miR-541; hsa-miR-4462; hsa-miR-544b; hsa-miR-183; |
| | PKM2 | 5315 | hsa-miR-762; hsa-miR-625; hsa-miR-612; hsa-miR-4675; hsa-miR-4665-5p; |
| WNT | CDH1 | 999 | hsa-miR-4640-3p; hsa-miR-4711-5p; hsa-miR-3689c; hsa-miR-2355-5p; hsa-miR-1296; |
| | CTNNA1 | 1495 | hsa-miR-1288; hsa-miR-4440; hsa-miR-4515; hsa-miR-4705; hsa-miR-9; |
| | CTNNB1 | 1499 | hsa-miR-3688-5p; hsa-miR-3162-3p; hsa-miR-4776-5p; hsa-miR-4496; hsa-miR-3619-3p; |
| | WNT1 | 7471 | hsa-miR-4488; hsa-miR-4784; hsa-miR-4695-5p; hsa-miR-4644; hsa-miR-4689; |
| | FZD1 | 8321 | hsa-miR-4269; hsa-miR-4769-5p; hsa-miR-1275; hsa-miR-1324; hsa-miR-4279; |
| | WNT5A | 7474 | hsa-miR-2110; hsa-miR-4691-5p; hsa-miR-876-5p; hsa-miR-3127-3p; hsa-miR-4656; |
| | WNT5B | 81029 | hsa-miR-4316; hsa-miR-4258; hsa-miR-2909; hsa-miR-1296; hsa-miR-486-3p; |
| | FZD5 | 7855 | hsa-miR-296-5p; hsa-miR-3943; hsa-miR-188-3p; hsa-miR-3661; hsa-miR-3672; |
| | WIF1 | 11197 | hsa-miR-1972; hsa-miR-3938; hsa-miR-548v; hsa-miR-140-3p; hsa-miR-3977; |
| | DKK1 | 22943 | hsa-miR-493; hsa-miR-4639-3p; hsa-miR-4727-5p; hsa-miR-4678; hsa-miR-934; |
| PARP | PARP1 | 142 | hsa-miR-891b; hsa-miR-4536; hsa-miR-4451; hsa-miR-555; hsa-miR-7; |
| | BRCA1 | 672 | hsa-miR-615-5p; hsa-miR-3667-3p; hsa-miR-4446-3p; hsa-miR-760; hsa-miR-4656; |
| | XRCC1 | 7515 | hsa-miR-589; hsa-miR-4477a; |
| | RAD54L | 8438 | hsa-miR-4713-5p; hsa-miR-1225-3p; hsa-miR-3918; hsa-miR-3667-3p; hsa-miR-1291; |
| | RAD54B | 25788 | hsa-miR-587; hsa-miR-4268; hsa-miR-548s; hsa-miR-3926; hsa-miR-1; |
| | ATM | 472 | hsa-miR-892b; hsa-miR-193a-3p; hsa-miR-4735-3p; hsa-miR-4736; hsa-miR-4262; |
| | ATR | 545 | hsa-miR-3613-5p; hsa-miR-383; hsa-miR-4760-5p; hsa-miR-140-3p; hsa-miR-586; |
| | CHEK1 | 1111 | hsa-miR-2355-5p; hsa-miR-541; hsa-miR-1286; hsa-miR-4733-3p; hsa-miR-16; |
| | CHEK2 | 11200 | hsa-miR-3118; hsa-miR-759; hsa-miR-4276; hsa-miR-3938; hsa-miR-943; |
| | WEE1 | 7465 | hsa-miR-4716-3p; hsa-miR-4723-5p; hsa-miR-424; hsa-miR-3120-3p; hsa-miR-4278; |
| HDAC | HDAC1 | 3065 | has-miR-4284; hsa-miR-4292; hsa-miR-4271; hsa-miR-3126-5p; hsa-miR-584; |
| | HDAC2 | 3066 | hsa-miR-362-5p; hsa-miR-3977; hsa-miR-3194-3p; hsa-miR-4662a-5p; hsa-miR-4720-5p; |
| | HDAC3 | 8841 | hsa-miR-3189-3p; hsa-miR-1261; hsa-miR-326; hsa-miR-1302; hsa-miR-4308; |
| | HDAC4 | 9759 | hsa-miR-4292; hsa-miR-4313; hsa-miR-4728-5p; hsa-miR-1225-3p; hsa-miR-4316; |
| | HDAC5 | 10014 | hsa-miR-331-3p; hsa-miR-671-5p; hsa-miR-4498; hsa-miR-296-5p; hsa-miR-4505; |
| JAK-STAT | JAK1 | 3716 | hsa-miR-4252; hsa-miR-4437; hsa-miR-4520a-3p; hsa-miR-323b-5p; hsa-miR-4674; |
| | JAK2 | 3717 | hsa-miR-4720-5p; hsa-miR-4468; hsa-miR-3120-3p; hsa-miR-4777-3p; hsa-miR-568; |
| | STAT1 | 6772 | hsa-miR-4682; hsa-miR-1252; hsa-miR-3119; hsa-miR-4697-3p; hsa-miR-2682; |
| | STAT2 | 6773 | hsa-miR-665; hsa-miR-3202; hsa-miR-4292; hsa-miR-4313; hsa-miR-1289; |
| | STAT3 | 6774 | hsa-miR-1299; hsa-miR-4753-5p; hsa-miR-1184; hsa-miR-874; hsa-miR-5047; |
| | SOCS1 | 8651 | hsa-miR-4645-5p; hsa-miR-556-3p; hsa-miR-331-3p; hsa-miR-4716-3p; hsa-miR-324-5p; |
| HEDGEHOG | SHH | 6469 | hsa-miR-1471; hsa-miR-4749-3p; hsa-miR-4313; |
| | PTCH1 | 5727 | hsa-miR-4757-5p; hsa-miR-564; hsa-miR-1262; hsa-miR-767-3p; hsa-miR-125a-3p; |
| | SMO | 6608 | hsa-miR-370; hsa-miR-4690-3p; hsa-miR-4758-3p; hsa-miR-423-3p; hsa-miR-1915; |
| | STK36 | 27148 | hsa-miR-571; hsa-miR-3192; hsa-miR-581; hsa-miR-920; hsa-miR-4715-5p; |
| | PRKACA | 5566 | hsa-miR-4723-5p; hsa-miR-4665-5p; hsa-miR-608; hsa-miR-423-5p; hsa-miR-625; |
| | SUFU | 51684 | hsa-miR-3184; hsa-miR-4487; hsa-miR-4688; hsa-miR-4728-5p; hsa-miR-4741; |
| | GLI1 | 2735 | hsa-miR-3943; hsa-miR-4279; hsa-miR-4292; hsa-miR-361-3p; hsa-miR-4533; |
| DNA REPAIR | ERCC1 | 2067 | hsa-miR-661; hsa-miR-1913; hsa-miR-323-5p; hsa-miR-1972; hsa-miR-1268; |
| | RAD52 | 5893 | hsa-miR-3922-3p; hsa-miR-4725-3p; hsa-miR-342-3p; hsa-miR-542-3p; hsa-miR-4303; |
| | XRCC4 | 7518 | hsa-miR-361-5p; hsa-miR-380; hsa-miR-4520a-3p; hsa-miR-3121-5p; hsa-miR-2355-3p; |
| | RAD51 | 5888 | hsa-miR-198; hsa-miR-532-3p; hsa-miR-606; hsa-miR-4430; hsa-miR-4432; |
| | BRCA1 | 672 | hsa-miR-615-5p; hsa-miR-3667-3p; hsa-miR-4446-3p; hsa-miR-760; hsa-miR-4656; |
| | NEDD8 | 4738 | hsa-miR-4713-3p; hsa-miR-4726-5p; hsa-miR-665; hsa-miR-1285; hsa-miR-1322; |
| | NAE1 | 8883 | hsa-miR-4524; hsa-miR-646; hsa-miR-4660; hsa-miR-582-5p; hsa-miR-603; |
| NOTCH | NOTCH1 | 4851 | hsa-miR-4313; hsa-miR-4268; hsa-miR-449a; hsa-miR-139-5p; hsa-miR-4727-5p; |
| | Adam17 | 6868 | hsa-miR-507; hsa-miR-3918; hsa-miR-4687-5p; hsa-miR-3651; hsa-miR-1827; |
| | PSEN1 | 5663 | hsa-miR-3065-3p; hsa-miR-4697-3p; hsa-miR-3120-5p; hsa-miR-4303; hsa-miR-488; |
| | NCSTN | 23385 | hsa-miR-339-5p; hsa-miR-4654; hsa-miR-1321; hsa-miR-4648; hsa-miR-3657; |
| | JAG1 | 182 | hsa-miR-4692; hsa-miR-1273g; hsa-miR-920; hsa-miR-4661-5p; hsa-miR-4283; |
| | SRRT | 51593 | hsa-miR-4700-3p; hsa-miR-3190; hsa-miR-487b; hsa-miR-520f; hsa-miR-3929; |
| | APH1A | 51107 | hsa-miR-3679-3p; hsa-miR-198; hsa-miR-3173-3p; hsa-miR-4685-5p; hsa-miR-3131; |
| Others | ROS1 | 6098 | hsa-miR-4693-3p; hsa-miR-4653-3p; hsa-miR-33a; hsa-miR-606; hsa-miR-3659; |
| | ALK | 238 | hsa-miR-642a; hsa-miR-646; hsa-miR-4764-3p; hsa-miR-1271; hsa-miR-4713-3p; |
| | RET | 5979 | hsa-miR-544; hsa-miR-4652-5p; hsa-miR-510; hsa-miR-31; hsa-miR-3622b-5p; |
| | UBA1 | 7317 | hsa-miR-4716-3p; hsa-miR-762; hsa-miR-4640-5p; hsa-miR-3202; hsa-miR-31; |

TABLE 12

| | KRAS | EFGR | PIK3CA | BRAF | ERBB2 | P53 |
|---|---|---|---|---|---|---|
| 1 | c.34G > K p.Gly12Cys (G12C) | WT | WT | WT | WT | 80_SNP_A > G_R-Arg_exon6, 102_deletion_C_exon8 |
| 2 | c.35G > K p.Gly12Val (G12V) | WT | WT | WT | WT | 39_G > A_Met > Ile_exon7, 75_G > C_exon7 |
| 3 | WT | WT | WT | WT | WT | 47_G > T_Ser > Ile_exon7, 51_C > A_Ser > Ser_exon7 |
| 7 | WT | WT | WT | WT | c.2883T > G p.Ile961Met (I961M) AGVGD: Class C0_exon 24 | WT |
| 8 | c.34G > K p.Gly12Cys (G12C) | WT | WT | WT | WT | WT |
| 12 | c.35G > R p.Gly12Asp (G12D) | WT | WT | WT | WT | WT |
| 15 | WT | WT | WT | WT | WT | 63_C > T_Gly > Gly_exon7 |
| 20 | c.34G > K p.Gly12Cys (G12C) | WT | WT | WT | WT | WT |
| 23 | c.35G > K p.Gly12Val (G12V) | WT | WT | WT | WT | WT |
| 25 | WT | WT | c.30750 > T p. = rs17849079 | WT | WT | 139_A > G_Glu > Gly_exon5 |
| 29 | c.35G > K p.Gly12Val (G12V) | WT | WT | WT | WT | WT |
| 30 | WT | WT | WT | WT | WT | 17_G > T_exon10 |
| 32 | c.35G > R p.Gly12Asp (G12D) | WT | WT | WT | WT | WT |
| 33 | WT | WT | WT | WT | WT | 177_G > T_Asp > Tyr_exon5 |
| 34 | WT | WT | WT | WT | WT | 96_G > C_Val > Leu_exon5 |
| 36 | | WT | WT | nd | WT | 62_G > A_Gly > Asp_exon7, and 88_insertion_G_exon7 |
| 39 | c.34G > K p.Gly12Cys (G12C) | WT | WT | WT | WT | WT |
| 40 | c.34G > K p.Gly12Cys (G12C) | WT | WT | WT | WT | 94_G > A_Arg > His_exon5 |
| 42 | WT | WT | WT | WT | WT | 55_G > C_Gly > Ala_exon8 |
| 46 | c.35G > K p.Gly12Val (G12V) | WT | WT | WT | WT | WT |
| 47 | WT | c.2184 + 19G > R Non Codant rs17337107 | WT | WT | WT | 57_A > T_Arg > Stop_exon8 |
| 49 | WT | c.2184 + 19G > R Non Codant rs17337107 | WT | WT | WT | WT |
| 50 | WT | WT | WT | WT | WT | 58_insertion_G, 75_SNP_G > A_Arg > Arg_exon7 |
| 51 | WT | WT | WT | WT | WT | 42_A > G_Lys > Glu_exon5 |
| 57 | WT | c.2184 + 19G > R Non Codant rs17337107 | WT | WT | WT | WT |
| 58 | WT | WT | c.2937-96A > C Non Codant | WT | WT | WT |
| 59 | WT | WT | WT | c.1799T > W p.Val600Glu (V600E) | wt | WT |
| 61 | WT | WT | WT | WT | WT | 58_G > A_Gly > Ser_exon6, 65_T > A_Met > Lys_exon7, 70_G > A?_Gly? > Arg?_exon7, 129_C > T_exon7 |
| 62 | WT | c.2184 + 19G > A Non Codant rs17337107 | WT | WT | WT | WT |
| 68 | WT | WT | wt | wt | wt | 47_G > T_Ser > Ile_exon7, 51_C > A_Ser > Ser_exon7, 83_C > A?_Pro? > His?_exon7 |
| 70 | WT | WT | WT | WT | WT | 119_G > T_Lys > Asn_exon5 |

TABLE 12-continued

| | Mutational status | | | | |
|---|---|---|---|---|---|
| KRAS | EFGR | PIK3CA | BRAF | ERBB2 | P53 |
| 71 WT | c.2320_2321ins3bp (CAC) p.Val774delinsAlaLeu exon 20 | WT | WT | WT | WT |
| 72 c.35G > S p.Gly12Ala (G12A) | WT | WT | WT | WT | 152_insertion_T_exon5 |
| 74 WT | c.2184 + 19G > R Non Codant rs17337107 | WT | WT | WT | WT |
| 75 WT | WT | WT | WT | WT | 83_T > C_exon7 |
| 76 WT | WT | WT | WT | WT | 55_A > G_Tyr > Cys_exon6 |
| 78 c.34G > K p.Gly12Cys (G12C) | WT | WT | WT | WT | WT |
| 80 WT | WT | WT | WT | WT | 163_A > T_His > Leu_exon5 |
| 83 c.34G > K p.Gly12Cys (G12C) | WT | WT | WT | WT | WT |
| 84 WT | WT | WT | WT | WT | 96_G > T_Val > Phe_exon5 |
| 88 WT | WT | WT | WT | WT | 158_C > G_exon7 |
| 91 c.34G > K p.Gly12Cys (G12C) | c.2184 + 19G > R Non Codant rs17337107 | WT | WT | WT | 80_SNP_A > G_R-Arg_exon6, 101_A > G_Glu > Gly_exon7, 106_T > A_Ser > Thr_exon7, 142_C > G_exon7 |
| 92 WT | c.2215_2229del15bp p.Lys739_Ala743de exon 20 | WT | WT | WT | WT |
| 93 WT | c.2156G > C p.Gly719Ala (G719A) VAR_026086 exon 18 c.2303G > T p.Ser768Ile (S768I) AGVGD: Class C65 exon 20 | WT | WT | WT | WT |
| 94 c.34G > K p.Gly12Cys (G12C) | WT | WT | WT | WT | WT |
| 96 c.34G > K p.Gly12Cys (G12C) | c.2184 + 19G > R Non Codant rs17337107 | WT | WT | WT | WT |
| 102 WT | WT | WT | WT | WT | 54_T > C_Tyr > His_exon6 |
| 103 WT | c.2184 + 19G > R Non Codant rs17337107 | WT | WT | WT | WT |
| 104 c.35G > K p.Gly12Val (G12V) | WT | WT | WT | WT | WT |
| 107 WT | WT | WT | WT | WT | 70_C > T_Arg > Trp_exon7, 71_SNP_G > A_exon7 |
| 108 WT | WT | WT | WT | WT | 26deletion_T_exon9 |
| 111 WT | c.2313_2314ins9bp (CCCCAGGCG) p.Pro772_His773insGlnAlaPro_expn 20 | WT | WT | WT | WT |
| 113 c.34G > K p.Gly12Cys (G12C) | WT | WT | WT | WT | WT |
| 114 WT | WT | WT | WT | WT | WT |
| 115 WT | c.2184 + 19G > R Non Codant rs17337107 | WT | WT | WT | WT |
| 118 WT | WT | WT | WT | WT | 99_C > G_Arg > Gly_exon5 |
| 121 c.183A > W p.Gln61His (Q61H) rs17851045 exon 3 | WT | WT | WT | WT | 92_C > T_exon5, 104_C < T_exon5, 128_C > G_Ser > Arg_exon8, |

TABLE 13

Calculated scores
Wherein P means Patient, (1) refers to a score calculated based on mRNA expression, (2) refers to a score calculated based on mutation and mRNA expression, (3) refers to a score calculated based on mutation, mRNA expression, and miRNA expression, and (4) refers to a score calculated based on mutation, mRNA expression, miRNA expression and Copy Number Variation.

| P | 1 | 2 | 3 | 4 | 1 | 2 | 3 | 4 | 1 | 2 | 3 | 4 | 1 | 2 | 3 | 4 | 1 | 2 | 3 | 4 |
|---|---|---|---|---|---|---|---|---|---|---|---|---|---|---|---|---|---|---|---|---|
| | | Her | | | | CDK 4-6 | | | | PLK_AURKA_Kinesins | | | | ANGIOGENESIS | | | | ANGIOPOIETINS | | |
| 1 | 2 | 2 | 2 | 1 | 1 | 4 | 4 | 3 | 3 | 7 | 7 | 7 | 7 | 5 | 5 | 6 | 5 | 2 | 2 | 2 | 2 |
| 2 | 2 | 2 | 2 | 5 | 5 | 6 | 6 | 6 | 6 | 7 | 7 | 5 | 5 | 8 | 8 | 7 | 7 | 6 | 6 | 5 | 5 |

TABLE 13-continued

Calculated scores
Wherein P means Patient, (1) refers to a score calculated based on mRNA expression, (2) refers to a score calculated based on mutation and mRNA expression, (3) refers to a score calculated based on mutation, mRNA expression, and miRNA expression, and (4) refers to a score calculated based on mutation, mRNA expression, miRNA expression and Copy Number Variation.

| P | | | | | | | | | | | | | | | | | | | | |
|---|---|---|---|---|---|---|---|---|---|---|---|---|---|---|---|---|---|---|---|---|
| 3  | 3  | 3  | 9  | 9  | 6  | 6  | 4  | 4  | 7  | 7  | 8  | 8  | 3  | 3  | 1  | 1  | 1  | 1  | 1  | 1 |
| 4  | 1  | 1  | 2  | 2  | 4  | 4  | 2  | 2  | 5  | 5  | 5  | 5  | 5  | 5  | 5  | 5  | 8  | 8  | 8  | 8 |
| 5  | 9  | 9  | 7  | 8  | 10 | 10 | 10 | 10 | 3  | 3  | 3  | 3  | 8  | 8  | 9  | 9  | 8  | 8  | 8  | 8 |
| 6  | 7  | 7  | 8  | 8  | 8  | 8  | 7  | 7  | 8  | 8  | 8  | 8  | 10 | 10 | 10 | 10 | 9  | 9  | 9  | 9 |
| 7  | 7  | 10 | 10 | 10 | 1  | 1  | 1  | 1  | 1  | 1  | 1  | 1  | 2  | 2  | 3  | 3  | 7  | 7  | 5  | 5 |
| 8  | 8  | 8  | 5  | 5  | 10 | 10 | 10 | 10 | 10 | 10 | 9  | 9  | 9  | 9  | 8  | 8  | 4  | 4  | 2  | 2 |
| 9  | 4  | 4  | 5  | 5  | 1  | 1  | 1  | 1  | 3  | 3  | 3  | 3  | 1  | 1  | 1  | 1  | 2  | 2  | 1  | 1 |
| 10 | 1  | 1  | 1  | 1  | 2  | 2  | 1  | 1  | 1  | 1  | 1  | 1  | 4  | 4  | 3  | 2  | 5  | 5  | 3  | 3 |
| 11 | 9  | 9  | 7  | 7  | 4  | 4  | 3  | 3  | 6  | 6  | 6  | 6  | 9  | 9  | 9  | 9  | 10 | 10 | 10 | 10 |
| 12 | 4  | 4  | 7  | 7  | 3  | 3  | 2  | 2  | 1  | 1  | 1  | 1  | 6  | 6  | 4  | 4  | 6  | 6  | 5  | 5 |
| 13 | 10 | 10 | 10 | 10 | 9  | 9  | 9  | 9  | 9  | 9  | 9  | 9  | 6  | 6  | 6  | 7  | 1  | 1  | 1  | 1 |
| 14 | 8  | 8  | 9  | 9  | 2  | 2  | 3  | 3  | 1  | 1  | 1  | 1  | 3  | 3  | 5  | 6  | 9  | 9  | 10 | 10 |
| 15 | 4  | 4  | 2  | 2  | 10 | 10 | 9  | 9  | 10 | 10 | 10 | 10 | 1  | 1  | 1  | 1  | 2  | 2  | 1  | 4 |
| 16 | 6  | 6  | 7  | 6  | 3  | 3  | 5  | 5  | 5  | 5  | 6  | 6  | 5  | 5  | 6  | 5  | 9  | 9  | 10 | 10 |
| 17 | 7  | 7  | 4  | 4  | 7  | 7  | 8  | 8  | 7  | 7  | 7  | 7  | 8  | 8  | 8  | 8  | 6  | 6  | 6  | 6 |
| 18 | 10 | 10 | 10 | 10 | 8  | 8  | 10 | 9  | 8  | 8  | 9  | 9  | 8  | 8  | 9  | 9  | 5  | 5  | 7  | 7 |
| 19 | 10 | 10 | 10 | 10 | 8  | 8  | 9  | 9  | 6  | 6  | 7  | 7  | 5  | 5  | 6  | 6  | 5  | 5  | 6  | 6 |
| 20 | 1  | 1  | 1  | 1  | 4  | 4  | 4  | 4  | 9  | 9  | 9  | 9  | 3  | 3  | 1  | 1  | 8  | 8  | 7  | 7 |
| 21 | 7  | 7  | 8  | 8  | 5  | 5  | 5  | 5  | 2  | 2  | 2  | 2  | 2  | 2  | 2  | 2  | 8  | 8  | 6  | 6 |
| 22 | 9  | 9  | 9  | 8  | 5  | 5  | 5  | 5  | 6  | 6  | 5  | 5  | 6  | 6  | 5  | 5  | 5  | 5  | 5  | 5 |
| 23 | 7  | 7  | 4  | 4  | 5  | 5  | 6  | 6  | 5  | 5  | 5  | 5  | 10 | 10 | 10 | 10 | 10 | 10 | 10 | 10 |
| 24 | 7  | 7  | 6  | 6  | 8  | 8  | 9  | 9  | 8  | 8  | 8  | 9  | 1  | 1  | 1  | 1  | 1  | 1  | 1  | 1 |
| 25 | 1  | 1  | 2  | 2  | 10 | 10 | 10 | 10 | 10 | 10 | 10 | 10 | 1  | 1  | 1  | 1  | 1  | 1  | 2  | 1 |
| 26 | 4  | 4  | 4  | 6  | 8  | 8  | 7  | 10 | 8  | 8  | 7  | 7  | 10 | 10 | 10 | 10 | 10 | 10 | 10 | 10 |
| 27 | 1  | 1  | 2  | 2  | 10 | 10 | 10 | 10 | 3  | 3  | 4  | 4  | 8  | 8  | 9  | 9  | 9  | 9  | 9  | 9 |
| 28 | 2  | 2  | 1  | 1  | 6  | 6  | 5  | 5  | 10 | 10 | 10 | 10 | 4  | 10 | 10 | 10 | 4  | 4  | 3  | 3 |
| 29 | 6  | 6  | 7  | 7  | 6  | 6  | 8  | 8  | 6  | 6  | 6  | 6  | 6  | 6  | 7  | 7  | 7  | 7  | 7  | 7 |
| 30 | 7  | 7  | 5  | 5  | 9  | 9  | 9  | 9  | 10 | 10 | 10 | 10 | 6  | 6  | 6  | 6  | 8  | 8  | 8  | 8 |
| 31 | 10 | 10 | 10 | 10 | 4  | 4  | 6  | 6  | 4  | 4  | 5  | 5  | 3  | 3  | 3  | 3  | 10 | 10 | 10 | 10 |
| 32 | 5  | 5  | 5  | 5  | 3  | 3  | 4  | 4  | 1  | 1  | 1  | 1  | 5  | 5  | 6  | 6  | 5  | 5  | 5  | 5 |
| 33 | 8  | 8  | 9  | 9  | 3  | 3  | 6  | 6  | 4  | 4  | 4  | 4  | 2  | 2  | 3  | 3  | 1  | 1  | 1  | 1 |
| 34 | 2  | 2  | 2  | 3  | 10 | 10 | 10 | 10 | 10 | 10 | 10 | 10 | 1  | 1  | 2  | 3  | 4  | 4  | 6  | 6 |
| 35 | 8  | 8  | 6  | 6  | 8  | 8  | 5  | 5  | 7  | 7  | 7  | 7  | 10 | 10 | 10 | 10 | 10 | 10 | 9  | 8 |
| 36 | 3  | 3  | 2  | 3  | 10 | 10 | 10 | 10 | 3  | 3  | 3  | 3  | 9  | 9  | 8  | 8  | 4  | 4  | 2  | 3 |
| 37 | 6  | 6  | 7  | 7  | 4  | 4  | 5  | 5  | 3  | 3  | 3  | 3  | 2  | 2  | 2  | 2  | 6  | 6  | 7  | 7 |
| 38 | 4  | 4  | 4  | 4  | 7  | 7  | 8  | 8  | 4  | 4  | 4  | 4  | 4  | 4  | 4  | 4  | 2  | 2  | 1  | 1 |
| 39 | 10 | 10 | 10 | 10 | 5  | 5  | 3  | 3  | 7  | 7  | 6  | 6  | 7  | 7  | 6  | 6  | 9  | 9  | 8  | 8 |
| 40 | 4  | 4  | 4  | 4  | 2  | 2  | 2  | 2  | 1  | 1  | 1  | 1  | 8  | 8  | 8  | 8  | 2  | 2  | 4  | 4 |
| 41 | 5  | 5  | 3  | 3  | 5  | 5  | 5  | 5  | 3  | 3  | 3  | 3  | 8  | 8  | 7  | 7  | 9  | 9  | 9  | 9 |
| 42 | 10 | 10 | 10 | 10 | 10 | 10 | 10 | 10 | 5  | 5  | 6  | 6  | 9  | 9  | 9  | 9  | 6  | 6  | 4  | 4 |
| 43 | 3  | 3  | 5  | 5  | 4  | 4  | 5  | 5  | 9  | 9  | 7  | 7  | 8  | 8  | 8  | 8  | 10 | 10 | 10 | 10 |
| 44 | 8  | 8  | 7  | 7  | 5  | 5  | 6  | 6  | 4  | 4  | 5  | 5  | 8  | 8  | 9  | 9  | 3  | 3  | 4  | 4 |
| 45 | 6  | 6  | 6  | 6  | 7  | 7  | 7  | 7  | 7  | 7  | 8  | 8  | 4  | 4  | 4  | 4  | 3  | 3  | 3  | 3 |
| 46 | 5  | 5  | 3  | 2  | 1  | 1  | 2  | 2  | 1  | 1  | 2  | 2  | 2  | 2  | 3  | 3  | 3  | 3  | 5  | 5 |
| 47 | 10 | 10 | 10 | 10 | 9  | 9  | 8  | 8  | 8  | 8  | 8  | 8  | 5  | 5  | 4  | 4  | 1  | 1  | 3  | 2 |
| 48 | 4  | 4  | 6  | 6  | 6  | 6  | 7  | 7  | 9  | 9  | 8  | 8  | 5  | 5  | 6  | 6  | 5  | 5  | 6  | 6 |
| 49 | 5  | 10 | 10 | 10 | 8  | 8  | 7  | 7  | 5  | 5  | 5  | 5  | 4  | 4  | 3  | 3  | 8  | 8  | 7  | 7 |
| 50 | 1  | 1  | 10 | 10 | 7  | 7  | 7  | 7  | 9  | 9  | 9  | 10 | 9  | 9  | 8  | 8  | 8  | 8  | 9  | 9 |
| 51 | 3  | 3  | 3  | 3  | 4  | 4  | 6  | 6  | 9  | 9  | 9  | 9  | 2  | 2  | 2  | 2  | 2  | 2  | 3  | 3 |
| 52 | 8  | 8  | 7  | 7  | 4  | 4  | 7  | 7  | 1  | 1  | 1  | 1  | 1  | 10 | 10 | 10 | 2  | 2  | 4  | 4 |
| 53 | 3  | 3  | 3  | 3  | 2  | 2  | 1  | 1  | 3  | 3  | 4  | 4  | 2  | 2  | 2  | 2  | 3  | 3  | 5  | 5 |
| 54 | 9  | 9  | 9  | 9  | 1  | 1  | 1  | 1  | 2  | 2  | 2  | 2  | 3  | 3  | 3  | 3  | 6  | 6  | 6  | 6 |
| 55 | 7  | 7  | 8  | 10 | 5  | 5  | 4  | 4  | 4  | 4  | 4  | 4  | 7  | 7  | 7  | 7  | 9  | 9  | 9  | 8 |
| 56 | 9  | 9  | 8  | 9  | 3  | 3  | 4  | 4  | 7  | 7  | 8  | 8  | 5  | 5  | 6  | 6  | 7  | 7  | 8  | 8 |
| 57 | 4  | 10 | 10 | 10 | 9  | 9  | 9  | 9  | 8  | 8  | 8  | 8  | 7  | 7  | 7  | 7  | 6  | 6  | 5  | 5 |
| 58 | 10 | 10 | 9  | 9  | 3  | 3  | 6  | 6  | 2  | 2  | 2  | 2  | 4  | 4  | 4  | 4  | 6  | 6  | 4  | 4 |
| 59 | 9  | 10 | 10 | 10 | 7  | 7  | 7  | 7  | 2  | 2  | 2  | 2  | 2  | 2  | 3  | 3  | 8  | 8  | 7  | 7 |
| 60 | 9  | 9  | 9  | 9  | 1  | 1  | 2  | 2  | 1  | 1  | 1  | 1  | 2  | 2  | 3  | 3  | 3  | 3  | 6  | 6 |
| 61 | 4  | 4  | 3  | 3  | 4  | 4  | 2  | 2  | 9  | 9  | 8  | 8  | 10 | 10 | 10 | 10 | 9  | 9  | 8  | 9 |
| 62 | 8  | 10 | 10 | 10 | 8  | 8  | 6  | 6  | 9  | 9  | 8  | 8  | 5  | 5  | 5  | 6  | 1  | 1  | 2  | 2 |
| 63 | 6  | 6  | 8  | 8  | 3  | 3  | 3  | 3  | 3  | 3  | 4  | 4  | 2  | 10 | 10 | 10 | 7  | 7  | 7  | 7 |
| 64 | 2  | 2  | 1  | 1  | 9  | 9  | 7  | 7  | 5  | 5  | 6  | 6  | 10 | 10 | 9  | 9  | 9  | 9  | 8  | 8 |
| 65 | 3  | 3  | 3  | 3  | 6  | 6  | 4  | 4  | 5  | 5  | 4  | 4  | 3  | 3  | 2  | 2  | 3  | 3  | 2  | 2 |
| 66 | 1  | 1  | 1  | 1  | 2  | 2  | 2  | 2  | 1  | 1  | 1  | 1  | 5  | 5  | 5  | 5  | 7  | 7  | 6  | 6 |
| 67 | 7  | 7  | 7  | 7  | 1  | 1  | 1  | 1  | 2  | 2  | 2  | 2  | 9  | 9  | 8  | 8  | 4  | 4  | 6  | 6 |
| 68 | 6  | 10 | 10 | 10 | 1  | 1  | 1  | 1  | 6  | 6  | 7  | 7  | 3  | 3  | 3  | 3  | 2  | 2  | 2  | 2 |
| 69 | 1  | 1  | 4  | 4  | 1  | 1  | 4  | 4  | 2  | 2  | 2  | 2  | 8  | 8  | 9  | 9  | 6  | 6  | 8  | 8 |
| 70 | 10 | 10 | 10 | 9  | 8  | 8  | 8  | 8  | 6  | 6  | 6  | 6  | 10 | 10 | 10 | 10 | 4  | 4  | 3  | 3 |
| 71 | 6  | 10 | 10 | 10 | 1  | 1  | 1  | 1  | 4  | 4  | 3  | 3  | 7  | 7  | 8  | 8  | 8  | 8  | 8  | 9 |
| 72 | 5  | 5  | 6  | 6  | 5  | 5  | 7  | 7  | 2  | 2  | 3  | 3  | 10 | 10 | 10 | 10 | 9  | 9  | 9  | 9 |
| 73 | 10 | 10 | 10 | 10 | 8  | 8  | 8  | 8  | 10 | 10 | 10 | 10 | 1  | 1  | 1  | 1  | 10 | 10 | 10 | 10 |
| 74 | 2  | 10 | 10 | 10 | 9  | 9  | 9  | 9  | 10 | 10 | 10 | 10 | 1  | 1  | 1  | 1  | 4  | 4  | 4  | 3 |
| 75 | 10 | 10 | 8  | 8  | 7  | 7  | 5  | 5  | 7  | 7  | 7  | 7  | 10 | 10 | 10 | 10 | 7  | 7  | 4  | 4 |

TABLE 13-continued

Calculated scores
Wherein P means Patient, (1) refers to a score calculated based on mRNA expression, (2) refers to a score calculated based on mutation and mRNA expression, (3) refers to a score calculated based on mutation, mRNA expression, and miRNA expression, and (4) refers to a score calculated based on mutation, mRNA expression, miRNA expression and Copy Number Variation.

| | 1 | 2 | 3 | 4 | 1 | 2 | 3 | 4 | 1 | 2 | 3 | 4 | 1 | 2 | 3 | 4 | 1 | 2 | 3 | 4 |
|---|---|---|---|---|---|---|---|---|---|---|---|---|---|---|---|---|---|---|---|---|
| 76 | 3 | 3 | 8 | 7 | 10 | 10 | 10 | 9 | 8 | 8 | 9 | 9 | 7 | 7 | 8 | 8 | 4 | 4 | 4 | 4 |
| 77 | 1 | 1 | 1 | 1 | 3 | 3 | 2 | 2 | 2 | 2 | 2 | 2 | 6 | 6 | 5 | 5 | 7 | 7 | 6 | 6 |
| 78 | 8 | 8 | 1 | 1 | 10 | 10 | 10 | 10 | 6 | 6 | 7 | 7 | 1 | 1 | 1 | 1 | 4 | 4 | 3 | 3 |
| 79 | 9 | 9 | 8 | 9 | 9 | 9 | 8 | 8 | 8 | 8 | 9 | 9 | 4 | 4 | 4 | 4 | 6 | 6 | 7 | 7 |
| 80 | 2 | 2 | 3 | 3 | 6 | 6 | 3 | 3 | 10 | 10 | 8 | 8 | 1 | 1 | 1 | 1 | 1 | 1 | 1 | 3 |
| 81 | 9 | 9 | 8 | 8 | 3 | 3 | 2 | 2 | 2 | 2 | 2 | 2 | 7 | 10 | 10 | 10 | 10 | 10 | 10 | 10 |
| 82 | 1 | 1 | 2 | 2 | 1 | 1 | 1 | 1 | 3 | 3 | 3 | 3 | 10 | 10 | 10 | 10 | 5 | 5 | 5 | 5 |
| 83 | 10 | 10 | 7 | 7 | 1 | 1 | 1 | 1 | 9 | 9 | 7 | 7 | 9 | 9 | 8 | 8 | 4 | 4 | 2 | 1 |
| 84 | 5 | 5 | 5 | 4 | 4 | 4 | 4 | 4 | 6 | 6 | 7 | 7 | 3 | 3 | 4 | 4 | 3 | 3 | 2 | 2 |
| 85 | 4 | 4 | 5 | 5 | 3 | 3 | 2 | 2 | 4 | 4 | 5 | 5 | 6 | 6 | 5 | 5 | 3 | 3 | 2 | 2 |
| 86 | 5 | 5 | 4 | 7 | 9 | 9 | 9 | 9 | 8 | 8 | 9 | 8 | 4 | 4 | 4 | 4 | 9 | 9 | 9 | 8 |
| 87 | 6 | 6 | 9 | 9 | 2 | 2 | 4 | 4 | 3 | 3 | 2 | 2 | 8 | 8 | 8 | 8 | 8 | 8 | 9 | 9 |
| 88 | 6 | 6 | 7 | 7 | 7 | 7 | 6 | 6 | 9 | 9 | 10 | 10 | 4 | 4 | 5 | 5 | 3 | 3 | 5 | 5 |
| 89 | 3 | 3 | 3 | 3 | 2 | 2 | 5 | 5 | 6 | 6 | 6 | 6 | 6 | 6 | 7 | 7 | 3 | 3 | 5 | 5 |
| 90 | 4 | 4 | 5 | 4 | 10 | 10 | 10 | 10 | 7 | 7 | 9 | 9 | 1 | 1 | 2 | 2 | 2 | 2 | 4 | 4 |
| 91 | 2 | 10 | 10 | 10 | 2 | 2 | 2 | 2 | 1 | 1 | 1 | 1 | 5 | 5 | 6 | 6 | 2 | 2 | 5 | 5 |
| 92 | 8 | 10 | 10 | 10 | 7 | 7 | 8 | 8 | 4 | 4 | 4 | 4 | 2 | 2 | 2 | 2 | 10 | 10 | 9 | 9 |
| 93 | 9 | 10 | 10 | 10 | 7 | 7 | 8 | 8 | 2 | 2 | 3 | 3 | 6 | 6 | 7 | 7 | 3 | 3 | 2 | 2 |
| 94 | 5 | 5 | 6 | 6 | 1 | 1 | 1 | 1 | 1 | 1 | 1 | 1 | 10 | 10 | 9 | 9 | 10 | 10 | 10 | 10 |
| 95 | 3 | 3 | 1 | 1 | 9 | 9 | 9 | 9 | 9 | 9 | 10 | 10 | 4 | 4 | 4 | 5 | 1 | 1 | 3 | 3 |
| 96 | 7 | 10 | 10 | 10 | 2 | 2 | 2 | 2 | 2 | 2 | 1 | 1 | 6 | 6 | 5 | 5 | 4 | 4 | 3 | 3 |
| 97 | 2 | 2 | 1 | 1 | 6 | 6 | 4 | 4 | 5 | 5 | 4 | 4 | 3 | 3 | 2 | 2 | 5 | 5 | 2 | 2 |
| 98 | 2 | 2 | 2 | 2 | 2 | 2 | 3 | 3 | 3 | 3 | 2 | 2 | 7 | 7 | 7 | 7 | 7 | 7 | 8 | 8 |
| 99 | 3 | 3 | 6 | 5 | 3 | 3 | 1 | 1 | 4 | 4 | 3 | 3 | 9 | 9 | 9 | 9 | 6 | 6 | 3 | 2 |
| 100 | 8 | 8 | 6 | 6 | 9 | 9 | 8 | 8 | 7 | 7 | 6 | 6 | 6 | 6 | 5 | 5 | 1 | 1 | 1 | 1 |
| 101 | 8 | 8 | 9 | 9 | 7 | 7 | 9 | 8 | 2 | 2 | 2 | 2 | 7 | 7 | 7 | 7 | 7 | 7 | 7 | 7 |
| 102 | 4 | 4 | 4 | 4 | 10 | 10 | 9 | 9 | 9 | 9 | 9 | 9 | 7 | 7 | 6 | 6 | 7 | 7 | 9 | 9 |
| 103 | 5 | 10 | 10 | 10 | 5 | 5 | 6 | 6 | 8 | 8 | 9 | 9 | 5 | 5 | 4 | 4 | 2 | 2 | 1 | 1 |
| 104 | 8 | 8 | 10 | 10 | 9 | 9 | 10 | 10 | 10 | 10 | 10 | 10 | 3 | 3 | 5 | 4 | 5 | 5 | 7 | 7 |
| 105 | 1 | 1 | 2 | 2 | 5 | 5 | 6 | 6 | 5 | 5 | 6 | 6 | 7 | 7 | 7 | 7 | 2 | 2 | 4 | 4 |
| 106 | 6 | 6 | 5 | 5 | 8 | 8 | 8 | 8 | 6 | 6 | 6 | 6 | 10 | 10 | 10 | 10 | 10 | 10 | 10 | 8 |
| 107 | 6 | 6 | 3 | 3 | 7 | 7 | 5 | 5 | 7 | 7 | 5 | 5 | 4 | 4 | 2 | 2 | 9 | 9 | 8 | 8 |
| 108 | 2 | 2 | 2 | 2 | 6 | 6 | 4 | 4 | 5 | 5 | 4 | 4 | 10 | 10 | 10 | 10 | 5 | 5 | 1 | 1 |
| 109 | 9 | 9 | 8 | 8 | 2 | 2 | 3 | 3 | 3 | 3 | 3 | 3 | 8 | 8 | 8 | 8 | 8 | 8 | 9 | 9 |
| 110 | 5 | 5 | 4 | 4 | 3 | 3 | 3 | 3 | 8 | 8 | 7 | 7 | 9 | 9 | 9 | 9 | 7 | 7 | 8 | 9 |
| 111 | 7 | 10 | 10 | 10 | 6 | 6 | 5 | 5 | 6 | 6 | 5 | 5 | 7 | 7 | 5 | 5 | 1 | 1 | 1 | 1 |
| 112 | 6 | 6 | 3 | 3 | 8 | 8 | 7 | 7 | 4 | 4 | 3 | 3 | 4 | 4 | 3 | 3 | 5 | 5 | 4 | 4 |
| 113 | 10 | 10 | 9 | 9 | 6 | 6 | 6 | 6 | 10 | 10 | 10 | 10 | 9 | 9 | 10 | 10 | 6 | 6 | 3 | 3 |
| 114 | 3 | 3 | 3 | 2 | 4 | 4 | 3 | 3 | 4 | 4 | 4 | 4 | 6 | 6 | 7 | 7 | 10 | 10 | 10 | 10 |
| 115 | 5 | 10 | 10 | 10 | 6 | 6 | 4 | 4 | 4 | 4 | 4 | 4 | 3 | 3 | 4 | 4 | 7 | 7 | 7 | 7 |
| 116 | 5 | 5 | 1 | 1 | 10 | 10 | 9 | 10 | 10 | 10 | 10 | 10 | 2 | 2 | 1 | 1 | 3 | 3 | 4 | 4 |
| 117 | 3 | 3 | 5 | 5 | 5 | 5 | 3 | 3 | 7 | 7 | 6 | 6 | 7 | 7 | 6 | 6 | 8 | 8 | 7 | 7 |
| 118 | 7 | 7 | 6 | 6 | 9 | 9 | 10 | 10 | 8 | 8 | 8 | 8 | 9 | 9 | 9 | 9 | 4 | 4 | 6 | 6 |
| 119 | 2 | 2 | 2 | 2 | 2 | 2 | 3 | 3 | 10 | 10 | 10 | 9 | 1 | 1 | 1 | 1 | 1 | 1 | 3 | 2 |
| 120 | 1 | 1 | 2 | 2 | 7 | 7 | 8 | 7 | 6 | 6 | 5 | 5 | 3 | 3 | 4 | 4 | 10 | 10 | 10 | 10 |
| 121 | 9 | 9 | 9 | 8 | 5 | 5 | 7 | 7 | 5 | 5 | 5 | 5 | 9 | 9 | 10 | 10 | 5 | 5 | 6 | 6 |

| | 1 | 2 | 3 | 4 | 1 | 2 | 3 | 4 | 1 | 2 | 3 | 4 | 1 | 2 | 3 | 4 | 1 | 2 | 3 | 4 |
|---|---|---|---|---|---|---|---|---|---|---|---|---|---|---|---|---|---|---|---|---|
| P | IMMUNO-Modulator | | | | PI3K | | | | MET | | | | MEK | | | | ERK | | | |
| 1 | 7 | 7 | 8 | 8 | 4 | 4 | 3 | 2 | 4 | 4 | 4 | 4 | 9 | 9 | 9 | 9 | 1 | 1 | 3 | 3 |
| 2 | 10 | 10 | 10 | 10 | 4 | 4 | 7 | 7 | 10 | 10 | 10 | 10 | 4 | 4 | 2 | 2 | 1 | 1 | 1 | 1 |
| 3 | 6 | 6 | 3 | 3 | 3 | 3 | 1 | 1 | 2 | 2 | 1 | 1 | 5 | 5 | 3 | 3 | 7 | 7 | 1 | 1 |
| 4 | 8 | 8 | 8 | 8 | 9 | 9 | 8 | 7 | 3 | 3 | 2 | 2 | 9 | 9 | 8 | 8 | 10 | 10 | 9 | 9 |
| 5 | 7 | 7 | 8 | 8 | 2 | 2 | 5 | 4 | 8 | 8 | 7 | 7 | 7 | 7 | 7 | 7 | 6 | 6 | 5 | 5 |
| 6 | 5 | 5 | 6 | 9 | 8 | 8 | 9 | 10 | 5 | 5 | 6 | 6 | 4 | 4 | 4 | 4 | 5 | 5 | 7 | 7 |
| 7 | 5 | 5 | 4 | 3 | 3 | 3 | 2 | 1 | 4 | 4 | 3 | 3 | 6 | 6 | 5 | 5 | 4 | 4 | 2 | 2 |
| 8 | 9 | 9 | 8 | 8 | 4 | 4 | 3 | 3 | 9 | 9 | 9 | 9 | 8 | 8 | 7 | 6 | 4 | 4 | 5 | 5 |
| 9 | 6 | 6 | 6 | 6 | 6 | 6 | 6 | 6 | 5 | 5 | 5 | 5 | 3 | 3 | 4 | 4 | 4 | 4 | 2 | 6 |
| 10 | 8 | 8 | 7 | 7 | 9 | 9 | 4 | 4 | 6 | 6 | 5 | 5 | 9 | 9 | 8 | 8 | 2 | 2 | 4 | 4 |
| 11 | 8 | 8 | 8 | 8 | 5 | 5 | 2 | 5 | 5 | 5 | 6 | 5 | 7 | 7 | 4 | 7 | 2 | 2 | 3 | 3 |
| 12 | 6 | 6 | 4 | 4 | 4 | 4 | 2 | 2 | 4 | 4 | 3 | 3 | 5 | 5 | 3 | 3 | 5 | 5 | 4 | 4 |
| 13 | 8 | 8 | 7 | 6 | 6 | 6 | 3 | 7 | 5 | 5 | 5 | 5 | 9 | 9 | 7 | 7 | 2 | 2 | 7 | 6 |
| 14 | 4 | 4 | 6 | 5 | 1 | 1 | 2 | 2 | 3 | 3 | 5 | 5 | 5 | 5 | 8 | 8 | 2 | 2 | 2 | 2 |
| 15 | 3 | 3 | 2 | 2 | 10 | 10 | 8 | 10 | 8 | 8 | 7 | 9 | 5 | 5 | 3 | 3 | 6 | 6 | 2 | 2 |
| 16 | 8 | 8 | 9 | 9 | 2 | 2 | 6 | 5 | 5 | 5 | 6 | 6 | 1 | 1 | 2 | 2 | 1 | 1 | 9 | 9 |
| 17 | 9 | 9 | 9 | 9 | 2 | 2 | 2 | 2 | 8 | 8 | 7 | 7 | 8 | 8 | 9 | 9 | 4 | 4 | 8 | 7 |
| 18 | 10 | 10 | 10 | 10 | 2 | 2 | 9 | 8 | 10 | 10 | 10 | 10 | 8 | 8 | 10 | 10 | 5 | 5 | 5 | 5 |
| 19 | 7 | 7 | 8 | 7 | 8 | 8 | 9 | 8 | 10 | 10 | 10 | 10 | 9 | 9 | 9 | 9 | 3 | 3 | 7 | 6 |
| 20 | 4 | 4 | 2 | 2 | 6 | 6 | 3 | 3 | 10 | 10 | 10 | 10 | 2 | 2 | 2 | 2 | 8 | 8 | 5 | 4 |
| 21 | 5 | 5 | 3 | 3 | 6 | 6 | 9 | 8 | 9 | 9 | 9 | 9 | 7 | 7 | 5 | 4 | 1 | 1 | 10 | 10 |
| 22 | 6 | 6 | 5 | 5 | 1 | 1 | 1 | 1 | 8 | 8 | 6 | 6 | 2 | 2 | 2 | 2 | 4 | 4 | 6 | 6 |
| 23 | 10 | 10 | 10 | 10 | 2 | 2 | 4 | 3 | 9 | 9 | 9 | 9 | 5 | 5 | 7 | 7 | 4 | 4 | 10 | 10 |

TABLE 13-continued

Calculated scores
Wherein P means Patient, (1) refers to a score calculated based on mRNA expression, (2) refers to a score calculated based on mutation and mRNA expression, (3) refers to a score calculated based on mutation, mRNA expression, and miRNA expression, and (4) refers to a score calculated based on mutation, mRNA expression, miRNA expression and Copy Number Variation.

| P | (1) | (1) | (1) | (1) | (2) | (2) | (2) | (2) | (3) | (3) | (3) | (3) | (4) | (4) | (4) | (4) | | | | |
|---|---|---|---|---|---|---|---|---|---|---|---|---|---|---|---|---|---|---|---|---|
| 24 | 4 | 4 | 5 | 7 | 1 | 1 | 2 | 2 | 7 | 7 | 8 | 8 | 5 | 5 | 6 | 6 | 8 | 8 | 6 | 8 |
| 25 | 1 | 1 | 1 | 1 | 10 | 10 | 10 | 10 | 2 | 2 | 4 | 4 | 4 | 4 | 5 | 5 | 9 | 9 | 9 | 10 |
| 26 | 8 | 8 | 9 | 8 | 4 | 4 | 6 | 6 | 2 | 2 | 5 | 8 | 4 | 4 | 6 | 6 | 3 | 3 | 1 | 1 |
| 27 | 10 | 10 | 10 | 10 | 6 | 6 | 8 | 7 | 1 | 1 | 2 | 2 | 8 | 8 | 10 | 10 | 4 | 4 | 3 | 3 |
| 28 | 3 | 3 | 5 | 4 | 5 | 5 | 3 | 2 | 4 | 4 | 4 | 7 | 2 | 2 | 3 | 3 | 8 | 8 | 5 | 5 |
| 29 | 10 | 10 | 10 | 10 | 9 | 9 | 10 | 10 | 10 | 10 | 10 | 10 | 5 | 5 | 8 | 9 | 4 | 4 | 4 | 4 |
| 30 | 4 | 4 | 3 | 3 | 8 | 8 | 6 | 8 | 7 | 7 | 6 | 6 | 7 | 7 | 6 | 6 | 10 | 10 | 10 | 10 |
| 31 | 6 | 6 | 7 | 7 | 8 | 8 | 8 | 7 | 9 | 9 | 9 | 9 | 6 | 6 | 7 | 7 | 6 | 6 | 9 | 8 |
| 32 | 4 | 4 | 5 | 5 | 5 | 5 | 4 | 4 | 7 | 7 | 7 | 7 | 2 | 2 | 3 | 3 | 5 | 5 | 4 | 4 |
| 33 | 4 | 4 | 4 | 4 | 6 | 6 | 7 | 6 | 10 | 10 | 10 | 10 | 3 | 3 | 4 | 4 | 2 | 2 | 1 | 1 |
| 34 | 5 | 5 | 6 | 9 | 7 | 7 | 8 | 9 | 6 | 6 | 7 | 7 | 1 | 1 | 4 | 4 | 10 | 10 | 10 | 10 |
| 35 | 4 | 4 | 5 | 5 | 7 | 7 | 5 | 4 | 6 | 6 | 5 | 4 | 10 | 10 | 8 | 8 | 10 | 10 | 10 | 9 |
| 36 | 3 | 3 | 2 | 2 | 3 | 3 | 1 | 1 | 9 | 9 | 9 | 8 | 3 | 3 | 2 | 2 | 4 | 4 | 7 | 7 |
| 37 | 6 | 6 | 6 | 6 | 9 | 9 | 10 | 9 | 7 | 7 | 8 | 8 | 5 | 5 | 7 | 7 | 6 | 6 | 4 | 4 |
| 38 | 2 | 2 | 2 | 2 | 1 | 1 | 1 | 1 | 1 | 1 | 1 | 1 | 2 | 2 | 3 | 3 | 3 | 3 | 2 | 2 |
| 39 | 10 | 10 | 9 | 9 | 8 | 3 | 7 | 7 | 8 | 8 | 7 | 7 | 6 | 6 | 5 | 5 | 6 | 6 | 3 | 3 |
| 40 | 2 | 2 | 3 | 3 | 1 | 1 | 2 | 2 | 4 | 4 | 4 | 4 | 2 | 2 | 3 | 3 | 1 | 1 | 4 | 4 |
| 41 | 3 | 3 | 3 | 3 | 7 | 7 | 7 | 6 | 6 | 6 | 6 | 5 | 8 | 8 | 7 | 7 | 5 | 5 | 2 | 2 |
| 42 | 10 | 10 | 10 | 10 | 8 | 8 | 7 | 6 | 8 | 8 | 7 | 7 | 10 | 10 | 10 | 10 | 7 | 7 | 3 | 3 |
| 43 | 1 | 1 | 1 | 1 | 1 | 1 | 2 | 1 | 1 | 1 | 2 | 2 | 2 | 2 | 2 | 2 | 6 | 6 | 5 | 5 |
| 44 | 7 | 7 | 7 | 6 | 2 | 2 | 6 | 6 | 10 | 10 | 10 | 10 | 5 | 5 | 5 | 5 | 4 | 4 | 7 | 7 |
| 45 | 10 | 10 | 10 | 10 | 10 | 10 | 9 | 10 | 1 | 1 | 3 | 3 | 10 | 10 | 10 | 10 | 8 | 8 | 6 | 6 |
| 46 | 6 | 6 | 6 | 6 | 4 | 4 | 5 | 5 | 5 | 5 | 6 | 6 | 8 | 8 | 9 | 9 | 2 | 2 | 8 | 8 |
| 47 | 4 | 4 | 4 | 4 | 10 | 10 | 10 | 10 | 9 | 9 | 9 | 9 | 6 | 6 | 6 | 6 | 8 | 8 | 5 | 5 |
| 48 | 9 | 9 | 9 | 9 | 6 | 6 | 6 | 9 | 5 | 5 | 6 | 6 | 1 | 1 | 1 | 1 | 8 | 8 | 10 | 10 |
| 49 | 10 | 10 | 9 | 9 | 10 | 10 | 8 | 8 | 6 | 6 | 4 | 4 | 6 | 6 | 4 | 4 | 6 | 6 | 4 | 4 |
| 50 | 9 | 9 | 9 | 9 | 10 | 10 | 10 | 10 | 1 | 1 | 3 | 3 | 9 | 9 | 9 | 9 | 7 | 7 | 5 | 4 |
| 51 | 9 | 9 | 10 | 10 | 4 | 4 | 6 | 5 | 8 | 8 | 9 | 10 | 3 | 3 | 6 | 5 | 3 | 3 | 10 | 10 |
| 52 | 2 | 2 | 4 | 4 | 3 | 3 | 4 | 3 | 8 | 8 | 8 | 8 | 10 | 10 | 10 | 10 | 1 | 1 | 1 | 1 |
| 53 | 7 | 7 | 6 | 6 | 7 | 7 | 7 | 6 | 5 | 5 | 7 | 6 | 7 | 7 | 6 | 6 | 7 | 7 | 3 | 3 |
| 54 | 5 | 5 | 3 | 3 | 7 | 7 | 5 | 4 | 7 | 7 | 7 | 7 | 4 | 4 | 4 | 4 | 6 | 6 | 10 | 10 |
| 55 | 5 | 5 | 3 | 3 | 5 | 5 | 5 | 4 | 8 | 8 | 8 | 8 | 1 | 1 | 1 | 1 | 7 | 7 | 5 | 5 |
| 56 | 1 | 1 | 1 | 1 | 6 | 6 | 7 | 9 | 6 | 6 | 5 | 7 | 1 | 1 | 1 | 1 | 3 | 3 | 2 | 2 |
| 57 | 10 | 10 | 9 | 9 | 10 | 10 | 10 | 10 | 5 | 5 | 6 | 6 | 8 | 8 | 8 | 8 | 9 | 9 | 8 | 8 |
| 58 | 9 | 9 | 8 | 8 | 5 | 10 | 10 | 10 | 9 | 9 | 9 | 9 | 3 | 3 | 2 | 2 | 5 | 5 | 3 | 3 |
| 59 | 4 | 4 | 4 | 4 | 9 | 9 | 7 | 7 | 4 | 4 | 3 | 3 | 6 | 6 | 6 | 6 | 3 | 3 | 3 | 3 |
| 60 | 2 | 2 | 3 | 3 | 9 | 9 | 10 | 9 | 9 | 9 | 9 | 9 | 9 | 9 | 10 | 10 | 1 | 1 | 5 | 5 |
| 61 | 1 | 1 | 1 | 1 | 5 | 5 | 1 | 5 | 3 | 3 | 1 | 1 | 10 | 10 | 8 | 10 | 10 | 10 | 9 | 10 |
| 62 | 3 | 3 | 2 | 2 | 10 | 10 | 10 | 10 | 4 | 4 | 3 | 3 | 8 | 8 | 8 | 6 | 6 | 6 | 1 | 1 |
| 63 | 8 | 8 | 8 | 7 | 3 | 3 | 7 | 6 | 7 | 7 | 8 | 8 | 9 | 9 | 9 | 9 | 1 | 1 | 10 | 10 |
| 64 | 1 | 1 | 1 | 1 | 5 | 5 | 3 | 5 | 5 | 5 | 4 | 4 | 3 | 3 | 3 | 3 | 6 | 6 | 6 | 6 |
| 65 | 7 | 7 | 5 | 5 | 7 | 7 | 5 | 4 | 2 | 2 | 2 | 2 | 1 | 1 | 1 | 1 | 9 | 9 | 6 | 6 |
| 66 | 9 | 9 | 9 | 9 | 10 | 10 | 7 | 7 | 3 | 3 | 1 | 1 | 9 | 9 | 7 | 7 | 7 | 7 | 7 | 7 |
| 67 | 5 | 5 | 5 | 5 | 2 | 2 | 4 | 4 | 2 | 2 | 2 | 2 | 1 | 1 | 1 | 1 | 1 | 1 | 2 | 2 |
| 68 | 8 | 8 | 8 | 8 | 7 | 10 | 10 | 10 | 10 | 10 | 9 | 9 | 9 | 9 | 8 | 8 | 6 | 6 | 6 | 6 |
| 69 | 6 | 6 | 8 | 8 | 3 | 3 | 8 | 8 | 9 | 9 | 10 | 9 | 4 | 4 | 9 | 8 | 3 | 3 | 4 | 4 |
| 70 | 1 | 1 | 1 | 1 | 2 | 2 | 1 | 1 | 1 | 1 | 1 | 1 | 3 | 3 | 2 | 2 | 1 | 1 | 2 | 2 |
| 71 | 7 | 7 | 7 | 7 | 6 | 6 | 8 | 7 | 9 | 9 | 9 | 9 | 7 | 7 | 7 | 7 | 10 | 10 | 10 | 10 |
| 72 | 2 | 2 | 3 | 3 | 3 | 3 | 6 | 5 | 3 | 3 | 4 | 4 | 3 | 3 | 5 | 5 | 2 | 2 | 6 | 5 |
| 73 | 8 | 8 | 10 | 10 | 1 | 1 | 2 | 4 | 10 | 10 | 10 | 10 | 6 | 6 | 9 | 9 | 9 | 9 | 1 | 1 |
| 74 | 10 | 10 | 10 | 10 | 10 | 10 | 9 | 9 | 3 | 3 | 3 | 3 | 8 | 8 | 9 | 8 | 8 | 8 | 3 | 3 |
| 75 | 3 | 3 | 2 | 2 | 7 | 7 | 3 | 3 | 9 | 9 | 8 | 8 | 3 | 3 | 1 | 1 | 10 | 10 | 7 | 9 |
| 76 | 1 | 1 | 2 | 2 | 2 | 2 | 1 | 1 | 3 | 3 | 2 | 2 | 2 | 2 | 3 | 3 | 8 | 8 | 9 | 9 |
| 77 | 9 | 9 | 9 | 8 | 8 | 8 | 3 | 3 | 6 | 6 | 5 | 5 | 4 | 4 | 2 | 2 | 9 | 9 | 8 | 7 |
| 78 | 8 | 8 | 8 | 8 | 1 | 1 | 3 | 2 | 10 | 10 | 10 | 10 | 2 | 2 | 2 | 2 | 10 | 10 | 9 | 8 |
| 79 | 1 | 1 | 1 | 1 | 4 | 4 | 4 | 6 | 3 | 3 | 3 | 3 | 2 | 2 | 2 | 2 | 4 | 4 | 6 | 6 |
| 80 | 3 | 3 | 2 | 2 | 3 | 3 | 1 | 3 | 7 | 7 | 7 | 6 | 2 | 2 | 1 | 1 | 10 | 10 | 10 | 10 |
| 81 | 5 | 5 | 4 | 4 | 4 | 4 | 9 | 8 | 8 | 8 | 8 | 7 | 4 | 4 | 3 | 3 | 1 | 1 | 1 | 1 |
| 82 | 5 | 5 | 6 | 5 | 5 | 5 | 6 | 5 | 2 | 2 | 3 | 3 | 3 | 3 | 3 | 3 | 4 | 4 | 2 | 2 |
| 83 | 8 | 8 | 7 | 7 | 3 | 3 | 1 | 1 | 1 | 1 | 1 | 1 | 7 | 7 | 5 | 5 | 7 | 7 | 6 | 8 |
| 84 | 2 | 2 | 2 | 2 | 2 | 2 | 2 | 2 | 7 | 7 | 8 | 7 | 10 | 10 | 10 | 10 | 5 | 5 | 4 | 8 |
| 85 | 2 | 2 | 2 | 2 | 5 | 5 | 2 | 2 | 2 | 2 | 1 | 1 | 8 | 8 | 6 | 6 | 10 | 10 | 8 | 7 |
| 86 | 6 | 6 | 6 | 6 | 2 | 2 | 4 | 3 | 2 | 2 | 4 | 4 | 3 | 3 | 2 | 2 | 10 | 10 | 9 | 10 |
| 87 | 6 | 6 | 6 | 6 | 8 | 8 | 6 | 6 | 1 | 1 | 3 | 3 | 4 | 4 | 5 | 5 | 7 | 7 | 6 | 6 |
| 88 | 4 | 4 | 4 | 4 | 10 | 10 | 10 | 10 | 7 | 7 | 7 | 7 | 6 | 6 | 6 | 6 | 7 | 7 | 10 | 9 |
| 89 | 3 | 3 | 7 | 7 | 1 | 1 | 3 | 2 | 4 | | 5 | 5 | 6 | 6 | 8 | 8 | 8 | 8 | 7 | 7 |
| 90 | 7 | 7 | 7 | 6 | 8 | 8 | 9 | 10 | 3 | 3 | 4 | 4 | 2 | 2 | 5 | 5 | 9 | 9 | 7 | 7 |
| 91 | 2 | 2 | 5 | 6 | 5 | 6 | 6 | 9 | 8 | 7 | 7 | 8 | 8 | | 6 | 8 | 6 | 2 | 2 | 3 | 2 |
| 92 | 5 | 5 | 5 | 5 | 9 | 9 | 8 | 8 | 8 | 8 | 8 | 8 | 10 | 10 | 10 | 10 | 3 | 3 | 2 | 2 |
| 93 | 7 | 7 | 7 | 7 | 4 | 4 | 4 | 3 | 10 | 10 | 10 | 10 | 9 | 9 | 9 | 9 | 2 | 2 | 6 | 5 |
| 94 | 1 | 1 | 1 | 1 | 5 | 5 | 4 | 3 | 4 | 4 | 2 | 2 | 1 | 1 | 1 | 1 | 8 | 8 | 8 | 9 |
| 95 | 1 | 1 | 1 | 1 | 8 | 8 | 7 | 7 | 1 | 1 | 1 | 1 | 10 | 10 | 10 | 10 | 5 | 5 | 3 | 3 |
| 96 | 3 | 3 | 2 | 2 | 5 | 5 | 5 | 6 | 6 | 6 | 4 | 4 | 4 | 4 | 1 | 1 | 3 | 3 | 5 | 5 |

TABLE 13-continued

Calculated scores
Wherein P means Patient, (1) refers to a score calculated based on mRNA expression, (2) refers to a score calculated based on mutation and mRNA expression, (3) refers to a score calculated based on mutation, mRNA expression, and miRNA expression, and (4) refers to a score calculated based on mutation, mRNA expression, miRNA expression and Copy Number Variation.

|     |    |    |    |    |    |    |    |    |    |    |    |    |    |    |    |    |    |    |    |    |
|-----|----|----|----|----|----|----|----|----|----|----|----|----|----|----|----|----|----|----|----|----|
| 97  | 9  | 9  | 7  | 7  | 7  | 7  | 1  | 1  | 4  | 4  | 2  | 2  | 1  | 1  | 1  | 1  | 5  | 5  | 7  | 7  |
| 98  | 9  | 9  | 9  | 9  | 6  | 6  | 5  | 4  | 5  | 5  | 6  | 6  | 6  | 6  | 8  | 8  | 3  | 3  | 1  | 1  |
| 99  | 3  | 3  | 2  | 2  | 3  | 3  | 1  | 1  | 2  | 2  | 1  | 1  | 9  | 9  | 7  | 7  | 9  | 9  | 7  | 7  |
| 100 | 2  | 2  | 1  | 1  | 9  | 9  | 9  | 10 | 4  | 4  | 2  | 2  | 5  | 5  | 4  | 4  | 10 | 10 | 6  | 6  |
| 101 | 2  | 2  | 3  | 3  | 1  | 1  | 4  | 3  | 6  | 6  | 5  | 5  | 10 | 10 | 10 | 9  | 2  | 2  | 1  | 1  |
| 102 | 1  | 1  | 3  | 3  | 1  | 1  | 4  | 8  | 2  | 2  | 3  | 3  | 10 | 10 | 10 | 10 | 8  | 8  | 9  | 9  |
| 103 | 2  | 2  | 3  | 6  | 9  | 9  | 8  | 9  | 5  | 5  | 5  | 5  | 7  | 7  | 7  | 7  | 8  | 8  | 10 | 9  |
| 104 | 9  | 9  | 10 | 10 | 9  | 9  | 9  | 9  | 8  | 8  | 9  | 9  | 1  | 1  | 4  | 4  | 2  | 2  | 9  | 9  |
| 105 | 5  | 5  | 6  | 6  | 3  | 3  | 5  | 7  | 2  | 2  | 3  | 3  | 7  | 7  | 9  | 9  | 9  | 9  | 8  | 7  |
| 106 | 3  | 3  | 4  | 4  | 9  | 9  | 10 | 9  | 9  | 9  | 8  | 8  | 4  | 4  | 4  | 4  | 7  | 7  | 5  | 5  |
| 107 | 2  | 2  | 1  | 1  | 7  | 7  | 3  | 2  | 3  | 3  | 1  | 1  | 7  | 7  | 5  | 5  | 5  | 5  | 9  | 9  |
| 108 | 4  | 4  | 4  | 4  | 2  | 2  | 1  | 1  | 6  | 6  | 5  | 5  | 10 | 10 | 7  | 7  | 9  | 9  | 9  | 9  |
| 109 | 6  | 6  | 6  | 6  | 6  | 6  | 5  | 5  | 10 | 10 | 10 | 10 | 5  | 5  | 5  | 5  | 9  | 9  | 8  | 8  |
| 110 | 7  | 7  | 7  | 7  | 3  | 3  | 4  | 7  | 3  | 3  | 4  | 4  | 7  | 7  | 6  | 6  | 6  | 6  | 2  | 2  |
| 111 | 1  | 1  | 1  | 1  | 1  | 1  | 3  | 3  | 2  | 2  | 2  | 2  | 5  | 5  | 4  | 4  | 2  | 2  | 8  | 8  |
| 112 | 7  | 7  | 5  | 5  | 5  | 5  | 2  | 4  | 1  | 1  | 1  | 1  | 1  | 1  | 1  | 1  | 10 | 10 | 8  | 8  |
| 113 | 4  | 4  | 4  | 4  | 4  | 4  | 6  | 5  | 10 | 10 | 10 | 10 | 4  | 4  | 3  | 3  | 1  | 1  | 1  | 1  |
| 114 | 5  | 5  | 5  | 5  | 4  | 4  | 5  | 4  | 6  | 6  | 6  | 5  | 3  | 3  | 4  | 4  | 3  | 3  | 1  | 1  |
| 115 | 8  | 8  | 8  | 8  | 7  | 7  | 7  | 6  | 7  | 7  | 7  | 7  | 7  | 7  | 6  | 6  | 9  | 9  | 8  | 8  |
| 116 | 6  | 6  | 5  | 5  | 10 | 10 | 10 | 10 | 1  | 1  | 1  | 1  | 6  | 6  | 5  | 5  | 5  | 5  | 4  | 4  |
| 117 | 7  | 7  | 7  | 7  | 8  | 8  | 6  | 5  | 3  | 3  | 2  | 2  | 8  | 8  | 6  | 6  | 9  | 9  | 7  | 6  |
| 118 | 9  | 9  | 9  | 9  | 7  | 7  | 8  | 8  | 7  | 7  | 8  | 8  | 1  | 1  | 1  | 1  | 5  | 5  | 4  | 4  |
| 119 | 10 | 10 | 10 | 10 | 8  | 8  | 8  | 8  | 1  | 1  | 2  | 2  | 8  | 8  | 9  | 9  | 3  | 3  | 4  | 3  |
| 120 | 10 | 10 | 10 | 10 | 10 | 10 | 10 | 9  | 4  | 4  | 4  | 4  | 10 | 10 | 10 | 10 | 7  | 7  | 3  | 3  |
| 121 | 3  | 3  | 4  | 4  | 9  | 9  | 10 | 9  | 6  | 6  | 6  | 6  | 10 | 10 | 10 | 10 | 7  | 7  | 8  | 8  |

| P | \_ | 3 | \_ | 4 | \_ | 1 | \_ | 3 | \_ | 1 | \_ | 2 | \_ | 4 | \_ | 1 | \_ | 3 | \_ | 1 | \_ | 2 | \_ | 3 | \_ | \_ | 2 | \_ | 3 | \_ | 4 | \_ | 1 | \_ | 4 |
|---|---|---|---|---|---|---|---|---|---|---|---|---|---|---|---|---|---|---|---|---|---|---|---|---|---|---|---|---|---|---|---|---|---|---|---|

| P | Antiapoptosis | | FGF | | mTOR AKT PTEN | | | Modulators MTKPT | | | | RAS | | | | RAF | | | Telomerase | |
|---|----|----|----|----|----|----|----|----|----|----|----|----|----|----|----|----|----|----|----|----|----|
| 1  | 10 | 10 | 5  | 5  | 4  | 4  | 5  | 6  | 6  | 7  | 10 | 6  | 3  | 3  | 3  | 2  | 1  |
| 2  | 10 | 10 | 3  | 3  | 4  | 4  | 2  | 8  | 7  | 4  | 10 | 7  | 4  | 4  | 4  | 5  | 5  |
| 3  | 10 | 10 | 8  | 8  | 4  | 4  | 2  | 5  | 3  | 8  | 8  | 3  | 2  | 2  | 2  | 9  | 8  |
| 4  | 4  | 4  | 9  | 9  | 6  | 6  | 7  | 10 | 10 | 8  | 8  | 10 | 10 | 10 | 10 | 5  | 5  |
| 5  | 2  | 2  | 3  | 2  | 7  | 7  | 3  | 2  | 2  | 6  | 6  | 2  | 9  | 9  | 9  | 10 | 9  |
| 6  | 9  | 10 | 9  | 9  | 8  | 8  | 8  | 4  | 8  | 8  | 8  | 8  | 8  | 8  | 8  | 10 | 9  |
| 7  | 2  | 2  | 1  | 1  | 7  | 7  | 4  | 4  | 4  | 2  | 2  | 4  | 5  | 5  | 5  | 1  | 2  |
| 8  | 9  | 9  | 3  | 2  | 2  | 2  | 1  | 7  | 6  | 4  | 10 | 6  | 7  | 5  | 5  | 9  | 9  |
| 9  | 6  | 6  | 6  | 6  | 4  | 4  | 2  | 5  | 5  | 5  | 5  | 5  | 3  | 4  | 4  | 4  | 4  |
| 10 | 1  | 1  | 6  | 2  | 8  | 8  | 3  | 10 | 9  | 1  | 1  | 9  | 7  | 6  | 6  | 1  | 2  |
| 11 | 6  | 8  | 7  | 6  | 4  | 4  | 2  | 10 | 10 | 2  | 2  | 10 | 10 | 10 | 10 | 2  | 1  |
| 12 | 1  | 1  | 7  | 6  | 1  | 1  | 7  | 8  | 7  | 1  | 10 | 7  | 4  | 3  | 3  | 1  | 3  |
| 13 | 8  | 8  | 9  | 9  | 6  | 6  | 7  | 10 | 10 | 6  | 6  | 10 | 4  | 4  | 4  | 8  | 7  |
| 14 | 2  | 2  | 5  | 6  | 3  | 3  | 5  | 5  | 6  | 4  | 4  | 6  | 3  | 4  | 4  | 3  | 2  |
| 15 | 10 | 10 | 7  | 5  | 5  | 5  | 7  | 1  | 1  | 7  | 7  | 1  | 1  | 1  | 1  | 7  | 7  |
| 16 | 6  | 6  | 7  | 7  | 5  | 5  | 7  | 1  | 1  | 10 | 10 | 1  | 5  | 6  | 6  | 4  | 4  |
| 17 | 7  | 7  | 1  | 1  | 1  | 1  | 2  | 2  | 2  | 2  | 2  | 2  | 3  | 5  | 5  | 6  | 4  |
| 18 | 10 | 10 | 4  | 6  | 9  | 9  | 10 | 1  | 2  | 5  | 5  | 2  | 1  | 1  | 1  | 6  | 7  |
| 19 | 1  | 1  | 8  | 7  | 3  | 3  | 4  | 2  | 2  | 7  | 7  | 2  | 1  | 1  | 1  | 9  | 10 |
| 20 | 8  | 8  | 4  | 2  | 9  | 9  | 5  | 5  | 3  | 10 | 10 | 3  | 10 | 10 | 10 | 9  | 8  |
| 21 | 2  | 2  | 1  | 1  | 2  | 2  | 3  | 6  | 4  | 1  | 1  | 4  | 7  | 5  | 5  | 5  | 5  |
| 22 | 4  | 4  | 2  | 2  | 3  | 3  | 1  | 3  | 3  | 8  | 8  | 3  | 3  | 2  | 2  | 6  | 5  |
| 23 | 5  | 5  | 7  | 6  | 6  | 6  | 10 | 3  | 3  | 4  | 10 | 3  | 6  | 7  | 7  | 3  | 1  |
| 24 | 8  | 7  | 2  | 4  | 4  | 4  | 9  | 2  | 3  | 9  | 9  | 3  | 9  | 9  | 9  | 8  | 10 |
| 25 | 10 | 10 | 6  | 6  | 6  | 6  | 8  | 5  | 6  | 10 | 10 | 6  | 10 | 10 | 10 | 10 | 9  |
| 26 | 4  | 4  | 10 | 10 | 7  | 7  | 10 | 8  | 9  | 7  | 7  | 9  | 5  | 5  | 5  | 9  | 9  |
| 27 | 5  | 5  | 1  | 3  | 5  | 5  | 6  | 9  | 10 | 3  | 3  | 10 | 8  | 9  | 9  | 3  | 2  |
| 28 | 9  | 9  | 10 | 10 | 5  | 5  | 4  | 2  | 2  | 4  | 4  | 2  | 8  | 7  | 7  | 9  | 9  |
| 29 | 9  | 10 | 1  | 3  | 8  | 8  | 9  | 9  | 10 | 7  | 10 | 10 | 6  | 7  | 7  | 7  | 9  |
| 30 | 10 | 10 | 8  | 8  | 9  | 9  | 10 | 3  | 2  | 9  | 9  | 2  | 6  | 6  | 6  | 9  | 8  |
| 31 | 4  | 4  | 5  | 6  | 10 | 10 | 8  | 4  | 5  | 10 | 10 | 5  | 8  | 8  | 8  | 9  | 9  |
| 32 | 1  | 1  | 1  | 3  | 3  | 3  | 3  | 6  | 6  | 2  | 10 | 6  | 4  | 6  | 6  | 2  | 1  |
| 33 | 10 | 10 | 9  | 9  | 7  | 7  | 5  | 9  | 9  | 2  | 2  | 9  | 9  | 10 | 10 | 2  | 1  |
| 34 | 10 | 10 | 8  | 8  | 3  | 3  | 5  | 7  | 8  | 9  | 9  | 8  | 3  | 4  | 4  | 10 | 10 |
| 35 | 9  | 9  | 7  | 7  | 10 | 10 | 9  | 3  | 2  | 7  | 7  | 2  | 7  | 8  | 8  | 3  | 2  |
| 36 | 10 | 10 | 9  | 9  | 9  | 9  | 10 | 9  | 8  | 3  | 3  | 8  | 9  | 8  | 8  | 9  | 8  |
| 37 | 2  | 2  | 3  | 3  | 7  | 7  | 9  | 6  | 7  | 4  | 4  | 7  | 7  | 5  | 5  | 8  | 7  |
| 38 | 1  | 1  | 10 | 10 | 4  | 4  | 5  | 10 | 9  | 1  | 1  | 9  | 9  | 10 | 10 | 6  | 4  |
| 39 | 8  | 8  | 4  | 2  | 4  | 4  | 1  | 8  | 7  | 6  | 10 | 7  | 8  | 6  | 6  | 4  | 4  |
| 40 | 10 | 10 | 2  | 3  | 8  | 8  | 8  | 5  | 4  | 6  | 10 | 4  | 5  | 6  | 6  | 5  | 6  |
| 41 | 3  | 3  | 7  | 7  | 6  | 6  | 6  | 5  | 5  | 3  | 3  | 5  | 5  | 5  | 5  | 3  | 2  |
| 42 | 10 | 10 | 3  | 1  | 7  | 7  | 4  | 4  | 3  | 5  | 5  | 3  | 10 | 10 | 10 | 6  | 3  |
| 43 | 5  | 5  | 4  | 5  | 6  | 6  | 8  | 1  | 1  | 8  | 8  | 1  | 2  | 1  | 1  | 7  | 8  |

TABLE 13-continued

Calculated scores
Wherein P means Patient, (1) refers to a score calculated based on mRNA expression, (2) refers to a score calculated based on mutation and mRNA expression, (3) refers to a score calculated based on mutation, mRNA expression, and miRNA expression, and (4) refers to a score calculated based on mutation, mRNA expression, miRNA expression and Copy Number Variation.

| 44 | 5 | 5 | 3 | 4 | 3 | 3 | 4 | 2 | 1 | 6 | 6 | 1 | 8 | 8 | 8 | 4 | 4 |
|---|---|---|---|---|---|---|---|---|---|---|---|---|---|---|---|---|---|
| 45 | 4 | 4 | 3 | 3 | 5 | 5 | 7 | 7 | 6 | 3 | 3 | 6 | 4 | 4 | 4 | 8 | 7 |
| 46 | 7 | 7 | 1 | 1 | 2 | 2 | 3 | 5 | 6 | 2 | 10 | 6 | 8 | 8 | 8 | 3 | 2 |
| 47 | 10 | 10 | 8 | 6 | 1 | 1 | 6 | 2 | 1 | 10 | 10 | 1 | 6 | 7 | 7 | 10 | 10 |
| 48 | 7 | 7 | 5 | 5 | 1 | 1 | 4 | 3 | 4 | 7 | 7 | 4 | 1 | 1 | 1 | 8 | 8 |
| 49 | 8 | 8 | 5 | 3 | 4 | 4 | 4 | 2 | 2 | 6 | 6 | 2 | 6 | 4 | 4 | 7 | 8 |
| 50 | 10 | 10 | 6 | 7 | 2 | 2 | 10 | 8 | 9 | 6 | 6 | 9 | 5 | 4 | 4 | 7 | 8 |
| 51 | 10 | 10 | 5 | 4 | 1 | 1 | 1 | 10 | 10 | 5 | 5 | 10 | 5 | 6 | 6 | 7 | 3 |
| 52 | 1 | 1 | 1 | 3 | 7 | 7 | 6 | 10 | 10 | 3 | 3 | 10 | 7 | 9 | 9 | 5 | 3 |
| 53 | 4 | 4 | 7 | 9 | 7 | 7 | 7 | 8 | 7 | 1 | 1 | 7 | 4 | 3 | 3 | 4 | 7 |
| 54 | 2 | 2 | 5 | 4 | 8 | 8 | 4 | 8 | 8 | 1 | 1 | 8 | 7 | 9 | 9 | 1 | 1 |
| 55 | 4 | 4 | 7 | 5 | 6 | 6 | 2 | 7 | 7 | 1 | 1 | 7 | 3 | 3 | 3 | 2 | 2 |
| 56 | 6 | 9 | 10 | 10 | 3 | 3 | 4 | 5 | 6 | 9 | 9 | 6 | 1 | 3 | 3 | 10 | 10 |
| 57 | 7 | 7 | 3 | 5 | 9 | 9 | 8 | 10 | 10 | 3 | 3 | 10 | 10 | 10 | 10 | 5 | 6 |
| 58 | 3 | 3 | 2 | 2 | 3 | 3 | 1 | 7 | 6 | 1 | 1 | 6 | 9 | 7 | 7 | 4 | 6 |
| 59 | 1 | 1 | 10 | 10 | 8 | 8 | 6 | 10 | 10 | 1 | 1 | 10 | 10 | 10 | 10 | 1 | 1 |
| 60 | 1 | 1 | 10 | 10 | 8 | 8 | 8 | 6 | 8 | 1 | 1 | 8 | 9 | 10 | 10 | 5 | 4 |
| 61 | 10 | 10 | 9 | 9 | 3 | 3 | 1 | 10 | 9 | 7 | 7 | 9 | 1 | 1 | 1 | 8 | 10 |
| 62 | 8 | 8 | 6 | 7 | 4 | 4 | 10 | 1 | 1 | 10 | 10 | 1 | 3 | 2 | 2 | 10 | 10 |
| 63 | 2 | 2 | 5 | 8 | 8 | 8 | 10 | 3 | 5 | 8 | 8 | 5 | 9 | 9 | 9 | 2 | 5 |
| 64 | 6 | 6 | 10 | 10 | 10 | 10 | 9 | 4 | 3 | 3 | 3 | 3 | 10 | 8 | 8 | 4 | 5 |
| 65 | 7 | 7 | 6 | 5 | 9 | 9 | 5 | 9 | 8 | 8 | 8 | 8 | 5 | 4 | 4 | 5 | 6 |
| 66 | 1 | 1 | 2 | 1 | 5 | 5 | 2 | 9 | 8 | 3 | 3 | 8 | 8 | 7 | 7 | 1 | 1 |
| 67 | 4 | 4 | 1 | 1 | 3 | 3 | 5 | 9 | 9 | 5 | 5 | 9 | 4 | 3 | 3 | 5 | 5 |
| 68 | 10 | 10 | 9 | 8 | 10 | 10 | 8 | 6 | 6 | 6 | 6 | 6 | 10 | 10 | 10 | 5 | 8 |
| 69 | 3 | 3 | 5 | 8 | 3 | 3 | 10 | 3 | 6 | 2 | 2 | 6 | 3 | 4 | 4 | 1 | 3 |
| 70 | 10 | 10 | 1 | 1 | 9 | 9 | 9 | 1 | 1 | 7 | 7 | 1 | 5 | 4 | 4 | 8 | 7 |
| 71 | 6 | 6 | 7 | 8 | 7 | 7 | 8 | 2 | 4 | 6 | 6 | 4 | 9 | 8 | 8 | 1 | 3 |
| 72 | 10 | 10 | 2 | 4 | 3 | 3 | 4 | 8 | 9 | 5 | 10 | 9 | 5 | 7 | 7 | 2 | 2 |
| 73 | 10 | 10 | 8 | 8 | 9 | 9 | 9 | 2 | 5 | 10 | 10 | 5 | 10 | 10 | 10 | 10 | 10 |
| 74 | 8 | 8 | 9 | 9 | 2 | 2 | 3 | 8 | 9 | 8 | 8 | 9 | 6 | 7 | 7 | 7 | 5 |
| 75 | 10 | 10 | 9 | 8 | 10 | 10 | 8 | 1 | 1 | 8 | 8 | 1 | 3 | 2 | 2 | 7 | 10 |
| 76 | 10 | 10 | 10 | 10 | 10 | 10 | 10 | 1 | 1 | 10 | 10 | 1 | 1 | 2 | 2 | 4 | 3 |
| 77 | 6 | 6 | 4 | 1 | 2 | 2 | 1 | 4 | 3 | 5 | 5 | 3 | 2 | 2 | 2 | 3 | 5 |
| 78 | 10 | 9 | 2 | 6 | 9 | 9 | 9 | 1 | 1 | 10 | 10 | 1 | 1 | 1 | 1 | 2 | 3 |
| 79 | 4 | 4 | 2 | 1 | 10 | 10 | 10 | 1 | 1 | 9 | 9 | 1 | 2 | 2 | 2 | 9 | 9 |
| 80 | 10 | 10 | 9 | 10 | 1 | 1 | 9 | 6 | 6 | 7 | 7 | 6 | 1 | 1 | 1 | 10 | 10 |
| 81 | 2 | 2 | 4 | 3 | 1 | 1 | 2 | 6 | 5 | 4 | 4 | 5 | 6 | 6 | 6 | 2 | 2 |
| 82 | 4 | 4 | 6 | 5 | 6 | 6 | 3 | 10 | 9 | 3 | 3 | 9 | 6 | 7 | 7 | 1 | 2 |
| 83 | 5 | 5 | 3 | 2 | 1 | 1 | 2 | 6 | 4 | 10 | 10 | 4 | 5 | 5 | 5 | 7 | 6 |
| 84 | 10 | 10 | 4 | 5 | 9 | 9 | 7 | 6 | 5 | 4 | 4 | 5 | 8 | 9 | 9 | 5 | 4 |
| 85 | 5 | 5 | 10 | 10 | 5 | 5 | 5 | 7 | 5 | 6 | 6 | 5 | 8 | 7 | 7 | 6 | 6 |
| 86 | 9 | 9 | 8 | 8 | 4 | 4 | 8 | 7 | 8 | 9 | 9 | 8 | 9 | 9 | 9 | 3 | 6 |
| 87 | 4 | 4 | 4 | 5 | 2 | 2 | 3 | 1 | 2 | 2 | 2 | 2 | 6 | 7 | 7 | 1 | 1 |
| 88 | 10 | 10 | 6 | 7 | 8 | 8 | 8 | 1 | 1 | 9 | 9 | 1 | 9 | 9 | 9 | 6 | 3 |
| 89 | 6 | 6 | 3 | 5 | 7 | 7 | 7 | 3 | 5 | 5 | 5 | 5 | 3 | 5 | 5 | 9 | 7 |
| 90 | 10 | 10 | 7 | 7 | 10 | 10 | 10 | 4 | 5 | 2 | 2 | 5 | 2 | 4 | 4 | 10 | 10 |
| 91 | 10 | 10 | 1 | 3 | 1 | 1 | 3 | 9 | 10 | 4 | 10 | 10 | 6 | 6 | 6 | 3 | 5 |
| 92 | 2 | 2 | 2 | 2 | 10 | 10 | 9 | 8 | 7 | 2 | 2 | 7 | 9 | 10 | 10 | 4 | 4 |
| 93 | 3 | 3 | 4 | 4 | 6 | 6 | 3 | 3 | 4 | 7 | 7 | 4 | 10 | 10 | 10 | 7 | 6 |
| 94 | 1 | 1 | 6 | 4 | 1 | 1 | 1 | 3 | 3 | 9 | 10 | 3 | 2 | 1 | 1 | 1 | 1 |
| 95 | 10 | 10 | 1 | 1 | 9 | 9 | 9 | 2 | 2 | 4 | 4 | 2 | 2 | 3 | 3 | 10 | 9 |
| 96 | 2 | 2 | 3 | 4 | 2 | 2 | 2 | 5 | 3 | 3 | 10 | 3 | 10 | 9 | 9 | 2 | 3 |
| 97 | 3 | 3 | 10 | 9 | 6 | 6 | 1 | 5 | 4 | 3 | 3 | 4 | 7 | 6 | 6 | 6 | 7 |
| 98 | 2 | 2 | 5 | 4 | 5 | 5 | 5 | 6 | 7 | 2 | 2 | 7 | 7 | 8 | 8 | 2 | 1 |
| 99 | 4 | 4 | 4 | 2 | 10 | 10 | 6 | 6 | 4 | 10 | 10 | 4 | 3 | 2 | 2 | 6 | 8 |
| 100 | 9 | 9 | 9 | 9 | 2 | 2 | 2 | 9 | 8 | 5 | 5 | 8 | 4 | 5 | 5 | 8 | 8 |
| 101 | 1 | 1 | 7 | 7 | 8 | 8 | 6 | 4 | 4 | 2 | 2 | 4 | 4 | 5 | 5 | 4 | 4 |
| 102 | 10 | 10 | 2 | 2 | 10 | 10 | 10 | 4 | 3 | 10 | 10 | 3 | 7 | 3 | 3 | 10 | 10 |
| 103 | 9 | 8 | 8 | 9 | 7 | 7 | 6 | 2 | 2 | 9 | 9 | 2 | 2 | 2 | 2 | 9 | 9 |
| 104 | 10 | 10 | 4 | 6 | 10 | 10 | 1 | 3 | 7 | 5 | 10 | 7 | 5 | 8 | 8 | 1 | 1 |
| 105 | 3 | 3 | 3 | 4 | 4 | 4 | 4 | 7 | 7 | 6 | 6 | 7 | 6 | 7 | 7 | 6 | 7 |
| 106 | 5 | 5 | 10 | 10 | 10 | 10 | 7 | 7 | 9 | 10 | 10 | 9 | 1 | 1 | 1 | 8 | 6 |
| 107 | 10 | 10 | 10 | 10 | 1 | 1 | 1 | 9 | 8 | 8 | 8 | 8 | 6 | 5 | 5 | 8 | 10 |
| 108 | 10 | 10 | 5 | 4 | 8 | 8 | 2 | 7 | 5 | 9 | 9 | 5 | 10 | 9 | 9 | 3 | 6 |
| 109 | 3 | 3 | 2 | 2 | 5 | 5 | 4 | 9 | 10 | 1 | 1 | 10 | 7 | 6 | 6 | 3 | 2 |
| 110 | 9 | 9 | 6 | 5 | 5 | 5 | 7 | 4 | 4 | 9 | 9 | 4 | 4 | 3 | 3 | 6 | 5 |
| 111 | 6 | 6 | 2 | 1 | 2 | 2 | 3 | 8 | 8 | 3 | 3 | 8 | 1 | 1 | 1 | 7 | 6 |
| 112 | 8 | 8 | 8 | 8 | 1 | 1 | 1 | 3 | 2 | 8 | 8 | 2 | 2 | 3 | 3 | 4 | 3 |
| 113 | 9 | 9 | 8 | 7 | 8 | 8 | 6 | 10 | 10 | 5 | 10 | 10 | 2 | 2 | 2 | 8 | 7 |
| 114 | 5 | 5 | 8 | 8 | 6 | 6 | 5 | 8 | 8 | 5 | 5 | 8 | 4 | 3 | 3 | 4 | 6 |
| 115 | 5 | 5 | 6 | 7 | 7 | 7 | 5 | 4 | 4 | 4 | 4 | 4 | 8 | 6 | 6 | 3 | 5 |
| 116 | 10 | 10 | 6 | 4 | 2 | 2 | 6 | 4 | 3 | 6 | 6 | 3 | 1 | 1 | 1 | 8 | 7 |

TABLE 13-continued

Calculated scores
Wherein P means Patient, (1) refers to a score calculated based on mRNA expression, (2) refers to a score calculated based on mutation and mRNA expression, (3) refers to a score calculated based on mutation, mRNA expression, and miRNA expression, and (4) refers to a score calculated based on mutation, mRNA expression, miRNA expression and Copy Number Variation.

| P | | | | | | | | | | | | | | | | | |
|---|---|---|---|---|---|---|---|---|---|---|---|---|---|---|---|---|---|
| 117 | 7 | 7 | 9 | 9 | 6 | 6 | 6 | 7 | 5 | 7 | 7 | 5 | 10 | 9 | 9 | 7 | 8 |
| 118 | 10 | 10 | 5 | 6 | 5 | 5 | 9 | 9 | 9 | 1 | 1 | 9 | 2 | 2 | 2 | 2 | 4 |
| 119 | 9 | 9 | 8 | 7 | 2 | 2 | 3 | 10 | 10 | 4 | 4 | 10 | 2 | 3 | 3 | 10 | 9 |
| 120 | 6 | 6 | 4 | 3 | 9 | 9 | 6 | 7 | 7 | 9 | 9 | 7 | 7 | 8 | 8 | 5 | 3 |
| 121 | 10 | 10 | 10 | 10 | 5 | 5 | 7 | 5 | 7 | 8 | 10 | 7 | 8 | 8 | 8 | 6 | 4 |

| P | IGF_Warburg | | | WNT | | PARP | | | HDAC | | | JAK_STAT | | | HEDGEHOG | | |
|---|---|---|---|---|---|---|---|---|---|---|---|---|---|---|---|---|---|
|   | 1 | 3 | 4 | 2 | 3 | 1 | 3 | 4 | 2 | 3 | 4 | 1 | 3 | 4 | 1 | 2 | 4 |
| 1 | 9 | 9 | 9 | 3 | 2 | 5 | 8 | 8 | 5 | 4 | 4 | 5 | 6 | 6 | 4 | 4 | 4 |
| 2 | 9 | 9 | 9 | 6 | 7 | 5 | 5 | 5 | 2 | 1 | 1 | 8 | 9 | 8 | 5 | 5 | 5 |
| 3 | 10 | 10 | 10 | 1 | 1 | 9 | 8 | 8 | 9 | 6 | 6 | 3 | 2 | 2 | 8 | 8 | 7 |
| 4 | 7 | 4 | 4 | 6 | 6 | 7 | 5 | 5 | 6 | 6 | 6 | 7 | 8 | 8 | 2 | 2 | 1 |
| 5 | 4 | 3 | 3 | 7 | 6 | 2 | 3 | 3 | 4 | 4 | 3 | 7 | 8 | 9 | 4 | 4 | 4 |
| 6 | 2 | 3 | 3 | 9 | 10 | 8 | 7 | 7 | 10 | 10 | 10 | 5 | 5 | 7 | 9 | 9 | 9 |
| 7 | 3 | 2 | 2 | 4 | 3 | 1 | 6 | 6 | 6 | 7 | 7 | 5 | 5 | 5 | 6 | 6 | 6 |
| 8 | 4 | 5 | 5 | 3 | 2 | 6 | 4 | 4 | 6 | 7 | 7 | 6 | 5 | 5 | 2 | 2 | 1 |
| 9 | 3 | 3 | 3 | 3 | 3 | 1 | 1 | 1 | 4 | 4 | 4 | 7 | 8 | 8 | 4 | 4 | 3 |
| 10 | 4 | 3 | 3 | 1 | 1 | 1 | 2 | 2 | 2 | 1 | 1 | 8 | 7 | 7 | 5 | 5 | 5 |
| 11 | 8 | 8 | 8 | 9 | 8 | 6 | 5 | 5 | 8 | 7 | 7 | 8 | 7 | 6 | 7 | 7 | 6 |
| 12 | 8 | 7 | 7 | 5 | 5 | 1 | 2 | 2 | 3 | 1 | 1 | 2 | 1 | 1 | 8 | 8 | 7 |
| 13 | 1 | 1 | 1 | 6 | 6 | 10 | 9 | 9 | 8 | 6 | 6 | 9 | 8 | 8 | 8 | 8 | 9 |
| 14 | 4 | 6 | 6 | 9 | 9 | 1 | 3 | 3 | 2 | 2 | 2 | 7 | 6 | 6 | 4 | 4 | 5 |
| 15 | 1 | 1 | 1 | 8 | 8 | 10 | 9 | 10 | 7 | 6 | 6 | 3 | 3 | 3 | 9 | 9 | 10 |
| 16 | 3 | 4 | 4 | 4 | 5 | 4 | 5 | 5 | 4 | 7 | 7 | 4 | 4 | 4 | 3 | 3 | 5 |
| 17 | 4 | 4 | 4 | 4 | 4 | 7 | 6 | 6 | 3 | 3 | 2 | 10 | 10 | 10 | 1 | 1 | 1 |
| 18 | 1 | 3 | 3 |   | 6 | 9 | 8 | 8 | 1 | 5 | 4 | 6 | 7 | 7 | 1 | 1 | 2 |
| 19 | 8 | 8 | 8 | 4 | 4 | 8 | 1 | 1 | 9 | 10 | 10 | 10 | 10 | 10 | 5 | 5 | 4 |
| 20 | 9 | 8 | 8 | 1 | 1 | 10 | 9 | 9 | 7 | 5 | 5 | 3 | 2 | 2 | 10 | 10 | 10 |
| 21 | 6 | 5 | 5 | 8 | 7 | 5 | 4 | 3 | 1 | 1 | 1 | 8 | 6 | 5 | 2 | 2 | 2 |
| 22 | 8 | 7 | 7 | 7 | 6 | 6 | 5 | 5 | 1 | 1 | 1 | 4 | 3 | 3 | 5 | 5 | 4 |
| 23 | 6 | 7 | 7 | 1 | 1 | 3 | 2 | 2 | 1 | 1 | 1 | 6 | 5 | 5 | 5 | 5 | 5 |
| 24 | 8 | 9 | 9 | 1 | 2 | 9 | 10 | 10 | 5 | 3 | 6 | 7 | 9 | 9 | 6 | 6 | 7 |
| 25 | 10 | 10 | 10 | 5 | 6 | 10 | 9 | 10 | 10 | 10 | 10 | 1 | 1 | 1 | 9 | 9 | 9 |
| 26 | 9 | 10 | 10 | 9 | 10 | 3 | 4 | 4 | 10 | 9 | 9 | 8 | 7 | 7 | 9 | 9 | 9 |
| 27 | 1 | 2 | 2 | 3 | 3 | 1 | 4 | 4 | 2 | 4 | 3 | 9 | 9 | 9 | 2 | 2 | 3 |
| 28 | 10 | 10 | 10 | 10 | 10 | 8 | 6 | 6 | 5 | 5 | 5 | 2 | 2 | 2 | 8 | 8 | 8 |
| 29 | 3 | 5 | 5 | 7 | 8 | 5 | 5 | 4 | 1 | 2 | 2 | 10 | 10 | 10 | 2 | 2 | 3 |
| 30 | 10 | 10 | 10 | 8 | 8 | 10 | 9 | 9 | 9 | 10 | 10 | 4 | 2 | 2 | 8 | 8 | 8 |
| 31 | 3 | 3 | 3 | 8 | 7 | 9 | 10 | 10 | 10 | 9 | 10 | 10 | 10 | 10 | 6 | 6 | 7 |
| 32 | 6 | 6 | 6 | 4 | 4 | 1 | 2 | 2 | 3 | 3 | 3 | 3 | 3 | 2 | 5 | 5 | 5 |
| 33 | 1 | 1 | 1 | 8 | 8 | 6 | 6 | 6 | 6 | 7 | 7 | 5 | 6 | 6 | 2 | 2 | 2 |
| 34 | 4 | 5 | 8 | 8 | 9 | 9 | 10 | 10 | 10 | 9 | 9 | 2 | 2 | 4 | 9 | 9 | 9 |
| 35 | 10 | 10 | 9 | 5 | 4 | 4 | 10 | 10 | 8 | 6 | 6 | 7 | 7 | 6 | 5 | 5 | 4 |
| 36 | 10 | 10 | 10 | 9 | 7 | 4 | 3 | 3 | 6 | 5 | 4 | 4 | 3 | 3 | 9 | 9 | 9 |
| 37 | 3 | 4 | 4 | 10 | 10 | 4 | 9 | 9 | 6 | 6 | 6 | 4 | 5 | 5 | 1 | 1 | 1 |
| 38 | 10 | 10 | 10 | 10 | 10 | 5 | 4 | 4 | 7 | 7 | 7 | 3 | 3 | 3 | 9 | 9 | 9 |
| 39 | 9 | 9 | 8 | 3 | 2 | 5 | 10 | 10 | 4 | 8 | 8 | 9 | 8 | 7 | 3 | 3 | 1 |
| 40 | 1 | 1 | 1 | 4 | 4 | 2 | 8 | 7 | 1 | 2 | 2 | 1 | 2 | 2 | 3 | 3 | 3 |
| 41 | 6 | 5 | 5 | 7 | 8 | 4 | 1 | 1 | 5 | 6 | 6 | 4 | 4 | 4 | 9 | 9 | 8 |
| 42 | 6 | 7 | 6 | 5 | 3 | 3 | 3 | 3 | 4 | 3 | 3 | 10 | 10 | 10 | 5 | 5 | 6 |
| 43 | 9 | 9 | 9 | 9 | 9 | 10 | 10 | 10 | 9 | 10 | 9 | 2 | 1 | 1 | 3 | 3 | 3 |
| 44 | 4 | 5 | 4 | 5 | 6 | 4 | 1 | 1 | 2 | 4 | 4 | 7 | 7 | 7 | 4 | 4 | 4 |
| 45 | 1 | 2 | 2 | 10 | 10 | 6 | 6 | 6 | 2 | 2 | 2 | 7 | 8 | 8 | 8 | 8 | 8 |
| 46 | 2 | 2 | 2 | 5 | 5 | 2 | 2 | 2 | 1 | 1 | 1 | 3 | 3 | 3 | 1 | 1 | 2 |
| 47 | 5 | 5 | 5 | 10 | 10 | 8 | 8 | 8 | 6 | 6 | 6 | 1 | 1 | 1 | 10 | 10 | 9 |
| 48 | 2 | 2 | 2 | 10 | 10 | 8 | 10 | 10 | 3 | 3 | 3 | 6 | 6 | 6 | 10 | 10 | 10 |
| 49 | 3 | 1 | 1 | 8 | 9 | 7 | 10 | 10 | 7 | 6 | 6 | 8 | 7 | 7 | 8 | 8 | 8 |
| 50 | 7 | 6 | 5 | 2 | 2 | 5 | 4 | 4 | 4 | 4 | 4 | 4 | 4 | 5 | 6 | 6 | 6 |
| 51 | 5 | 7 | 7 | 4 | 5 | 7 | 7 | 7 | 9 | 8 | 8 | 9 | 9 | 8 | 7 | 7 | 8 |
| 52 | 5 | 6 | 5 | 6 | 7 | 4 | 3 | 5 | 5 | 5 | 5 | 4 | 5 | 5 | 1 | 1 | 2 |
| 53 | 10 | 10 | 10 | 3 | 3 | 6 | 6 | 6 | 8 | 9 | 9 | 5 | 6 | 6 | 7 | 7 | 7 |
| 54 | 5 | 5 | 5 | 6 | 5 | 2 | 2 | 2 | 4 | 2 | 2 | 3 | 2 | 2 | 6 | 6 | 6 |
| 55 | 6 | 5 | 5 | 5 | 4 | 4 | 3 | 3 | 6 | 6 | 6 | 5 | 4 | 4 | 7 | 7 | 7 |
| 56 | 8 | 9 | 9 | 4 | 5 | 9 | 7 | 8 | 9 | 8 | 8 | 1 | 1 | 1 | 8 | 8 | 8 |
| 57 | 6 | 7 | 7 | 3 | 4 | 8 | 8 | 8 | 7 | 8 | 8 | 10 | 10 | 10 | 4 | 4 | 5 |
| 58 | 4 | 3 | 3 | 2 | 2 | 2 | 1 | 1 | 2 | 2 | 2 | 9 | 9 | 9 | 3 | 3 | 3 |
| 59 | 9 | 9 | 9 | 9 | 8 | 1 | 1 | 1 | 9 | 7 | 7 | 9 | 8 | 8 | 2 | 2 | 2 |
| 60 | 1 | 1 | 1 | 10 | 10 | 1 | 2 | 2 | 6 | 7 | 7 | 6 | 6 | 6 | 1 | 1 | 2 |
| 61 | 10 | 9 | 9 | 3 | 3 | 7 | 5 | 5 | 7 | 3 | 3 | 6 | 5 | 8 | 10 | 10 | 10 |
| 62 | 5 | 4 | 4 | 8 | 8 | 10 | 10 | 9 | 10 | 10 | 10 | 2 | 2 | 2 | 10 | 10 | 9 |
| 63 | 10 | 10 | 10 | 5 | 6 | 2 | 5 | 5 | 6 | 9 | 8 | 10 | 10 | 10 | 7 | 7 | 8 |
| 64 | 9 | 9 | 9 | 6 | 5 | 5 | 7 | 7 | 5 | 4 | 4 | 3 | 3 | 3 | 10 | 10 | 10 |

TABLE 13-continued

Calculated scores
Wherein P means Patient, (1) refers to a score calculated based on mRNA expression, (2) refers to a score calculated based on mutation and mRNA expression, (3) refers to a score calculated based on mutation, mRNA expression, and miRNA expression, and (4) refers to a score calculated based on mutation, mRNA expression, miRNA expression and Copy Number Variation.

| P | | | | | | | | | | | | | | | | | | |
|---|---|---|---|---|---|---|---|---|---|---|---|---|---|---|---|---|---|---|
| 65 | 6 | 4 | 4 | 2 | 2 | 5 | 6 | 6 | 5 | 1 | 1 | 9 | 9 | 9 | 9 | 9 | 9 | |
| 66 | 1 | 1 | 1 | 1 | 1 | 1 | 1 | 2 | 1 | 1 | 9 | 9 | 9 | 4 | 4 | 2 | | |
| 67 | 2 | 2 | 2 | 3 | 2 | 2 | 1 | 1 | 1 | 4 | 4 | 3 | 4 | 4 | 4 | 4 | 3 | |
| 68 | 7 | 6 | 6 | 1 | 1 | 8 | 5 | 5 | 2 | 5 | 5 | 8 | 9 | 9 | 2 | 2 | 1 | |
| 69 | 2 | 4 | 4 | 2 | 4 | 1 | 2 | 2 | 1 | 4 | 4 | 2 | 4 | 4 | 3 | 3 | 5 | |
| 70 | 3 | 1 | 1 | 7 | 4 | 3 | 3 | 3 | 7 | 7 | 7 | 1 | 1 | 1 | 1 | 1 | 1 | |
| 71 | 5 | 8 | 8 | 2 | 3 | 7 | 1 | 1 | 4 | 6 | 6 | 10 | 10 | 10 | 6 | 6 | 7 | |
| 72 | 8 | 8 | 10 | 3 | 4 | 3 | 5 | 5 | 1 | 2 | 2 | 3 | 3 | 3 | 3 | 3 | 3 | |
| 73 | 9 | 10 | 10 | 5 | 6 | 10 | 10 | 10 | 9 | 10 | 10 | 3 | 4 | 4 | 10 | 10 | 10 | |
| 74 | 2 | 2 | 2 | 6 | 7 | 9 | 7 | 7 | 5 | 5 | 5 | 10 | 10 | 10 | 9 | 9 | 9 | |
| 75 | 10 | 10 | 10 | 6 | 3 | 6 | 5 | 5 | 8 | 7 | 9 | 4 | 4 | 3 | 8 | 8 | 7 | |
| 76 | 2 | 2 | 2 | 1 | 1 | 9 | 9 | 9 | 8 | 9 | 9 | 1 | 2 | 2 | 3 | 3 | 3 | |
| 77 | 5 | 3 | 3 | 1 | 1 | 6 | 4 | 4 | 1 | 1 | 1 | 9 | 8 | 8 | 6 | 6 | 5 | |
| 78 | 5 | 7 | 6 | 8 | 7 | 8 | 6 | 6 | 1 | 2 | 2 | 7 | 7 | 7 | 2 | 2 | 2 | |
| 79 | 10 | 10 | 10 | 2 | 2 | 10 | 10 | 10 | 10 | 10 | 10 | 1 | 1 | 1 | 10 | 10 | 10 | |
| 80 | 1 | 1 | 1 | 4 | 6 | 9 | 8 | 7 | 6 | 2 | 2 | 8 | 5 | 5 | 9 | 9 | 9 | |
| 81 | 5 | 5 | 5 | 7 | 6 | 3 | 3 | 3 | 2 | 3 | 3 | 1 | 1 | 1 | 4 | 4 | 4 | |
| 82 | 6 | 4 | 4 | 2 | 3 | 1 | 4 | 4 | 3 | 3 | 3 | 6 | 6 | 6 | 6 | 6 | 6 | |
| 83 | 9 | 8 | 8 | 9 | 8 | 7 | 7 | 7 | 2 | 1 | 1 | 8 | 7 | 7 | 3 | 3 | 2 | |
| 84 | 8 | 8 | 8 | 3 | 3 | 3 | 3 | 3 | 9 | 10 | 10 | 2 | 2 | 2 | 5 | 5 | 5 | |
| 85 | 7 | 6 | 6 | 8 | 7 | 4 | 4 | 4 | 6 | 3 | 3 | 2 | 2 | 2 | 7 | 7 | 7 | |
| 86 | 5 | 6 | 6 | 7 | 9 | 4 | 7 | 7 | 8 | 8 | 7 | 8 | 7 | 7 | 9 | 9 | 10 | |
| 87 | 7 | 8 | 7 | 3 | 3 | 7 | 7 | 7 | 3 | 4 | 4 | 5 | 5 | 5 | 5 | 5 | 6 | |
| 88 | 2 | 1 | 1 | 2 | 2 | 8 | 8 | 8 | 10 | 9 | 9 | 10 | 9 | 9 | 1 | 1 | 2 | |
| 89 | 6 | 8 | 8 | 4 | 5 | 7 | 10 | 10 | 7 | 8 | 8 | 9 | 9 | 9 | 6 | 6 | 6 | |
| 90 | 1 | 1 | 1 | 7 | 9 | 10 | 1 | 1 | 5 | 8 | 8 | 6 | 7 | 7 | 1 | 1 | 2 | |
| 91 | 4 | 6 | 6 | 4 | 5 | 2 | 3 | 3 | 4 | 9 | 9 | 2 | 4 | 4 | 3 | 3 | 4 | |
| 92 | 7 | 6 | 6 | 10 | 10 | 3 | 6 | 6 | 7 | 6 | 5 | 10 | 10 | 10 | 6 | 6 | 6 | |
| 93 | 2 | 2 | 2 | 6 | 5 | 3 | 2 | 2 | 3 | 2 | 2 | 7 | 8 | 8 | 1 | 1 | 1 | |
| 94 | 7 | 5 | 5 | 5 | 4 | 1 | 1 | 1 | 8 | 8 | 8 | 1 | 1 | 1 | 2 | 2 | 1 | |
| 95 | 3 | 3 | 3 | 7 | 7 | 9 | 7 | 7 | 10 | 9 | 9 | 3 | 3 | 3 | 1 | 1 | 1 | |
| 96 | 4 | 3 | 3 | 4 | 3 | 2 | 2 | 2 | 3 | 1 | 1 | 4 | 4 | 4 | 2 | 2 | 1 | |
| 97 | 10 | 9 | 9 | 2 | 1 | 4 | 4 | 4 | 7 | 3 | 3 | 8 | 8 | 8 | 7 | 7 | 7 | |
| 98 | 2 | 2 | 2 | 1 | 1 | 2 | 2 | 2 | 2 | 2 | 2 | 6 | 6 | 6 | 4 | 4 | 4 | |
| 99 | 7 | 7 | 7 | 2 | 1 | 4 | 4 | 4 | 8 | 10 | 10 | 2 | 1 | 1 | 7 | 7 | 6 | |
| 100 | 8 | 8 | 8 | 10 | 9 | 8 | 9 | 8 | 8 | 8 | 8 | 1 | 2 | 2 | 10 | 10 | 10 | |
| 101 | 7 | 7 | 7 | 7 | 6 | 2 | 4 | 4 | 3 | 3 | 3 | 2 | 3 | 3 | 1 | 1 | 1 | |
| 102 | 5 | 4 | 7 | 1 | 1 | 10 | 9 | 9 | 10 | 10 | 10 | 1 | 1 | 1 | 7 | 7 | 6 | |
| 103 | 3 | 4 | 4 | 8 | 7 | 8 | 8 | 8 | 10 | 10 | 10 | 7 | 8 | 10 | 6 | 6 | 4 | |
| 104 | 2 | 6 | 6 | 1 | 2 | 6 | 6 | 6 | 5 | 5 | 5 | 10 | 10 | 10 | 7 | 7 | 8 | |
| 105 | 6 | 7 | 7 | 7 | 8 | 5 | 9 | 9 | 4 | 3 | 3 | 5 | 6 | 6 | 7 | 7 | 7 | |
| 106 | 7 | 7 | 7 | 10 | 10 | | 1 | 1 | 9 | 8 | 8 | 6 | 6 | 6 | 5 | 5 | 6 | |
| 107 | 6 | 4 | 4 | 5 | 4 | 9 | 7 | 7 | 9 | 10 | 10 | 1 | 1 | 1 | 10 | 10 | 10 | |
| 108 | 8 | 8 | 8 | 6 | 5 | 3 | 2 | 2 | 7 | 4 | 4 | 5 | 5 | 5 | 6 | 6 | 5 | |
| 109 | 9 | 9 | 9 | 10 | 9 | 2 | 3 | 3 | 5 | 5 | 5 | 6 | 5 | 5 | 2 | 2 | 3 | |
| 110 | 3 | 2 | 2 | 8 | 9 | 7 | 8 | 9 | 7 | 7 | 7 | 5 | 6 | 5 | 10 | 10 | 10 | |
| 111 | 7 | 6 | 6 | 9 | 9 | 8 | 9 | 9 | 6 | 9 | 9 | 2 | 3 | 3 | 8 | 8 | 8 | |
| 112 | 5 | 4 | 4 | 10 | 10 | 6 | 7 | 8 | 9 | 8 | 8 | 5 | 3 | 3 | 10 | 10 | 10 | |
| 113 | 4 | 3 | 3 | 9 | 8 | 7 | 5 | 5 | 5 | 4 | 4 | 4 | 4 | 4 | 3 | 3 | 3 | |
| 114 | 9 | 9 | 9 | 7 | 8 | 5 | 6 | 6 | 3 | 5 | 5 | 5 | 5 | 4 | 7 | 7 | 7 | |
| 115 | 7 | 7 | 7 | 2 | 3 | 5 | 7 | 7 | 4 | 7 | 7 | 8 | 9 | 9 | 5 | 5 | 4 | |
| 116 | 1 | 1 | 1 | 6 | 7 | 10 | 10 | 9 | 10 | 9 | 9 | 4 | 4 | 4 | 10 | 10 | 10 | |
| 117 | 8 | 6 | 6 | 9 | 9 | 9 | 8 | 8 | 4 | 5 | 5 | 7 | 8 | 8 | 4 | 4 | 4 | |
| 115 | 4 | 5 | 5 | 5 | 7 | 6 | 8 | 8 | 3 | 5 | 5 | 6 | 7 | 7 | 8 | 8 | 8 | |
| 119 | 3 | 3 | 3 | 10 | 10 | 8 | 9 | 9 | 8 | 8 | 8 | 10 | 10 | 10 | 8 | 8 | 8 | |
| 120 | 2 | 2 | 2 | 2 | 2 | 7 | 6 | 6 | 3 | 2 | 5 | 9 | 10 | 9 | 3 | 3 | 3 | |
| 121 | 8 | 8 | 8 | 9 | 9 | 3 | 3 | 3 | 9 | 9 | 9 | 9 | 9 | 9 | 4 | 4 | 5 | |

| | DNA_REPAIR | | | NOTCH | | | OTHERS | | | | PDL1 | | | | CTLA4 | | | |
|---|---|---|---|---|---|---|---|---|---|---|---|---|---|---|---|---|---|---|
| | 1 | 2 | 4 | 1 | 2 | 4 | 1 | 2 | 3 | 4 | 1 | 2 | 3 | 4 | 1 | 2 | 3 | 4 |
| 1 | 6 | 6 | 6 | 1 | 1 | 1 | 8 | 8 | 7 | 7 | 3 | 3 | 9 | 9 | 9 | 9 | 9 | 9 |
| 2 | 7 | 7 | 7 | 8 | 8 | 7 | 3 | 3 | 2 | 2 | 9 | 9 | 10 | 10 | 10 | 10 | 9 | 9 |
| 3 | 10 | 10 | 10 | 6 | 6 | 4 | 6 | 6 | 4 | 4 | 7 | 7 | 1 | 1 | 6 | 6 | 4 | 4 |
| 4 | 4 | 4 | 4 | 8 | 8 | 8 | 5 | 5 | 4 | 4 | 10 | 10 | 9 | 9 | 4 | 4 | 2 | 2 |
| 5 | 2 | 2 | 2 | 7 | 7 | 5 | 9 | 9 | 8 | 8 | 7 | 7 | 2 | 2 | 10 | 10 | 10 | 10 |
| 6 | 8 | 8 | 8 | 10 | 10 | 10 | 8 | 8 | 9 | 9 | 9 | 9 | 7 | 7 | 2 | 2 | 6 | 10 |
| 7 | 1 | 1 | 1 | 2 | 2 | 1 | 7 | 7 | 6 | 6 | 4 | 4 | 5 | 5 | 6 | 6 | 3 | 3 |
| 8 | 6 | 6 | 5 | 6 | 6 | 4 | 9 | 9 | 9 | 9 | 8 | 8 | 10 | 10 | 9 | 9 | 8 | 8 |
| 9 | 4 | 4 | 3 | 7 | 7 | 6 | 1 | 1 | 1 | 1 | 6 | 6 | 6 | 5 | 7 | 7 | 7 | 7 |
| 10 | 1 | 1 | 1 | 2 | 2 | 1 | 4 | 4 | 4 | 4 | 5 | 5 | 10 | 10 | 9 | 9 | 5 | 5 |
| 11 | 5 | 5 | 4 | 6 | 6 | 8 | 10 | 10 | 10 | 10 | 4 | 4 | 8 | 8 | 9 | 9 | 8 | 8 |
| 12 | 1 | 1 | 1 | 2 | 2 | 1 | 5 | 5 | 4 | 4 | 1 | 1 | 4 | 4 | 3 | 3 | 2 | 2 |

TABLE 13-continued

Calculated scores
Wherein P means Patient, (1) refers to a score calculated based on mRNA expression, (2) refers to a score calculated based on mutation and mRNA expression, (3) refers to a score calculated based on mutation, mRNA expression, and miRNA expression, and (4) refers to a score calculated based on mutation, mRNA expression, miRNA expression and Copy Number Variation.

| P | | | | | | | | | | | | | | | | | | |
|---|---|---|---|---|---|---|---|---|---|---|---|---|---|---|---|---|---|---|
| 13 | 9 | 9 | 8 | 7 | 7 | 7 | 5 | 5 | 5 | 5 | 7 | 7 | 3 | 3 | 8 | 8 | 8 | 8 |
| 14 | 1 | 1 | 1 | 4 | 4 | 6 | 1 | 1 | 2 | 2 | 5 | 5 | 3 | 3 | 5 | 5 | 7 | 6 |
| 15 | 10 | 10 | 9 | 8 | 8 | 8 | 1 | 1 | 1 | 1 | 6 | 6 | 4 | 4 | 2 | 2 | 1 | 1 |
| 16 | 6 | 6 | 7 | 1 | 1 | 3 | 4 | 4 | 5 | 5 | 3 | 3 | 7 | 6 | 10 | 10 | 10 | 10 |
| 17 | 5 | 5 | 4 | 4 | 4 | 5 | 9 | 9 | 9 | 9 | 6 | 6 | 6 | 6 | 10 | 10 | 10 | 10 |
| 18 | 7 | 7 | 8 | 1 | 1 | 6 | 8 | 8 | 9 | 9 | 10 | 10 | 10 | 10 | 6 | 6 | 9 | 8 |
| 19 | 5 | 5 | 4 | 5 | 5 | 4 | 10 | 10 | 10 | 10 | 9 | 9 | 3 | 3 | 5 | 5 | 7 | 7 |
| 20 | 6 | 6 | 5 | 1 | 1 | 1 | 9 | 9 | 9 | 9 | 3 | 3 | 2 | 2 | 4 | 4 | 4 | 4 |
| 21 | 3 | 3 | 4 | 3 | 3 | 2 | 3 | 3 | 2 | 2 | 4 | 4 | 1 | 1 | 6 | 6 | 4 | 4 |
| 22 | 6 | 6 | 4 | 3 | 3 | 2 | 2 | 2 | 1 | 1 | 7 | 7 | 5 | 5 | 7 | 7 | 6 | 6 |
| 23 | 4 | 4 | 7 | 2 | 2 | 4 | 3 | 3 | 6 | 6 | 10 | 10 | 7 | 7 | 9 | 9 | 9 | 9 |
| 24 | 8 | 8 | 9 | 6 | 6 | 8 | 6 | 6 | 8 | 8 | 2 | 2 | 6 | 6 | 5 | 5 | 7 | 7 |
| 25 | 9 | 9 | 10 | 8 | 8 | 10 | 10 | 10 | 10 | 10 | 2 | 2 | 1 | 1 | 1 | 1 | 5 | 5 |
| 26 | 7 | 7 | 7 | 10 | 10 | 9 | 7 | 7 | 7 | 7 | 8 | 8 | 9 | 9 | 8 | 8 | 10 | 9 |
| 27 | 3 | 3 | 4 | 6 | 6 | 8 | 7 | 7 | 9 | 9 | 9 | 9 | 9 | 9 | 8 | 8 | 10 | 10 |
| 28 | 10 | 10 | 10 | 9 | 9 | 9 | 1 | 1 | 1 | 1 | 2 | 2 | 7 | 7 | 8 | 8 | 7 | 7 |
| 29 | 4 | 4 | 6 | 3 | 3 | 5 | 3 | 3 | 6 | 6 | 10 | 10 | 9 | 9 | 9 | 9 | 10 | 10 |
| 30 | 6 | 6 | 5 | 10 | 10 | 10 | 8 | 8 | 8 | 8 | 6 | 6 | 5 | 4 | 4 | 4 | 3 | 3 |
| 31 | 7 | 7 | 8 | 3 | 3 | 4 | 6 | 6 | 6 | 6 | 8 | 8 | 8 | 8 | 6 | 6 | 7 | 7 |
| 32 | 1 | 1 | 1 | 1 | 1 | 2 | 7 | 7 | 8 | 8 | 5 | 5 | 5 | 5 | 5 | 5 | 5 | 5 |
| 33 | 4 | 4 | 3 | 5 | 5 | 3 | 7 | 7 | 6 | 6 | 6 | 6 | 5 | 5 | 4 | 4 | 5 | 5 |
| 34 | 10 | 10 | 10 | 10 | 10 | 10 | | 1 | 2 | 2 | 8 | 8 | 3 | 10 | 3 | 3 | 5 | 5 |
| 35 | 8 | 8 | 8 | 10 | 10 | 10 | 10 | 10 | 10 | 10 | 2 | 2 | 10 | 10 | 5 | 5 | 4 | 4 |
| 36 | 4 | 4 | 5 | 1 | 1 | 1 | 4 | 4 | 3 | 3 | 1 | 1 | 5 | 5 | 3 | 3 | 1 | 1 |
| 37 | 2 | 2 | 2 | 4 | 4 | 6 | 4 | 4 | 4 | 4 | 8 | 8 | 4 | 4 | 6 | 6 | 7 | 7 |
| 38 | 3 | 3 | 3 | 7 | 7 | 6 | 10 | 10 | 10 | 10 | 4 | 4 | 5 | 5 | 2 | 2 | 2 | 2 |
| 39 | 8 | 8 | 8 | 7 | 7 | 6 | 3 | 3 | 3 | 3 | 7 | 7 | 6 | 6 | 10 | 10 | 9 | 9 |
| 40 | 2 | 2 | 2 | 2 | 2 | 2 | 3 | 3 | 3 | 3 | 3 | 3 | 7 | 7 | 3 | 3 | 5 | 5 |
| 41 | 4 | 4 | 4 | 5 | 5 | 3 | 7 | 7 | 7 | 7 | 5 | 5 | 3 | 3 | 3 | 3 | 3 | 3 |
| 42 | 3 | 3 | 2 | 9 | 9 | 8 | 10 | 10 | 9 | 9 | 9 | 9 | 10 | 10 | 9 | 9 | 8 | 8 |
| 43 | 9 | 9 | 9 | 4 | 4 | 3 | 8 | 8 | 8 | 8 | 2 | 2 | 3 | 3 | 1 | 1 | 2 | 2 |
| 44 | 5 | 5 | 6 | 3 | 3 | 4 | 2 | 2 | 3 | 3 | 7 | 7 | 4 | 4 | 5 | 5 | 6 | 6 |
| 45 | 8 | 8 | 7 | 8 | 8 | 9 | 6 | 6 | 5 | 5 | 10 | 10 | 10 | 10 | 6 | 6 | 6 | 6 |
| 46 | 3 | 3 | 6 | 4 | 4 | 4 | 7 | 7 | 7 | 7 | 6 | 6 | 5 | 5 | 7 | 7 | 7 | 7 |
| 47 | 9 | 9 | 9 | 10 | 10 | 10 | 2 | 2 | 3 | 3 | 9 | 9 | 1 | 1 | 2 | 2 | 3 | 3 |
| 48 | 9 | 9 | 9 | 9 | 9 | 10 | 1 | 1 | 1 | 1 | 10 | 10 | 8 | 8 | 5 | 5 | 6 | 6 |
| 49 | 9 | 9 | 8 | 9 | 9 | 8 | 9 | 9 | 8 | 8 | 10 | 10 | 8 | 8 | 10 | 10 | 9 | 8 |
| 50 | 5 | 5 | 6 | 1 | 1 | 1 | 4 | 4 | 4 | 4 | 1 | 1 | 9 | 9 | 10 | 10 | 10 | 10 |
| 51 | 8 | 8 | 9 | 8 | 8 | 8 | 4 | 4 | 7 | 7 | 10 | 10 | 4 | 4 | 7 | 7 | 7 | 7 |
| 52 | 3 | 3 | 6 | 4 | 4 | 6 | 10 | 10 | 10 | 10 | 6 | 6 | 3 | 3 | 2 | 2 | 4 | 4 |
| 53 | 6 | 6 | 7 | 3 | 3 | 3 | 1 | 1 | 1 | 1 | 6 | 6 | 6 | 6 | 7 | 7 | 6 | 6 |
| 54 | 2 | 2 | 2 | 3 | 3 | 3 | 5 | 5 | 5 | 5 | 2 | 2 | 1 | 1 | 3 | 3 | 3 | 3 |
| 55 | 4 | 4 | 3 | 3 | 3 | 2 | 7 | 7 | 6 | 6 | 6 | 6 | 4 | 4 | 2 | 2 | 2 | 2 |
| 56 | 6 | 6 | 5 | 9 | 9 | 9 | 5 | 5 | 6 | 6 | 1 | 1 | 1 | 1 | 1 | 1 | 1 | 1 |
| 57 | 6 | 6 | 7 | 4 | 4 | 3 | 9 | 9 | 9 | 9 | 9 | 9 | 8 | 8 | 8 | 8 | 9 | 9 |
| 58 | 2 | 2 | 2 | 2 | 2 | 2 | 4 | 4 | 3 | 3 | 8 | 8 | 2 | 2 | 9 | 9 | 8 | 7 |
| 59 | 2 | 2 | 2 | 9 | 9 | 9 | 8 | 8 | 9 | 9 | 6 | 6 | 2 | 2 | 4 | 4 | 4 | 4 |
| 60 | 1 | 1 | 2 | 4 | 4 | 5 | 8 | 8 | 8 | 8 | 3 | 3 | 2 | 2 | 2 | 2 | 6 | 6 |
| 61 | 8 | 8 | 5 | 10 | 10 | 10 | 3 | 3 | 2 | 2 | 2 | 2 | 3 | 3 | 3 | 3 | 1 | 1 |
| 62 | 10 | 10 | 10 | 10 | 10 | 10 | 5 | 5 | 4 | 4 | 7 | 7 | 3 | 3 | 1 | 1 | 2 | 2 |
| 63 | 3 | 3 | 3 | 6 | 6 | 7 | 10 | 10 | 10 | 10 | 7 | 7 | 4 | 4 | 4 | 4 | 7 | 6 |
| 64 | 6 | 6 | 6 | 4 | 4 | 7 | 10 | 10 | 10 | 10 | 3 | 3 | 4 | 4 | 1 | 1 | 1 | 1 |
| 65 | 7 | 7 | 6 | 7 | 7 | 5 | 2 | 2 | 1 | 1 | 7 | 7 | 3 | 3 | 6 | 6 | 4 | 4 |
| 66 | 1 | 1 | 1 | 5 | 5 | 2 | 3 | 3 | 3 | 3 | 10 | 10 | 6 | 6 | 7 | 7 | 5 | 5 |
| 67 | 1 | 1 | 1 | 3 | 3 | 2 | 1 | 1 | 1 | 1 | 3 | 3 | 9 | 8 | 6 | 6 | 6 | 6 |
| 68 | 6 | 6 | 7 | 5 | 5 | 3 | 3 | 3 | 3 | 3 | 8 | 8 | 10 | 10 | 9 | 9 | 5 | 5 |
| 69 | 2 | 2 | 5 | 2 | 2 | 6 | 1 | 1 | 2 | 2 | 8 | 8 | 9 | 9 | 5 | 5 | 9 | 9 |
| 70 | 4 | 4 | 3 | 7 | 7 | 5 | 9 | 9 | 8 | 8 | 2 | 2 | 2 | 2 | 2 | 2 | 1 | 1 |
| 71 | 7 | 7 | 8 | 5 | 5 | 5 | 6 | 6 | 6 | 6 | 7 | 7 | 4 | 4 | 8 | 8 | 10 | 9 |
| 72 | 1 | 1 | 1 | 2 | 2 | 1 | 3 | 3 | 5 | 5 | 3 | 3 | 3 | 3 | 3 | 3 | 4 | 4 |
| 73 | 10 | 10 | 10 | 1 | 1 | 5 | 10 | 10 | 10 | 10 | 3 | 3 | 8 | 8 | 10 | 10 | 10 | 10 |
| 74 | 8 | 8 | 8 | 6 | 6 | 5 | 1 | 1 | 1 | 1 | 10 | 10 | 10 | 10 | 10 | 10 | 10 | 10 |
| 75 | 5 | 5 | 7 | 10 | 10 | 9 | 6 | 6 | 5 | 5 | 4 | 4 | 5 | 5 | 2 | 2 | 1 | 1 |
| 76 | 9 | 9 | 9 | 8 | 8 | 9 | 2 | 2 | 2 | 2 | 3 | 3 | 2 | 2 | 1 | 1 | 3 | 3 |
| 77 | 7 | 7 | 7 | 2 | 2 | 1 | 3 | 3 | 3 | 3 | 10 | 10 | 7 | 7 | 8 | 8 | 4 | 4 |
| 78 | 9 | 9 | 9 | 1 | 1 | 1 | 5 | 5 | 5 | 5 | 9 | 9 | 2 | 2 | 10 | 10 | 9 | 9 |
| 79 | 9 | 9 | 9 | 3 | 3 | 5 | 6 | 6 | 7 | 7 | 1 | 1 | 1 | 1 | 1 | 1 | 1 | 1 |
| 80 | 10 | 10 | 10 | 10 | 10 | 10 | 2 | 2 | 2 | 2 | 5 | 5 | 1 | 1 | 4 | 4 | 3 | 3 |
| 81 | 2 | 2 | 2 | 1 | 1 | 1 | 4 | 4 | 3 | 3 | 5 | 5 | 2 | 2 | 5 | 5 | 6 | 6 |
| 82 | 2 | 2 | 3 | 5 | 5 | 5 | 2 | 2 | 2 | 2 | 5 | 5 | 6 | 6 | 7 | 7 | 8 | 8 |
| 83 | 8 | 8 | 6 | 6 | 6 | 4 | 2 | 2 | 2 | 2 | 10 | 10 | 6 | 6 | 5 | 5 | 4 | 4 |
| 84 | 4 | 4 | 4 | 6 | 6 | 6 | 9 | 9 | 9 | 9 | 1 | 1 | 7 | 7 | 1 | 1 | 1 | 1 |
| 85 | 8 | 8 | 7 | 8 | 8 | 6 | 4 | 4 | 3 | 3 | 1 | 1 | 3 | 3 | 6 | 6 | 4 | 4 |

TABLE 13-continued

Calculated scores
Wherein P means Patient, (1) refers to a score calculated based on mRNA expression, (2)
refers to a score calculated based on mutation and mRNA expression, (3) refers to a score
calculated based on mutation, mRNA expression, and miRNA expression, and (4) refers to a
score calculated based on mutation, mRNA expression, miRNA expression and Copy Number
Variation.

| 86 | 8 | 8 | 8 | 7 | 7 | 7 | 9 | 9 | 10 | 10 | 2 | 2 | 4 | 4 | 6 | 6 | 8 | 8 |
| 87 | 5 | 5 | 5 | 1 | 1 | 2 |  | 5 | 5 | 5 | 6 | 6 | 6 | 6 | 6 | 6 | 7 | 7 |
| 88 | 9 | 9 | 9 | 6 | 6 |  | 9 | 9 | 8 | 8 | 5 | 5 | 6 | 6 | 4 | 4 | 5 | 5 |
| 89 | 8 | 8 | 8 | 4 | 4 | 7 | 10 | 10 | 10 | 10 | 4 | 4 | 9 | 9 | 7 | 7 | 9 | 9 |
| 90 | 10 | 10 | 10 | 5 | 5 | 7 | 6 | 6 | 6 | 6 | 7 | 7 | 4 | 4 | 9 | 9 | 3 | 8 |
| 91 | 1 | 1 | 2 | 6 | 6 | 6 | 4 | 4 | 4 | 4 | 4 | 4 | 9 | 9 | 1 | 1 | 4 | 4 |
| 92 | 5 | 5 | 5 | 9 | 9 | 8 | 10 | 10 | 10 | 10 | 4 | 4 | 5 | 5 | 7 | 7 | 6 | 6 |
| 93 | 3 | 3 | 3 | 5 | 5 | 4 | 6 | 6 | 6 | 6 | 7 | 7 | 8 | 7 | 8 | 8 | 8 | 7 |
| 94 | 2 | 2 | 1 | 6 | 6 | 4 | 2 | 2 | 2 | 2 | 1 | 1 | 1 | 1 | 1 | 1 | 1 | 1 |
| 95 | 10 | 10 | 10 | 9 | 9 | 9 | 4 | 4 | 4 | 4 | 2 | 2 | 1 | 1 | 2 | 2 | 2 | 2 |
| 96 | 1 | 1 | 1 | 4 | 4 | 6 | 5 | 5 | 4 | 4 | 4 | 4 | 2 | 2 | 3 | 3 | 2 | 2 |
| 97 | 3 | 3 | 1 | 7 | 7 | 5 | 6 | 6 | 5 | 5 | 5 | 5 | 8 | 8 | 7 | 7 | 3 | 3 |
| 98 | 2 | 2 | 3 | 2 | 2 | 2 | 6 | 6 | 7 | 7 | 9 | 9 | 7 | 7 | 8 | 8 | 8 | 8 |
| 99 | 5 | 5 | 4 | 9 | 9 | 8 | 5 | 5 | 4 | 4 | 3 | 3 | 5 | 5 | 4 | 4 | 2 | 2 |
| 100 | 10 | 10 | 10 | 10 | 10 | 10 | 6 | 6 | 5 | 5 | 5 | 5 | 2 | 2 | 2 | 2 | 2 | 2 |
| 101 | 1 | 1 | 2 | 5 | 5 | 4 | 9 | 9 | 9 | 9 | 1 | 1 | 8 | 8 | 2 | 2 | 3 | 3 |
| 102 | 9 | 9 | 9 | 2 | 2 | 4 | 7 | 7 | 7 | 7 | 1 | 1 | 8 | 8 | 4 | 4 | 6 | 5 |
| 103 | 9 | 9 | 9 | 9 | 9 | 9 | 8 | 8 | 8 | 8 | 2 | 2 | 6 | 6 | 5 | 5 | 5 | 10 |
| 104 | 5 | 5 | 8 | 7 | 7 | 8 | 8 | 8 | 9 | 9 | 9 | 9 | 10 | 10 | 9 | 9 | 10 | 10 |
| 105 | 4 | 4 | 5 | 8 | 8 | 9 | 3 | 3 | 7 | 7 | 3 | 3 | 5 | 5 | 8 | 8 | 9 | 9 |
| 106 | 4 | 4 | 5 | 9 | 9 | 9 | 1 | 1 | 1 | 1 | 6 | 6 | 8 | 8 | 1 | 1 | 3 | 3 |
| 107 | 7 | 7 | 2 | 10 | 10 | 10 | 1 | 1 | 1 | 1 | 1 | 1 | 1 | 1 | 3 | 3 | 1 | 1 |
| 108 | 5 | 5 | 5 | 8 | 8 | 7 | 8 | 8 | 8 | 8 | 8 | 8 | 7 | 7 | 3 | 3 | 2 | 2 |
| 109 | 2 | 2 | 1 | 5 | 5 | 3 | 9 | 9 | 8 | 8 | 9 | 9 | 6 | 6 | 8 | 8 | 7 | 7 |
| 110 | 10 | 10 | 10 | 10 | 10 | 10 | 5 | 5 | 6 | 6 | 8 | 8 | 7 | 7 | 5 | 5 | 5 | 5 |
| 111 | 7 | 7 | 6 | 3 | 3 | 2 | 7 | 7 | 7 | 7 | 1 | 1 | 7 | 7 | 3 | 3 | 1 | 1 |
| 112 | 6 | 6 | 4 | 8 | 8 | 8 | 2 | 2 | 1 | 1 | 8 | 8 | 2 | 2 | 4 | 4 | 3 | 3 |
| 113 | 7 | 7 | 6 | 1 | 1 | 1 | 8 | 8 | 7 | 7 | 4 | 4 | 4 | 3 | 8 | 8 | 6 | 6 |
| 114 | 3 | 3 | 3 | 7 | 7 | 7 | 2 | 2 | 3 | 3 | 4 | 4 | 8 | 8 | 4 | 4 | 3 | 3 |
| 115 | 3 | 3 | 3 | 5 | 5 | 3 | 7 | 7 | 5 | 5 | 4 | 4 | 10 | 10 | 9 | 9 | 8 | 8 |
| 116 | 10 | 10 | 10 | 4 | 4 | 3 | 8 | 8 | 6 | 6 | 2 | 2 | 1 | 1 | 10 | 10 | 9 | 9 |
| 117 | 5 | 5 | 4 | 8 | 8 | 7 | 2 | 2 | 2 | 2 | 9 | 9 | 9 | 9 | 7 | 7 | 5 | 5 |
| 118 | 7 | 7 | 6 | 2 | 2 | 3 | 7 | 7 | 7 | 7 | 5 | 5 | 10 | 9 | 10 | 10 | 10 | 10 |
| 119 | 10 | 10 | 10 | 9 | 9 | 9 | 5 | 5 | 5 | 5 | 10 | 10 | 10 | 10 | 7 | 7 | 8 | 8 |
| 120 | 7 | 7 | 7 | 3 | 3 | 2 | 4 | 4 | 4 | 4 | 8 | 8 | 7 | 7 | 10 | 10 | 10 | 10 |
| 121 | 3 | 3 | 3 | 7 | 7 | 7 | 10 | 10 | 10 | 10 | 5 | 5 | 9 | 9 | 1 | 1 | 2 | 2 |

The invention claimed is:

1. A method for treating a patient having a cancer comprising determining the classification of at least ten (10) selected intervention points for said patient, wherein each intervention point comprises a set of target genes which may be blocked by a drug and said classification of intervention points comprises:
  a) characterizing a tumor sample in comparison to a normal sample from the same patient, wherein the tumor sample and the normal sample are from the same type of tissue and are from the same patient, said characterizing comprising:
    (i) determining mRNA expression for each of the genes of each selected intervention point in the tumor sample and the normal sample and determining a fold change of mRNA expression of tumor vs normal (referred to as mRNA TvN fold change) for each of the genes of each intervention point;
    (ii) wholly or partially sequencing the genes of each selected intervention point and, optionally, the p53 gene to identify genes having an activating mutation in the tumor sample;
    (iii) optionally, for each selected intervention point, determining miRNA expression of each gene of each selected intervention point in the tumor sample and the normal sample, thereby determining a fold change of miRNA expression of tumor vs normal (referred to as miRNA TvN fold change) for each of the genes; and
    (iv) optionally, for each selected intervention point, determining copy number variation (CNV) of each of the genes in the tumor sample and the normal sample and determining a tumor vs normal fold change (CNV fold change) for each of the genes exhibiting CNV;
  b) determining a mutation score for each selected intervention point and an mRNA expression score from data of step a), wherein:
    (i) if, in the tumor sample, an activating mutation of a gene of a selected intervention point is detected, then a maximal mutation score is given to the intervention point;
    (ii) the mRNA expression score is calculated based on the mean of the mRNA TvN fold change of the genes for each selected intervention point, provided that the mRNA TvN fold change of a gene is taken into consideration only if its value is at least 1.3; and
    (iii) calculating a classification score for each selected intervention point that is either:
      A) the sum of the mutation score and the mRNA expression score when an activating mutation is present; or
      B) the mRNA expression score when an activating mutation is absent;
  c) classifying the selected intervention points according to the calculated scores;

d) selecting the three intervention points having the highest calculated classification scores of the selected intervention points;
e) selecting a combination of drugs targeting the three intervention points having the highest calculated classification scores; and
f) administering to the patient the selected combination of drugs, wherein:
the at least 10 intervention points are selected from the group consisting of HER, CDK4,6, PLK/AURK/kinesins, angiogenesis, angiopoietins, immune modulators, PI3K, MET, MEK, ERK, anti-apoptosis, FGF, mTOR, Ras/Raf, telomerase, IGF/glycolysis, Wnt, PARP, HDAC, JAK-STAT, Hedgehog, NOTCH pathway, DNA repair, RET, ROS1, ALK, and UB1, and
wherein the intervention points comprise a set of target genes selected from:
EGF, TGFA, AREG, EREG, HBEGF, BTC, NRG1, NRG2, NRG4, EGFR, ERBB2, ERBB3 and ERBB4 for the HER intervention point;
CDK4, CDK6, CCND1, CCND2, CCND3, CDKN2A, CDKN2B, CCNE1, CCNE2, CCNE3 and RB1 for the CDK4,6, intervention point;
PLK1, AURKA, BORA, ILK and KIF11 for the PLK/AURK/kinesins intervention point;
VEGFA, VEGFB, VEGFC, VEGFD, VEGFR1, VEGFR2, VEGFR3, PDGFA, PDGFB, PDGFRA, PDGFRB and Kit for the angiogenesis intervention point;
THBS1, TGFB1, ANGPT1, ANGPT2, ANGPTL1, ANGPT4, TIE1 and TEK for the angiopoietins intervention point;
PD1L, PDCD1LG2, PDCD1, CTLA4 and LAG3 for the immune modulators' intervention point;
PIK3CA, PIK3CB, PIK3CD, PIK3CG, PIK3C2B, PRKCB, PRKCA, PRKCB, PIK3R1, PIK3R2 and PIK3R3 for the PI3K intervention point;
HGF, MET, AXL and MST1R for the MET intervention point;
MAP2K1, MAP2K2, MAP2K3, MAP2K4, MAP3K1, MAP3K2, MAP3K3 and MAP3K4 for the MEK intervention point;
MAPK3, MAPK1, KSR1 and MAPK11 for the ERK intervention point;
BCL2, BCLXL, BIRCS, XIAP, BAK1 and TP53 for the anti-apoptosis intervention point;
FGF1 to FGF18, FGFR1, FGFR2, FGFR3 and FGFR4 for the FGF intervention point;
mTor, AKT1, AKT2, PTEN, TSC1, TSC2, STK11, PIM1, PIM2 and PIM3 for the mTor intervention point;
KRAS, NRAS, HRAS, RAF1, BRAF and CRAF for the Ras/Raf intervention point;
TERT, TERC, TEP1, HSP90AA1, DKC1 and PTGES3 for the telomerase intervention point;
IGF1, IGF2, IGF1R, IGF2R, INSR, IRS1 and PKM for the IGF/glycolysis intervention point;
CDH1, CTNNA1, CTNNB1, WNT 1, FZD1, WNTSA, B, FZDS, WIF1 and DKK1 for the Wnt intervention point;
PARP1, BRCA1, XRCC1, RAD54L, RAD54B, ATM, ATR, CHEK1, CHEK2 and WEE1 for the PARP intervention point;
HDAC1, HDAC2, HDAC3, HDAC4 and HDAC5 for the HDAC intervention point;
JAK1, JAK2, STAT1, STAT2, STAT3 and SOCS1 for the JAK-STAT intervention point;
SHH, PTCH1, SMO, STK36, PRKACA, SUFU and Gill for the Hedgehog intervention point;
NOTCH1, Adam17, PSEN1, NCSTN, JAG1, SRRT and APH1A for the NOTCH intervention point;
ERCC1, RAD52, XRCC4, RAD51, BRCA1, NEDD8 and NAE1 for the DNA repair intervention point; and
RET, ROS1, ALK and UB1 for the set of other genes intervention point.

2. The method according to claim 1, further comprising p53 gene sequencing.

3. The method according to claim 1, wherein for each intervention point, the method comprises determining miRNA expression of each of the genes of each intervention point, and wherein, before the step (b),
a mean miRNA fold change for each gene of each intervention point is calculated as the mean of the miRNA TvN fold change for the gene,
a corrected mRNA TvN fold change is calculated by dividing the mean mRNA TvN fold change by the mean miRNA TvN fold change, and
the corrected mRNA TvN fold change of the gene is then used to calculate the mean of the mRNA TvN fold change of each of the genes for each intervention point.

4. The method according to claim 3, the method comprising calculating a corrected mRNA TvN fold change for each of the genes of the following intervention points: mTOR, Ras/Raf, ERK, PI3K and Immune Modulators, if selected as an intervention point.

5. The method according to claim 1, wherein for each selected intervention point, the method comprises determining the CNV of each of the genes of the selected intervention point.

6. The method according to claim 5, wherein a corrected mRNA TvN fold change of each gene of a selected intervention point is calculated by multiplying the mRNA TvN fold change of the gene by the CNV fold change of the gene, and the corrected mRNA TvN fold change of the gene is then used to calculate the mean of the mRNA TvN fold change of each of the genes for each selected intervention point.

7. The method according to claim 1, wherein the at least 10 selected intervention points are selected from: Her, CDK4,6, PLK/AURK/Kinesins, angiogenesis, immune modulators, PI3K, MET, MEK, ERK, anti-apoptosis, FGF, mTOR, Ras/Raf, IGF/glycolysis, Wnt, PARP, and DNA repair.

* * * * *

UNITED STATES PATENT AND TRADEMARK OFFICE
CERTIFICATE OF CORRECTION

| | | |
|---|---|---|
| PATENT NO. | : 11,124,836 B2 | Page 1 of 1 |
| APPLICATION NO. | : 15/316529 | |
| DATED | : September 21, 2021 | |
| INVENTOR(S) | : Vladimir Lazar | |

It is certified that error appears in the above-identified patent and that said Letters Patent is hereby corrected as shown below:

In the Claims

<u>Column 76,</u>
Lines 1-2, "WNTSA, B, FZDS," should read --WNT5A, B, FZD5,--.
Line 10, "and Gill" should read --and GLI1--.

Signed and Sealed this
Nineteenth Day of April, 2022

Katherine Kelly Vidal
*Director of the United States Patent and Trademark Office*